(12) United States Patent
Klamp et al.

(10) Patent No.: US 8,840,902 B2
(45) Date of Patent: Sep. 23, 2014

(54) TUMOR VACCINATION INVOLVING A HUMORAL IMMUNE RESPONSE AGAINST SELF-PROTEINS

(75) Inventors: Thorsten Klamp, Mainz (DE); Ugur Sahin, Mainz (DE); Ozlem Tureci, Mainz (DE); Michael Koslowski, Frankfurt/Main (DE); Thomas Hiller, Mainz (DE); Jens Schumacher, Heidelberg (DE)

(73) Assignee: BioNTech AG (DE)

( * ) Notice: Subject to any disclaimer, the term of this patent is extended or adjusted under 35 U.S.C. 154(b) by 0 days.

(21) Appl. No.: 13/634,696

(22) PCT Filed: Mar. 9, 2011

(86) PCT No.: PCT/EP2011/001168
§ 371 (c)(1),
(2), (4) Date: Nov. 6, 2012

(87) PCT Pub. No.: WO2011/113546
PCT Pub. Date: Sep. 22, 2011

(65) Prior Publication Data
US 2013/0052217 A1    Feb. 28, 2013

(30) Foreign Application Priority Data

Mar. 16, 2010  (EP) .................................... 10002775
Dec. 30, 2010  (EP) .................................... 10016216

(51) Int. Cl.
*A61K 39/00*   (2006.01)
*A61P 35/00*   (2006.01)

(52) U.S. Cl.
USPC ..................... 424/192.1; 424/189.1; 514/19.2

(58) Field of Classification Search
None
See application file for complete search history.

(56) References Cited

U.S. PATENT DOCUMENTS 7,527,933 B2 * 5/2009 Sahin et al. .................... 435/7.1

FOREIGN PATENT DOCUMENTS

| EP | 1 997 832 | | 12/2008 |
|---|---|---|---|
| WO | 97/35008 | | 9/1997 |
| WO | WO 97/35008 | * | 9/1997 |
| WO | 2004/084940 | | 10/2004 |
| WO | 2009/033276 | | 3/2009 |

OTHER PUBLICATIONS

Zhang et al (Cellular Immunology, 2007, 247:18-27).*
Int'l. Preliminary Report on Patentability for PCT/EP2011/001168 dated Sep. 18, 2012.
International Search Report and Written Opinion for International Patent Application No. PCT/EP2011/001168, mailed Jun. 29, 2011.
Sahin et al., "Claudin-18 splice variant 2 is a pan-cancer target suitable for therapeutic antibody development." Clinical Cancer Research: An Official Journal of the American Association for Cancer Research, Dec. 1, 2008, XP002588324.
Biragyn et al., "E. coli Expressed Lymphome IG Idiotype Antigen Fusion Proteins and Chimeric HBCAG Particles Bearing Tumor Epitopes." Cancer Biotherapy, Mar. 3, 1995, XP002035977.
Pumpens et al., "Evaluation of HBS, HBC, and FRCP Virus-Like Particles for Expression of Human Papillomavirus 16 E7 Oncoprotein Epitopes." Intervirology, Jan. 1, 2002, XP008026494.
Fagan et al., "Hepatitis B vaccine: immunogenicity and follow-up including two year booster doses in high-risk health care personnel in a London teaching hospital." Journal of Medical Virology. Jan. 1, 1987, XP002588326.
Birks et al., "Claudin 6 is a positive marker for atypical teratoid/rhabdoid tumors." Brain Pathology, Jan. 1, 2010, XP002602203.
Dong et al., "Plac1 is a tumor-specific antigen capable of eliciting spontaneous antibody responses in human cancer patients." International Journal of Cancer, May 1, 2008, XP002602204.

* cited by examiner

*Primary Examiner* — Laura B Goddard
(74) *Attorney, Agent, or Firm* — McAndrews, Held & Malloy, Ltd.

(57) ABSTRACT

The present invention relates to tumor immunotherapy, in particular to tumor vaccination, using chimeric proteins comprising all or a portion of a hepatitis B virus core antigen protein and an amino acid sequence comprising an epitope derived from the extracellular portion of a tumor-associated antigen. In particular, the present invention provides virus-like particles comprising said chimeric proteins, which are useful for eliciting a humoral immune response in a subject against the tumor-associated antigen, in particular against cells carrying said tumor-associated antigen on their surface, wherein the tumor-associated antigen is a self-protein in said subject.

5 Claims, 21 Drawing Sheets

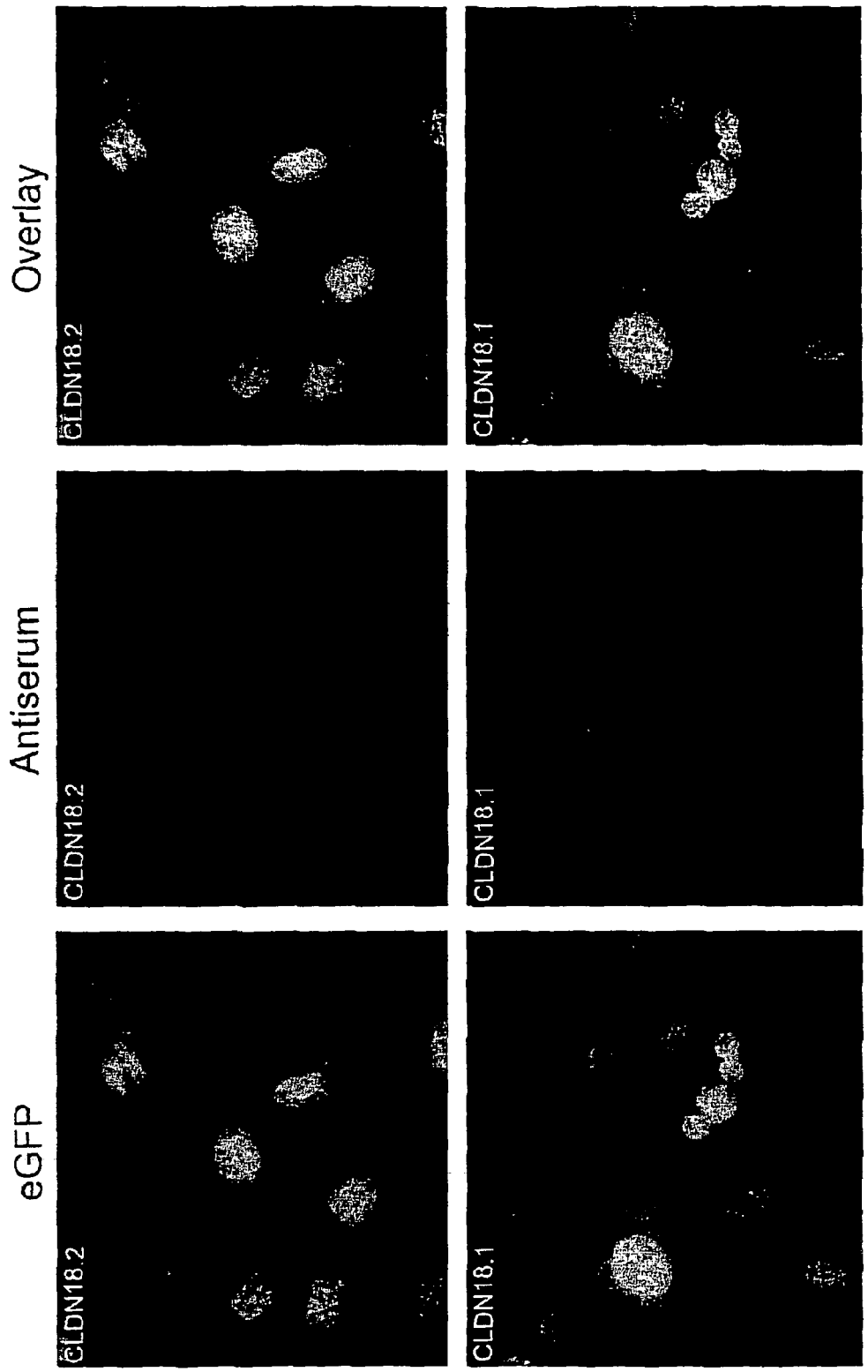

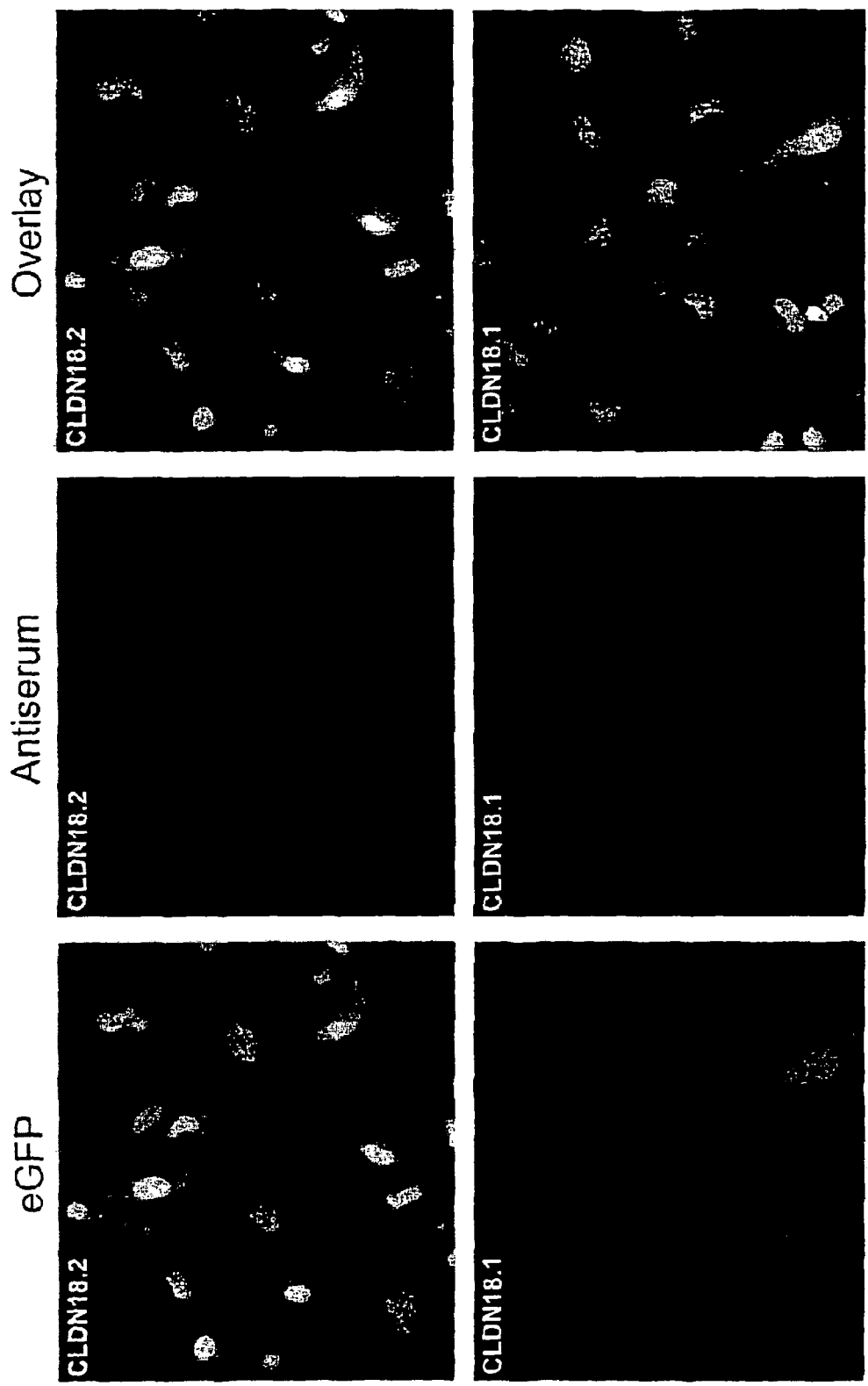

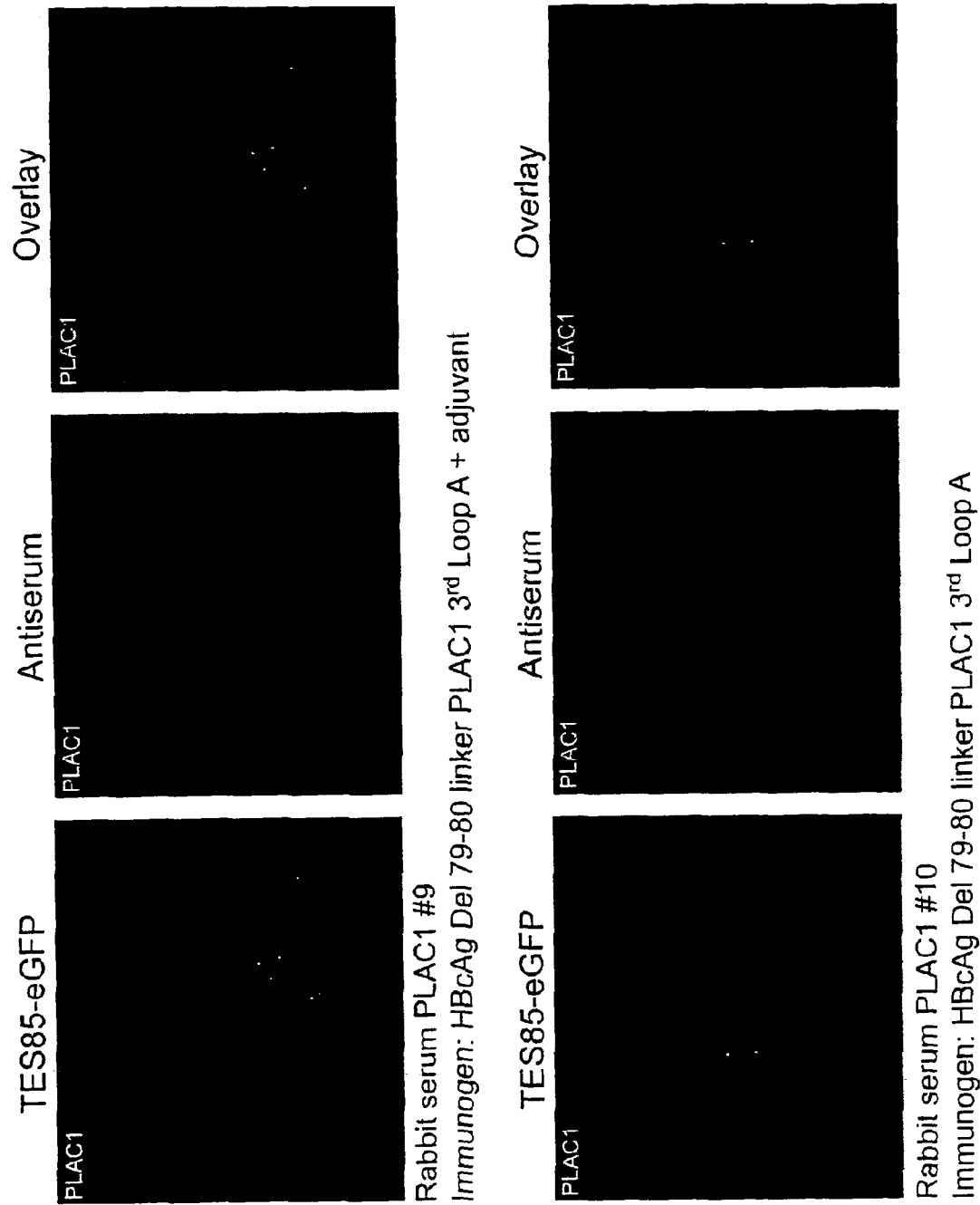

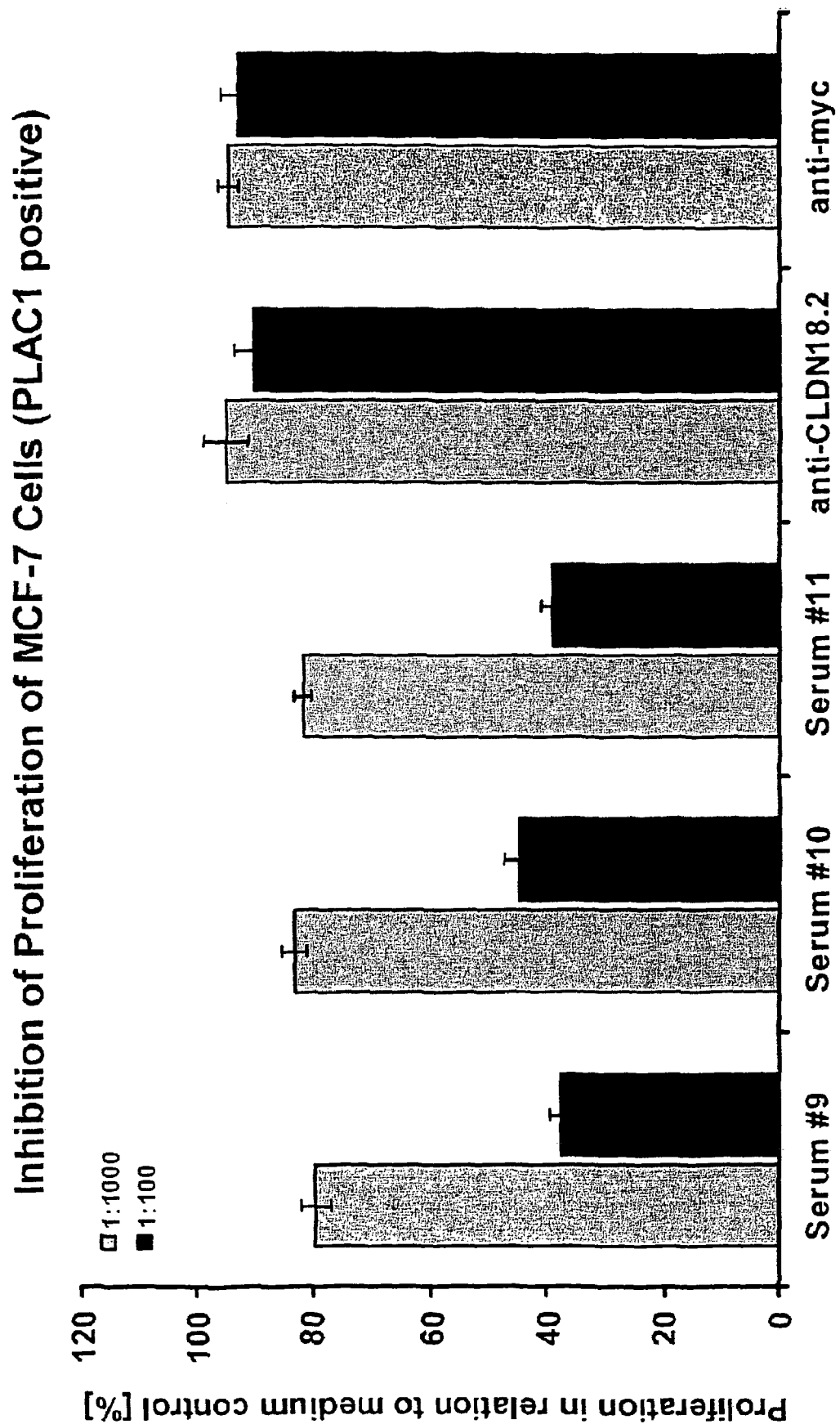

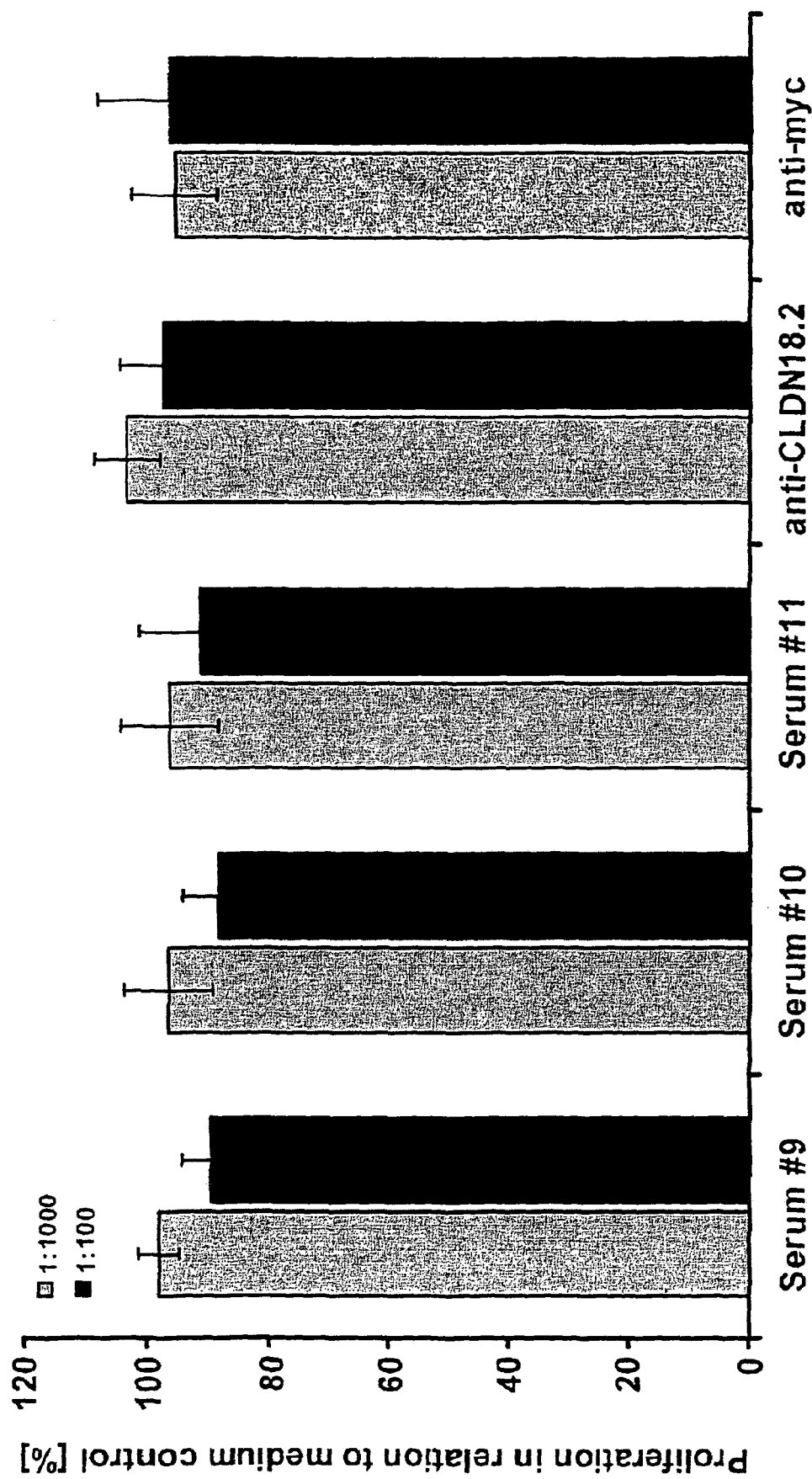

FIGURE 7A

>HBcAg Del 74-81    (SEQ ID No.: 25 amino acid & SEQ ID No.: 31 nucleic acid)

```
  1  ATGGTCGACGGCGGACTAGTGATATTGATCGTATAAAGAATTTGGCGGACCGTGGAA   60
  1   M  V  D  G  G  L  V  I  L  I  V  *  R  I  W  R  T  V  E       20

61  CTGCTGTCTTTTCTGCCGAGCGATTTTTTCCGAGCGTGATCGCTGGATACCCGCG     120
 21   L  L  S  F  L  P  S  D  F  F  R  A  *  S  L  D  T  R  A       40

121  AGCGGGCTGTATCGTGAAGCCCTGGAAGCCCGGAACATTGCAGCCCGCATCATACCGCG  180
 41   S  G  L  Y  R  E  A  L  E  A  R  N  I  A  A  R  I  I  P  R    60

181  CTGCGTCAGGGCGATTCTGTGCTGGGGCGAACTGATGACCCTGGCCACCTGGGTTGGCGGC 240
 61   L  R  Q  G  D  S  V  L  G  E  L  M  T  L  A  T  W  V  G  G    80

241  GGTGGAGGATCCGGTGGCGGTGGCAGAGATCTGGTGGTGAGCTATGTGAACACCAACATG  300
 81   G  G  G  S  G  G  G  G  R  D  L  V  V  S  Y  V  N  T  N  M   100

301  GGCCTGAAATTCGCCCAGCTTTGTGGTTCATATCAGCTGCCTGACCTTTGGCCGTGAA   360
101   G  L  K  F  A  Q  L  C  G  S  Y  Q  L  P  D  L  W  R  E       120

361  GGCCTGATTGAATATCTGGTGAGCTTTGGCGTTGGATTCGTACCCCGCCGGCATATCGT   420
121   G  L  I  E  Y  L  V  S  F  G  V  W  I  R  T  P  P  A  Y  R    140

421  CCGCCGAACGCCGCCGATTCTGAGCACCTGCCCGGAAACACCGTCGTACGTGGCGCAGC   480
141   P  P  N  A  A  D  S  E  H  L  P  E  N  T  V  V  R  G  G  S    160

481  CATCATCATCATCACCATTAA  501
161   H  H  H  H  H  H  *    166
```

FIGURE 7B

>HBcAg Del 76-81    (SEQ ID No.: 26 amino acid & SEQ ID No.: 32 nucleic acid)

```
  1  ATGGTCGACGCGGCGACTAGTGATATTCGTAAAGAATTGGGCGACCGTGGAA  60
  1   M  V  D  A  A  T  S  D  I  P  K  E  L  G  D  R  G  E   20

61  CTGCTGTCTTTCTGCCGAGGCGATTTTTTTCCGAGCGTGCGTGATCTGCTGGATACCGCG 120
 21   L  L  S  F  L  P  S  D  F  F  P  S  V  R  D  L  L  D  T  A   40

121  AGCGGGCTGTATCGTGAAGCGCTGGAAAGCCCGGAACATTGCAGCCCGCATCATACCGCG 180
 41   S  A  L  Y  R  E  A  L  E  S  P  E  H  C  S  P  H  H  T  A   60

181  CTGCGTCAGGCGATTCTGTGCTGGGGCGAACTGATGACCCTGGCCACCTGGGTTGGCGTG 240
 61   L  R  Q  A  I  L  C  W  G  E  L  M  T  L  A  T  W  V  G  V   80

241  AACGGCGGTGGAGGATCCGGTGGCGGTGGCAGAGATCTGGTGGTGAGCTATGTGAACACC 300
 81   N  G  G  G  S  G  G  G  G  R  D  L  V  V  S  Y  V  N  T   100

301  AACATGGGCCTGAAATTCGCCCAGCTGCTGTGGTTTCATATCAGCTGCCTGACCTTTGGC 360
101   N  M  G  L  K  F  A  Q  L  L  W  F  H  I  S  C  L  T  F  G   120

361  CGTGAAACCGTGATTGAATATCTGGTGAGCTTTGGCGTGTGGATTCGTACCCCGCCGGCA 420
121   R  E  T  V  I  E  Y  L  V  S  F  G  V  W  I  R  T  P  P  A   140

421  TATCGTCCGCCGAACGCGCCGATTCTGAGCACCCTGCCGGAAACCACCGTCGTACGTGGC 480
141   Y  R  P  P  N  A  P  I  L  S  T  L  P  E  T  T  V  V  R  G   160

481  GGCAGCCATCATCATCATCATCACCATTAA 507
161   G  S  H  H  H  H  H  H  H  *   168
```

FIGURE 7C

>HBcAg Del 76-79    (SEQ ID No.: 27 amino acid & SEQ ID No.: 33 nucleic acid)

```
  1  ATGGTCGACGGGCGACTAGTGATATTCGATCCGTATAAAGAATTGGCGCGACCGTGGAA   60
  1   M  V  D  G  R  L  V  I  D  P  Y  K  E  F  G  A  T  V  E      20

61  CTGCTGTCTTTTCTGCCGAGCGATTTTTTTCCGAGCGTGCGTGATCTGCTGGATACCGCG  120
 21   L  L  S  F  L  P  S  D  F  F  P  S  V  R  D  L  L  D  T  A   40

121  AGCGCGCTGTATCGTGAAGCCCTGGAAAGCCCCGAACATTGCAGCCCCCATCATACCGCG  180
 41   S  A  L  Y  R  E  A  L  E  S  P  E  H  C  S  P  H  H  T  A   60

181  CTGCGTCAGGCGATTCTGTGCTGGGGCGAACTGATGACCCTGGCCACCTGGGTGGGCGTG  240
 61   L  R  Q  A  I  L  C  W  G  E  L  M  T  L  A  T  W  V  G  V   80

241  AACGGCGGTGGAGGATCCGGTGGCGGTGGCGGTCTAGAGATCTGGTGAGCTATGTG  300
 81   N  G  G  G  G  S  G  G  G  G  G  L  E  I  L  V  S  Y  V  100

301  AACACCAACATGGGCCTGAAATTTCGCCAGCTGCTGTGGTTTCATATCAGCTGCCTGACC  360
101   N  T  N  M  G  L  K  F  R  Q  L  L  W  F  H  I  S  C  L  T  120

361  TTTGGCCGTGAAACCGTGATTGAATATCTCGTGAGCTTTGGCGTGTGGATTCGTACCCCG  420
121   F  G  R  E  T  V  I  E  Y  L  V  S  F  G  V  W  I  R  T  P  140

421  CCGGCATATCGTCCGCCGAATGCGCCGATTCTGAGCACCCTGCCCGAAACCACCGTCGTA  480
141   P  A  Y  R  P  P  N  A  P  I  L  S  T  L  P  E  T  T  V  V  160

481  CGTGGCGGCAGCCATCATCATCATCATCACCATTAA                          513
161   R  G  G  S  H  H  H  H  H  H  H  *                         170
```

FIGURE 7D

>HBcAg Del 79-80 linker   (SEQ ID No.: 28 amino acid & SEQ ID No.: 34 nucleic acid)

```
1    ATGGACATTGATCCGTATAAAGAATTTGGCGCGACCGTTGAACTGCTGAGCTTTCTGCCG   60
1     M  D  I  D  P  Y  K  E  F  G  A  T  V  E  L  L  S  F  L  P    20

61   AGCGATTTTTTTCCGAGCGTGCGTGATCTGCTGGATACCGCGAGCGCCCTGTATCGTGAA  120
21    S  D  F  F  P  S  V  R  D  L  L  D  T  A  S  A  L  Y  R  E    40

121  GCACTGGAAAGCCCCGGAACATTGTAGCCCGCATCATACCGCGCTGCGTCAGGCGATTCTG  180
41    A  L  E  S  P  E  H  C  S  P  H  H  T  A  L  R  Q  A  I  L    60

181  TGTTGGGGTGAACTGATGACCCTGGCGACCTGGGTTGGTGTTAATCTGGAAGATGGTGGC  240
61    C  W  G  E  L  M  T  L  A  T  W  V  G  V  N  L  E  D  G  G    80

241  GGCGGATCCGGTGGCGGCGGTTCTAGAGACCTGGTCGTCAGCTATGTGAACACCAACATG  300
81    G  G  S  G  G  G  G  S  R  D  L  V  V  S  Y  V  N  T  N  M   100

301  GGCCTGAAATTCGCCAACTGCTGTGTTTCATATTAGCTGCCTGACCTTTGGCGGTGAA  360
101   G  L  K  F  R  Q  L  L  W  F  H  I  S  C  L  T  F  G  R  E   120

361  ACCGTGATTGAATATCTGGTGAGCTTTGGCGTTTGGATTCGTACCCCGCCAGCTATCGT  420
121   T  V  I  E  Y  L  V  S  F  G  V  W  I  R  T  P  P  A  Y  R   140

421  CCGCCGAACGCGCCTGCCGATTCTGAGCACCCTGCCGGAAACCACCGTTGTTCGGGGTAGC  480
141   P  P  N  A  P  I  L  S  T  L  P  E  T  T  V  V  R  G  G  S   160

481  CATCATCATCATCACCATTAA  501
161   H  H  H  H  H  H  *   166
```

FIGURE 7E

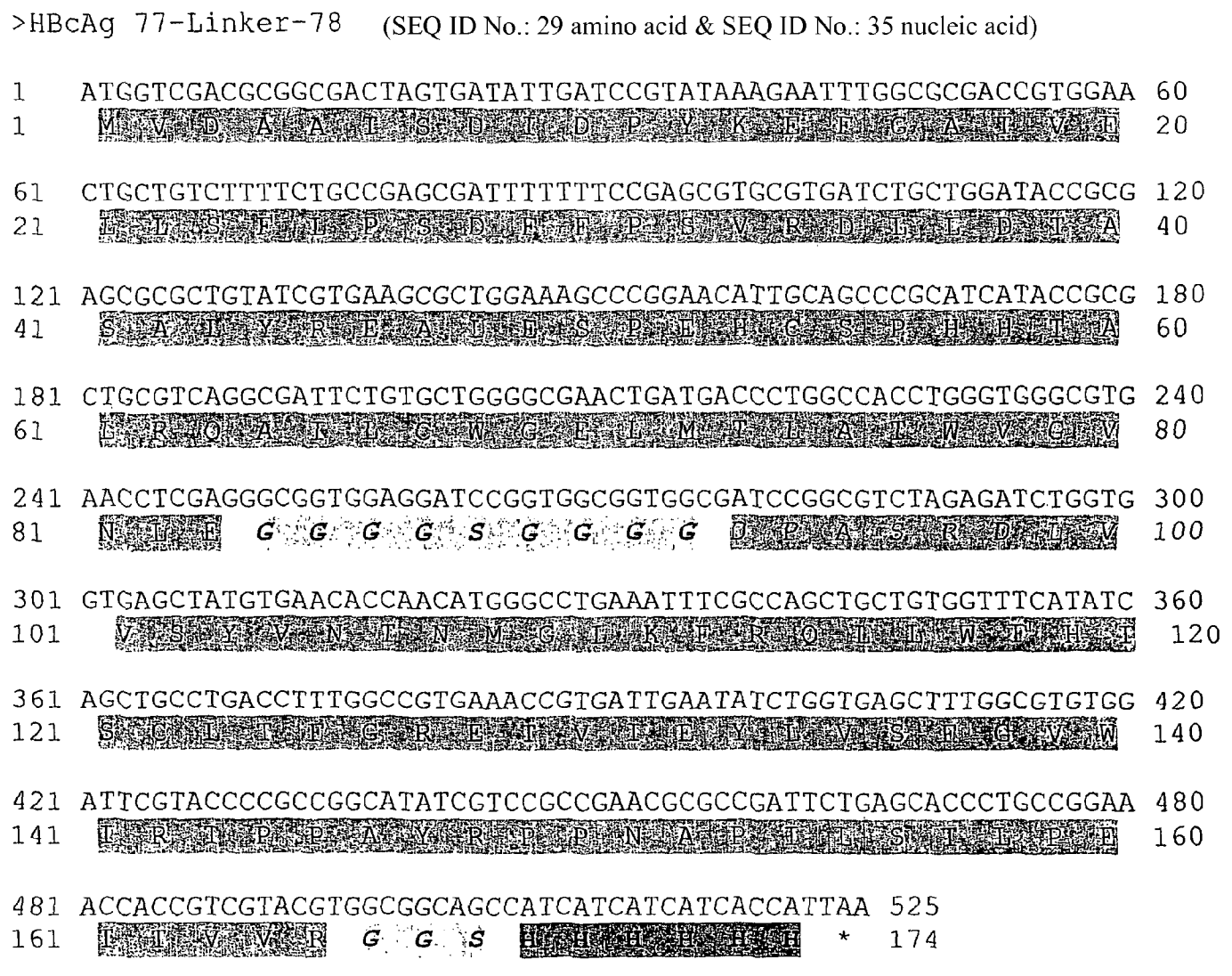

>HBcAg 77-Linker-78    (SEQ ID No.: 29 amino acid & SEQ ID No.: 35 nucleic acid)

```
  1   ATGGTCGACGGGGCCGACTAGTCGATGATATTGATCCGTATAAAGAATTTGGGCGACCGTGGAA    60
  1    M  V  D  A  A  H  S  D  *  D  P  V  K  E  F  G  A  H  V  E      20

61   CTGCTGTCTCTTTTCTGCCGAGCGATTTTTTTCCGAGCGGTGCTGTCGATACCGCG          120
 21    L  L  S  L  F  A  E  P  S  D  F  F  P  S  V  R  D  I  T  A

FIGURE 7F

>HBcAg Del 79-80     (SEQ ID No.: 30 amino acid & SEQ ID No.: 36 nucleic acid)

```
1    ATGGACATTGATCCGTATAAAGAATTTGGCGCGACCGTTGAACTGCTGAGCTTTCTGCCG   60
1     M  D  I  D  P  Y  K  E  F  G  A  T  V  E  L  L  S  F  L  P    20

61   AGGGATTTTTTCCGAGCTGCGTGCTGATCTGCTGGATACCGGAGCCGCTGTATCGTGAA   120
21    S  D  F  F  P  S  V  R  D  L  L  D  T  G  A  S  A  L  Y  R  E   40

121  GCACTGGAAAGCCCCGAACATTGTAGCCCGCATCATACCGCGCTGCGTCAGGCGATTCTG  180
41    A  L  E  S  P  E  H  C  S  P  H  H  T  A  L  R  Q  A  I  L    60

181  TGTTGGGGTGAACTGATGACCCTGGCCACTGGTTGTTAATCTCGAGGACTCTAGA       240
61    C  W  G  E  L  M  T  L  A  T  W  V  G  V  N  L  E  D  S  R    80

241  GACCTGGTGGTGAGCTATGTGAACACCAACATGGGCCTGAAATTTCGCCAACTGCTGTGG  300
81    D  L  V  V  S  Y  V  N  T  N  M  G  L  K  F  R  Q  L  L  W   100

301  TTTCATATTAGCTGCCTGACCTTTGGCCGTGAAACCGTGATTGAATATCTGGTGAGCTTT  360
101   F  H  I  S  C  L  T  F  G  R  E  T  V  I  E  Y  L  V  S  F   120

361  GGCGTTTGGATTCGTACCCCGCCAGCTATCGTCCGCCGAACGCCGGATTCTGAGCACC   420
121   G  V  W  I  R  T  P  P  A  Y  R  P  P  N  A  P  I  L  S  T   140

421  CTGCCCGGAAACCACCGTTGTTCCGGGGTAGCCATCATCATCATCACCATTAA          474
141   L  P  E  T  T  V  V  P  G  S  H  H  H  H  H  H  *           157
```

FIGURE 8A

>HBcAg Del 79-80 linker CLDN18.2-EC1 short (SEQ ID No.: 37 amino acid & SEQ ID No.: 41 nucleic acid)

```
1   ATGGACATTGATCCGTATAAAGAATTTGGCGCGACCGTTGAACTGCTGAGCTTTCTGCCG 60
1    M  D  I  D  P  Y  K  E  F  G  A  T  V  E  L  L  S  F  L  P  20

61  AGCGATTTTTTTCCGAGCGTGCGTGATCTGCTGGATACCGCGAGCGCGCTGTATCGTGAA 120
21   S  D  F  F  P  S  V  R  D  L  L  D  T  A  S  A  L  Y  R  E  40

121 GCACTGGAAAGCCCGGAACATTGTAGCCCGCATCATACCGCGCTGCGTCAGGCGATTCTG 180
41   A  L  E  S  P  E  H  C  S  P  H  H  T  A  L  R  Q  A  I  L  60

181 TGTTGGGGTGAACTGATGACCCTGGCGACCTGGGTTGGTGTTAATCTCGAGGATGGTGGC 240
61   C  W  G  E  L  M  T  L  A  T  W  V  G  V  N  L  E  D  G  G  80

241 GGCGGATCCGGCGGAGGCGGAACCCAGGATCTGTATAACAATCCGGTGACCGGCGGAGGC 300
81   G  G  S  G  G  G  G  T  Q  D  L  Y  N  N  P  V  T  G  G  G  100

301 GGATCCGGTGGCGGTGGTTCTAGAGACCTGGTGGTGAGCTATGTGAACACCAACATGGGC 360
101  G  S  G  G  G  G  S  R  D  L  V  V  S  Y  V  N  T  N  M  G  120

361 CTGAAATTTCGCCAACTGCTGTGGTTTCATATTAGCTGCCTGACCTTTGGCCGTGAAACC 420
121  L  K  F  R  Q  L  L  W  F  H  I  S  C  L  T  F  G  R  E  T  140

421 GTGATTGAATATCTGGTGAGCTTTGGCGTTTGGATTCGTACCCCGCCAGCGTATCGTCCG 480
141  V  I  E  Y  L  V  S  F  G  V  W  I  R  T  P  P  A  Y  R  P  160

481 CCGAACGCGCCGATTCTGAGCACCCTGCCGGAAACCACCGTTGTTCGCGGCGGTAGCCAT 540
161  P  N  A  P  I  L  S  T  L  P  E  T  T  V  V  R  G  G  S  H  180

541 CATCATCATCACCATTAA 558
181  H  H  H  H  H  *  185
```

FIGURE 8B

>HBcAg Del 79-80 CLDN18.2-EC1 short (SEQ ID No.: 38 amino acid & SEQ ID No.: 42 nucleic acid)

```
1   ATGGACATTGATCCGTATAAAGAATTTGGCGCGACCGTTGAACTGCTGAGCTTTCTGCCG 60
1    M  D  I  D  P  Y  K  E  F  G  A  T  V  E  L  L  S  F  L  P  20

61  AGCGATTTTTTTCCGAGCGTGCGTGATCTGCTGGATACCGCGAGCGCGCTGTATCGTGAA 120
21   S  D  F  F  P  S  V  R  D  L  L  D  T  A  S  A  L  Y  R  E  40

121 GCACTGGAAAGCCCGGAACATTGTAGCCCGCATCATACCGCGCTGCGTCAGGCGATTCTG 180
41   A  L  E  S  P  E  H  C  S  P  H  H  T  A  L  R  Q  A  I  L  60

181 TGTTGGGGTGAACTGATGACCCTGGCGACCTGGGTTGGTGTTAATCTCGAGGACACCCAG 240
61   C  W  G  E  L  M  T  L  A  T  W  V  G  V  N  L  E  D  T  Q  80

241 GATCTGTATAACAACCCGGTGACCTCTAGAGACCTGGTGGTGAGCTATGTGAACACCAAC 300
81   D  L  Y  N  N  P  V  T  S  R  D  L  V  V  S  Y  V  N  T  N  100

301 ATGGGCCTGAAATTTCGCCAACTGCTGTGGTTTCATATTAGCTGCCTGACCTTTGGCCGT 360
101  M  G  L  K  F  R  Q  L  L  W  F  H  I  S  C  L  T  F  G  R  120

361 GAAACCGTGATTGAATATCTGGTGAGCTTTGGCGTTTGGATTCGTACCCCGCCAGCGTAT 420
121  E  T  V  I  E  Y  L  V  S  F  G  V  W  I  R  T  P  P  A  Y  140

421 CGTCCGCCGAACGCGCCGATTCTGAGCACCCTGCCGGAAACCACCGTTGTTCGCGGCGGT 480
141  R  P  P  N  A  P  I  L  S  T  L  P  E  T  T  V  V  R  G  G  160

481 AGCCATCATCATCATCACCATTAA 504
161  S  H  H  H  H  H  H  *  167
```

FIGURE 8C

>HBcAg Del 79-80 linker PLAC1 3rd Loop A (SEQ ID No.: 39 amino acid & SEQ ID No.: 43 nucleic acid)

```
  1  ATGGACATTGATCCGTATAAAGAATTTGGCGCCACCGTTGAACTGCTGAGCTTTCTGCCG    60
  1   M  D  I  D  P  Y  K  E  F  G  A  T  V  E  L  L  S  F  L  P    20

61  AGCGATTTTTTCCGAGCGTGCGTGAACATTGCTGCTGGATACCGCGAGCGCCTGTATCGTGAA   120
 21   S  D  F  F  P  S  V  R  D  L  L  D  T  A  S  A  L  Y  R  E    40

121  GCACTGGAAAGCCCGGAACATTGTAGCCCGCATCATACCGCGCTGCGTCAGGCGATTCTG   180
 41   A  L  E  S  P  E  H  C  S  P  H  H  T  A  L  R  Q  A  I  L    60

181  TGTTGGGGTGAACTGATGACCCTGGCGACTGGGTTGGTGTAATCTCGAGGATGTGGC   240
 61   C  W  G  E  L  M  T  L  A  T  W  V  G  V  N  L  E  D  G  G    80

241  GGCGGATCCGGCGGCGGAGGCGGAGTTTTCTCTGAAGAAGAACACCCAGGTTCCGGGCGGA   300
 81   G  G  S  G  G  G  G  G  V  F  S  E  E  E  H  T  Q  V  P  G   100

301  GGCGGATCCGGTGGCGGTGGTTCTAGAGACCTGGTGGTGAGCTATGTGAACACCAACATG   360
101   G  G  S  G  G  G  G  S  R  D  L  V  V  S  Y  V  N  T  N  M   120

361  GGCCTGAAATTCGCCAACTGCTGTGTTCATATTAGCTGCCTGACCTTTGGCCGTGAA    420
121   G  L  K  F  P  Q  L  L  N  F  H  I  S  C  L  T  F  G  R  E   140

421  ACCGTGATTGAATATCGTGAGCTTTGGCCGTTGGATTCGTACCCCGCCAGCGTATCGT   480
141   T  V  I  E  Y  R  E  L  W  R  L  I  R  T  P  P  A  Y  R   160

481  CCGCCCGAACGCGCCCGATTCTGAGCACCCTGCCGGAAACACCGTTGTTCGGGCGGTAGC   540
161   P  P  N  A  R  F  L  S  T  L  P  E  T  P  L  V  R  G  G  S   180

541  CATCATCATCATCACCATTAA   561
181   H  H  H  H  H  H  *   186
```

FIGURE 8D

>HBcAg Del 79-80 PLAC1 3rd Loop B (SE

FIGURE 9
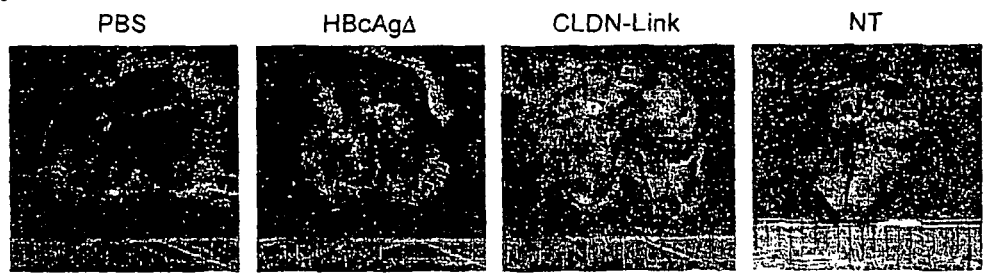
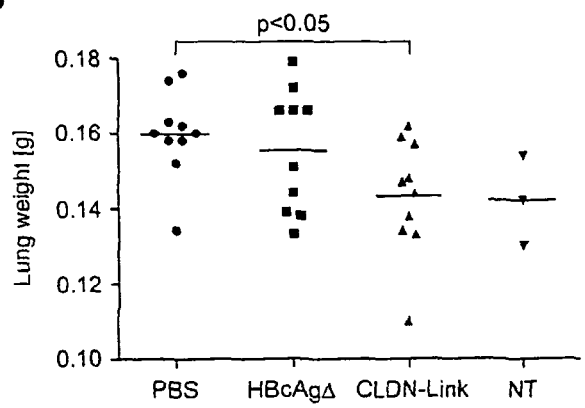
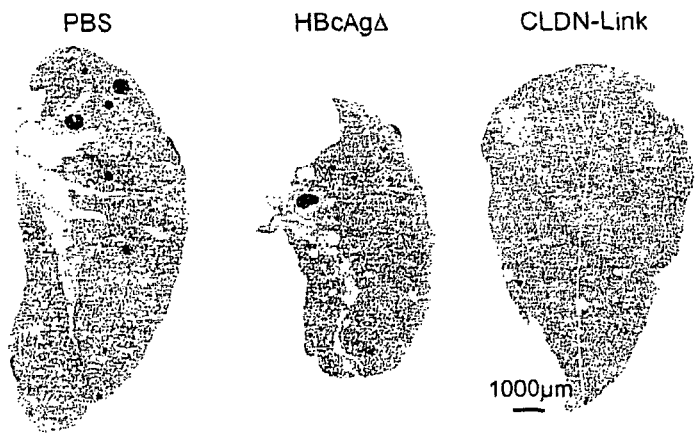
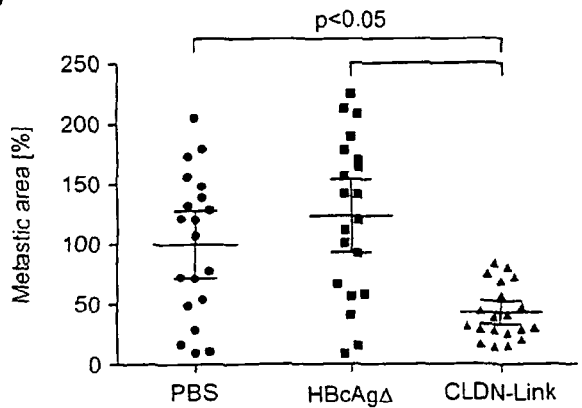

TUMOR VACCINATION INVOLVING A HUMORAL IMMUNE RESPONSE AGAINST SELF-PROTEINS

The present application is filed pursuant to 35 U.S.C. 371 as a U.S. National Phase application of International Patent Application No. PCT/EP2011/001168, entitled "Tumor Vaccination Involving A Humoral Immune Response Against Self-Proteins" which was filed Mar. 9, 2011, claiming the benefit of priority to European Patent Application No. 10 002 775.4 which was filed on Mar. 16, 2010 and European Patent Application No. 10 016 216.3 which was filed on Dec. 30, 2010. The entire text of the aforementioned applications are incorporated herein by reference in their entireties.

TECHNICAL FIELD OF THE INVENTION

The present invention is in the field of tumor immunotherapy. In particular, the present invention provides means for effective vaccination of a subject against tumor-associated antigens which are self-proteins in said subject. The present invention provides a protein comprising a hepatitis B virus core antigen protein or a portion thereof and an amino acid sequence comprising an epitope of a tumor-associated antigen. Furthermore, the present invention provides virus-like particles comprising said protein and an immunogenic composition comprising said protein or said particles, in particular, for use in prophylactic and/or therapeutic applications, for example, for cancer vaccination and/or therapy. The present invention also provides methods for breaking self-tolerance against the above tumor-associated antigens and for treating and/or preventing a tumorigenic disease in a subject.

BACKGROUND OF THE INVENTION

Recombinant vaccines are of particular importance in human and veterinary medicine for prophylaxis and therapy of infectious and cancerous diseases. It is the aim of an immunization with a recombinant vaccine to induce a specific immune reaction against a defined antigen, which is effective in prevention or therapy of defined diseases. Known recombinant vaccines are based on recombinant proteins, synthetic peptide fragments, recombinant viruses, or nucleic acids.

Most of the recombinant vaccines can be divided into two categories: a) vaccines inducing a humoral B cell-mediated immune response which result in specific antibody production, and b) vaccines inducing cellular T-cell mediated immune responses, in particular cytotoxic T-lymphocytes.

Induction of antibodies by preventive vaccination against infectious diseases (e.g., vaccinations against children's diseases) is one of the most effective medical interventions and has been applied successfully for many years. Recently, it also has been shown that the therapeutic passive administration of monoclonal antibodies (mAb) directed against self-proteins represents an effective therapy method of acute and chronic diseases such as cancers or rheumatoid arthritis. Examples for mAb targeted structures are the soluble protein tumor necrosis factor alpha (TNF-α) for rheumatoid arthritis, Crohn's disease and psoriasis (mAb preparation: Infliximab and Adalimumab), as well as the cell surface proteins CD20 for non-Hodgkin lymphoma (mAb preparation: e.g., Rituximab) and HER2/neu receptor (mAb preparation: Trastuzumab [Herceptin]) for breast cancer.

The generation of monoclonal immunotherapeutically effective antibodies (using hybridoma or phage display techniques and subsequent chimerization and humanization, respectively), however, is time consuming and cost intensive which has prevented a broad clinical application so far. Thus, there is an urgent need to provide a possibility for active vaccination against self-molecules instead of the passive administration of monoclonal antibodies. In contrast to passive immunization, during active vaccination the patient's own immune system is induced to produce antibodies. The induced individualized immune response thus circumvents problems of the monoclonal antibody therapy such as intolerance or non-responsiveness to the therapy.

The active induction of a humoral immune response against self-proteins, however, requires that the immunological self-tolerance is broken. Self-proteins or peptides thereof are only very weekly immunogenic due to the immunological tolerance against self-proteins. Existing immunization strategies based on recombinant proteins or synthetic peptide fragments for induction of antibody responses against self-proteins are thus based on concomitant administration of the antigen in combination with immunostimulatory adjuvants. Many potently effective adjuvants, however, exhibit the disadvantage of undesirable side effects such as toxicity, inflammation reactions, or unwanted systemic T-cell response, and thus, their use should be avoided for active vaccination strategies.

There are certain requirements for an active immunotherapeutically effective vaccination such as breaking self-tolerance against self-proteins, avoidance of adjuvants, antibody specificity against proteins in their native conformation, and induction of antibodies with immune effector functions.

Another essential factor for a successful active vaccination in the context of an antibody-mediated cancer immunotherapy is the selection of an appropriate tumor target structure.

Basic requirements for the target structure are tumor-specificity and cell surface localization. This allows for selective binding of the induced antibodies to the tumor cells and allows for directed exertion of effector functions of the antibody against these cells. Particularly interesting tumor-associated antigens are the so-called cell type specific differentiation antigens. Their expression is limited to cells of a particular specificity and developmental stage in normal tissues. However, in many cancerous diseases, these antigens are expressed in the tumorigenic tissue.

There is an urgent need for the development of means which allow for self-tolerance breaking active immunization without the need of administering adjuvants. In particular, there is a need for the development of means that allow for the generation of antibodies with effector functions, such as antibody-dependent cellular cytotoxicity (ADCC), complement-dependent cytotoxicity (CDC), induction of apoptosis, and inhibition of proliferation, in vivo, wherein said antibodies are directed against a self-protein, such as a tumor-associated antigen.

The present invention relates to the development of vaccines for active vaccination which are able to induce antibodies, in particular autoantibodies, in an organism which bind to self cell membrane surface antigens in their native conformation and subsequently exert therapeutically effective effector functions on cells carrying said cell membrane surface antigens.

The development of cancer immunotherapeutic vaccines is exemplarily described for the target structures claudin 18.2 (CLDN18.2), claudin 6 (CLDN6), and PLAC1, respectively. The generated vaccines are capable of inducing an effective humoral immune response which breaks the present immunological self-tolerance, without concomitant administration of adjuvants. The induced antibodies are further able to recognize the proteins in their native conformation and exert therapeutically relevant effector functions such as ADCC and/or CDC.

SUMMARY OF THE INVENTION

In a one aspect, the present invention provides a protein comprising all or a portion of the amino acid sequence of a hepatitis B virus core antigen protein and inserted therein or attached thereto an amino acid sequence comprising an epitope, wherein the epitope is derived from an extracellular portion of a tumor-associated antigen associated with the surface of a tumor cell. Preferably, the tumor-associated antigen is expressed in a limited number of specific tissues and/or organs under normal conditions and is aberrantly expressed in tumor tissues. In a particularly preferred embodiment, the protein is capable of eliciting a humoral immune response directed against the tumor-associated antigen in association with the surface of a cell when administered in the form of a virus-like particle without adjuvant to a subject, wherein the tumor-associated antigen is a self-protein in said subject. Preferably, the humoral immune response comprises the generation of antibodies which exhibit one or more immune effector functions against cells carrying the tumor-associated antigen in its native conformation, wherein preferably the one or more immune effector functions are selected from the group consisting of complement dependent cytotoxicity (CDC), antibody-dependent cell-mediated cytotoxicity (ADCC), antibody-dependent cell mediated phagocytosis (ADCP), induction of apoptosis, inhibition of CD40L-mediated signal transduction, and inhibition of proliferation. In a preferred embodiment, the immune effector function is activation of effector cells, such as ADCC. In a preferred embodiment, the tumor-associated antigen is a protein of the claudin family or PLAC1, wherein preferably the protein of the claudin family is selected from the group consisting of CLDN18.2 and CLDN6.

In further aspects, the present invention provides a nucleic acid encoding the protein of the present invention and a vector comprising the nucleic acid of the present invention.

In another aspect, the present invention relates to a host cell comprising the nucleic acid or the vector of the present invention.

In a further aspect, the present invention provides a virus-like particle comprising multiple copies of the protein of the present invention. It is particularly preferred that the virus-like particle is capable of eliciting a humoral immune response directed against the tumor-associated antigen in association with the surface of a cell when administered without adjuvant to a subject, wherein the tumor-associated antigen is a self-protein in said subject.

The present invention further provides an immunogenic composition comprising the protein, the nucleic acid, the vector, the host cell, or the virus-like particle of the present invention and a pharmaceutically acceptable diluent, carrier, and/or excipient. Preferably, the immunogenic composition of the present invention is for eliciting a humoral immune response against the tumor-associated antigen in association with the surface of a cell in a subject, wherein the tumor-associated antigen is a self-protein in said subject. It is particularly preferred that the immunogenic composition is free of adjuvants.

In a further aspect, the present invention provides the protein, the nucleic acid, the vector, the host cell, the virus-like particle, or the immunogenic composition of the present invention for prophylactic and/or therapeutic treatment of tumors.

In a further aspect, the present invention provides a method for eliciting a humoral immune response against a tumor-associated antigen in a subject, wherein the tumor-associated antigen is a self-protein in said subject, said method comprising administering to said subject the protein, the nucleic acid, the vector, the host cell, the virus-like particle, or the immunogenic composition of the present invention, wherein said subject is afflicted with a tumor or is at risk of developing a tumor, said tumor being characterized by association of the tumor-associated antigen with the surface of a tumor cell.

In another aspect, the present invention provides a method for breaking self-tolerance towards a tumor-associated antigen in a subject, said method comprising administering to said subject the protein, the nucleic acid, the vector, the host cell, the virus-like particle, or the immunogenic composition of the present invention, preferably without adjuvants.

In another aspect, the present invention provides a method for treating and/or preventing a tumor in a subject, said method comprising administering to said subject the protein, the nucleic acid, the vector, the host cell, the virus-like particle, or the immunogenic composition of the present invention, preferably without adjuvants.

The fusion proteins consist of an amino-terminally and carboxy-terminally localized region of the HBcAg protein, wherein in all of the HBcAg backbones parts of the major immunodominant region (MIR) of HBcAg may be replaced by specific antigen epitopes (epitope). For increasing the flexibility during assembly into VLPs and an increased variance of epitope conformations the epitope inserted into the MIR may be flanked by glycine linkers ($G_4SG_4$; SEQ ID NO: 24). All constructs with the exception of HBcAg Del 79-80 linker and HBcAg Del 79-80 carry restriction sites SalI and SpeI for additional insertion of epitopes at the amino-terminus of HBcAg. At the carboxy-terminus of the constructs a His-tag (black box) consisting of six histidines has been incorporated for purification under denaturing conditions. The His-tag is separated from the HBcAg carboxy-terminus by a short linker (amino acid sequence GGS). The available restriction sites for cloning and modification purposes are indicated.

Figure 2:
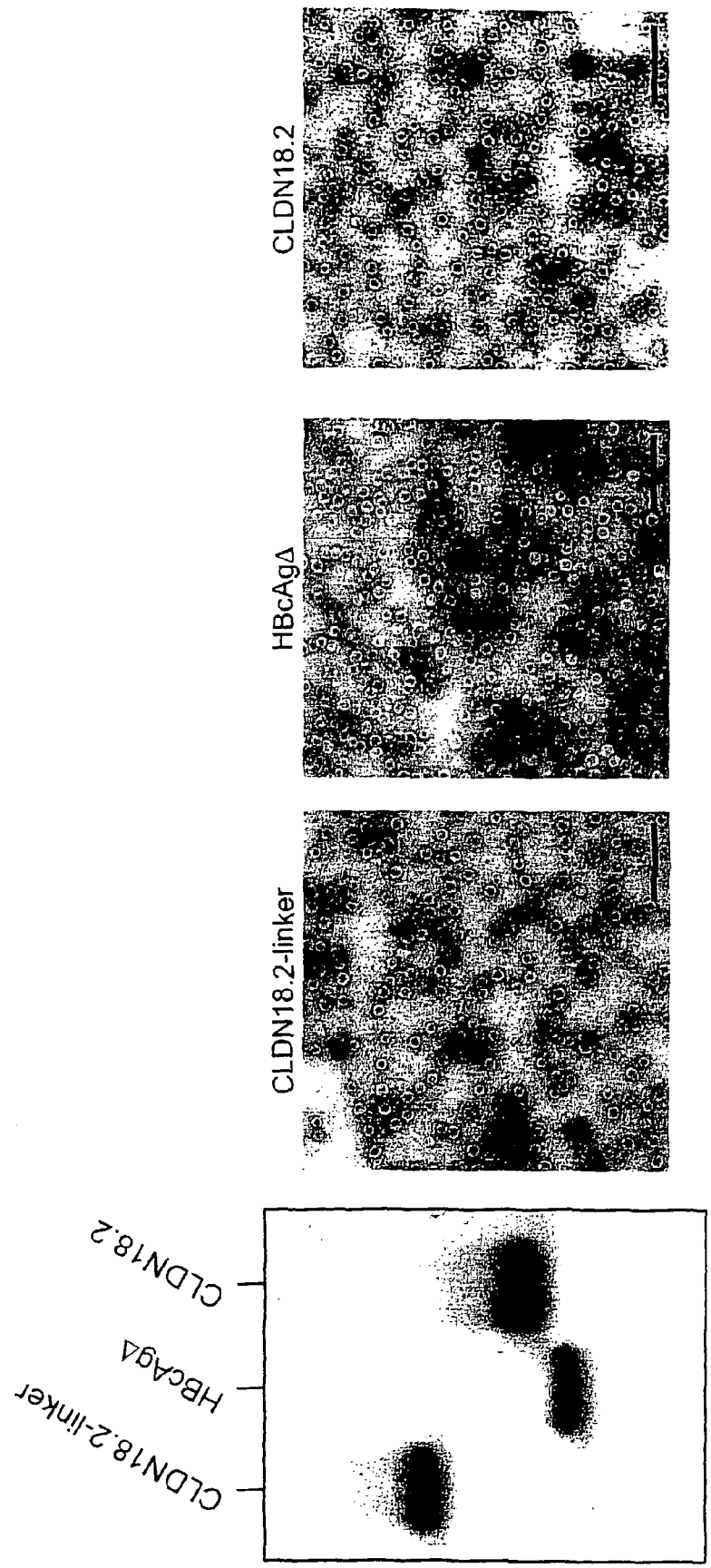

FIG. 2: Validation of the Assembly Competence for Selected HBcAg Fusion Proteins.

In vitro assembled and purified HBcAg VLPs have been analyzed using native agarose gel electrophoresis or negative contrast transmission electron microscopy (TEM). The analysis is exemplarily shown for the chimeric HBcAg VLPs HBcAg Del 79-80 linker CLDN18.2-EC1 short (CLDN18.2-linker), HBcAg Del 79-80 CLDN18.2-EC1 short (CLDN18.2), and the truncated variant of HBcAg wild-type (HBcAgΔ; SEQ ID NO: 79) as control. The indicated black bar within the TEM images corresponds to a length of 200 nm.

FIG. 3: Indirect Immunofluorescence Analysis for Determination of the Immunoreactivity of the Antisera after Immunization of Balb/c Mice or NZW Rabbits.

A) Chinese hamster ovary cells (CHO cells, ATCC No. CCL-61) have been co-transfected with eGFP-N3 (GFPmut1 variant) in combination with rabbit or mouse CLDN18.2 and CLDN18.1, respectively, incubated for 24 hours, subsequently fixed with 4% paraformaldehyde (PFA) and afterwards permeabilized with 0.2% saponin. Incubation with diluted (1:100) polyclonal rabbit serum 5 (Immunogen used for the generation of rabbit serum #5: HBcAg Del 79-80 linker CLDN18.2-EC1 short VLPs+Freund's adjuvants) was carried out for one hour. A CY3-conjugated goat-anti-rabbit IgG(H+L) monoclonal antibody has been used as secondary antibody at a dilution of 1:200 and has been added for 30 minutes. DAPI at a dilution of 1:10000 has been used for staining the cell nuclei. B) The IF analysis has been performed as described under A). For the detection of CLDN18.2 the diluted (1:100) polyclonal mouse antiserum 1/4 (Immunogen used for the generation of antiserum 1/4: HBcAg Del 79-80 linker CLDN18.2-EC1 short VLPs without adjuvants) has been used. A CY3-conjugated goat-anti-mouse IgG(H+L) monoclonal antibody has been used as secondary antibody at a dilution of 1:200. C) CHO cells have been co-transfected with eGFP-TES85 (localized within the cell nucleus) and human PLAC1 and have been fixed with 4% PFA after 24 hours of cultivation. The diluted (1:500) rabbit antiserum PLAC1 #9 has been used as the polyclonal antiserum for detection of PLAC1 (Immunogen used for the generation of antiserum PLAC1 #9: HBcAg Del 79-80 linker PLAC1 $3^{rd}$ Loop A VLPs+Freund's adjuvants) and PLAC1 #10 (Immunogen used for the generation or antiserum PLAC1 #10: HBcAg Del 79-80 linker PLAC1 $3^{rd}$ Loop A VLPs without adjuvants), respectively. A CY3-conjugated goat-anti-rabbit IgG(H+L) monoclonal antibody has been used as a secondary antibody at a dilution of 1:200.

Figure 4:
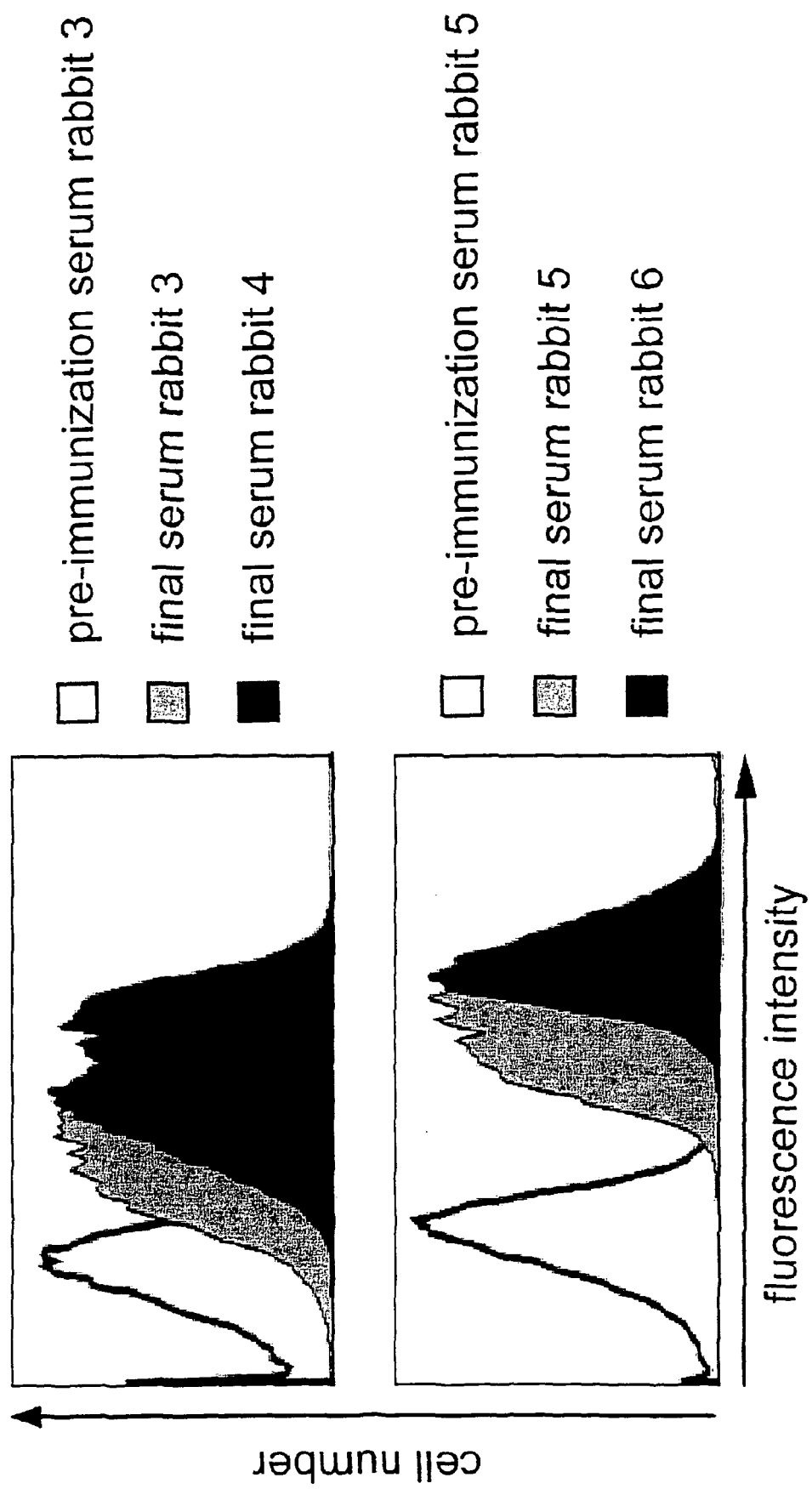

FIG. 4: FACS Analysis of the Immunoreactivity of Rabbit Antisera after Immunization with Human CLDN18.2 Epitope Carrying Chimeric HBcAg VLPs.

$1\times10^5$ NUG-C4 cells endogenously expressing human CLDN18.2 (hsCLDN18.2) have been used for FACS analysis. The cells have been incubated for one hour with diluted (1:50) rabbit serum. After a washing step, incubation with a diluted (1:100) Alexa647-labeled goat-anti-rabbit IgG(H+L) monoclonal secondary antibody for half an hour has been carried out. The histogram overlays of the fluorescent signals for rabbit pre-immunization serum (white) and final sera (gray and black, respectively) are shown. All of the rabbits have been immunized with HBcAg Del 79-80 linker CLDN18.2-EC1 short VLPs. Rabbit 3 has been immunized without addition of adjuvants, whereas rabbits 4 and 5 have been administered Freund's adjuvant and rabbit 6 has been administered the adjuvant Montanide ISA 720 which has been approved for clinical applications.

Figure 5A:
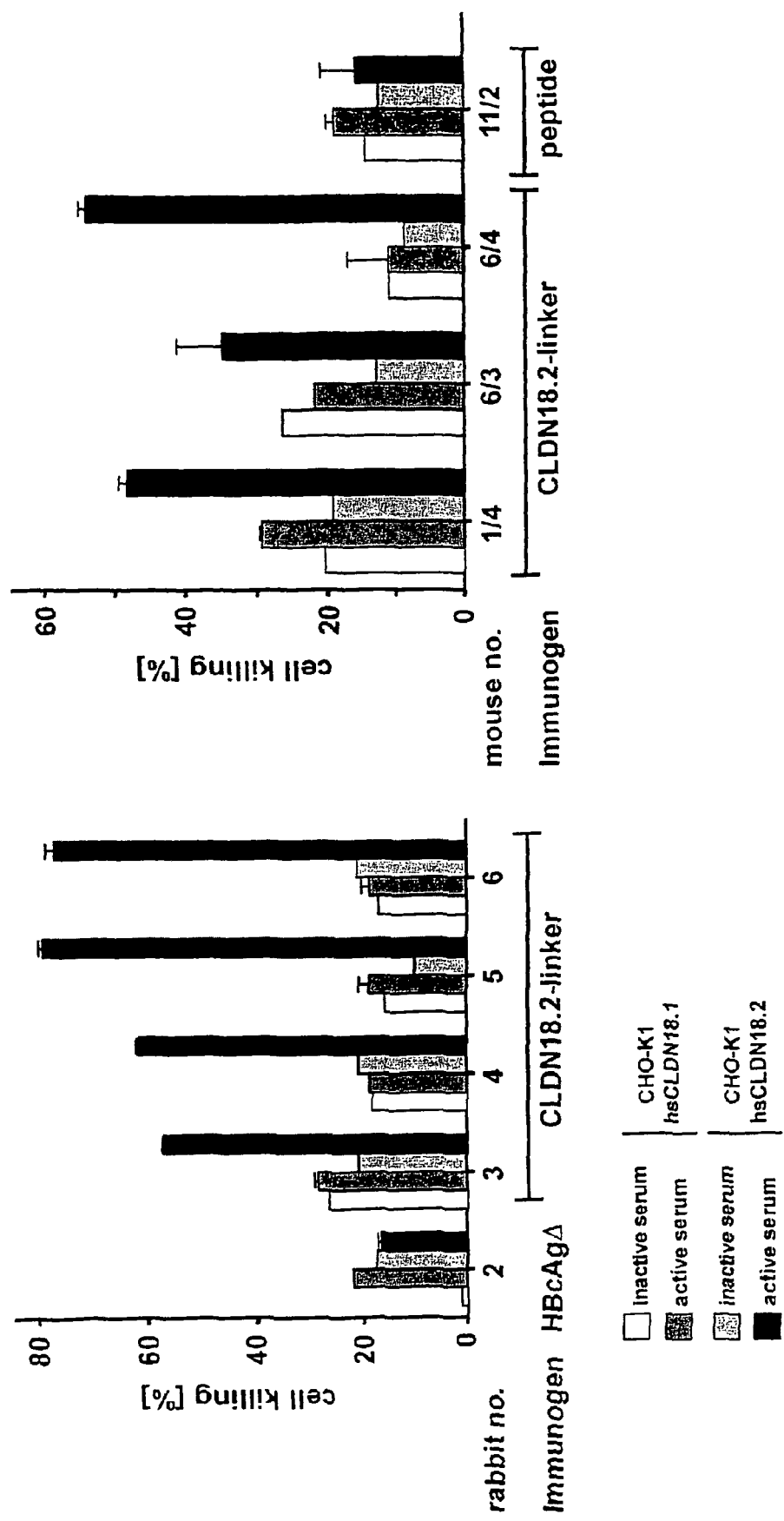
Figure 5B:
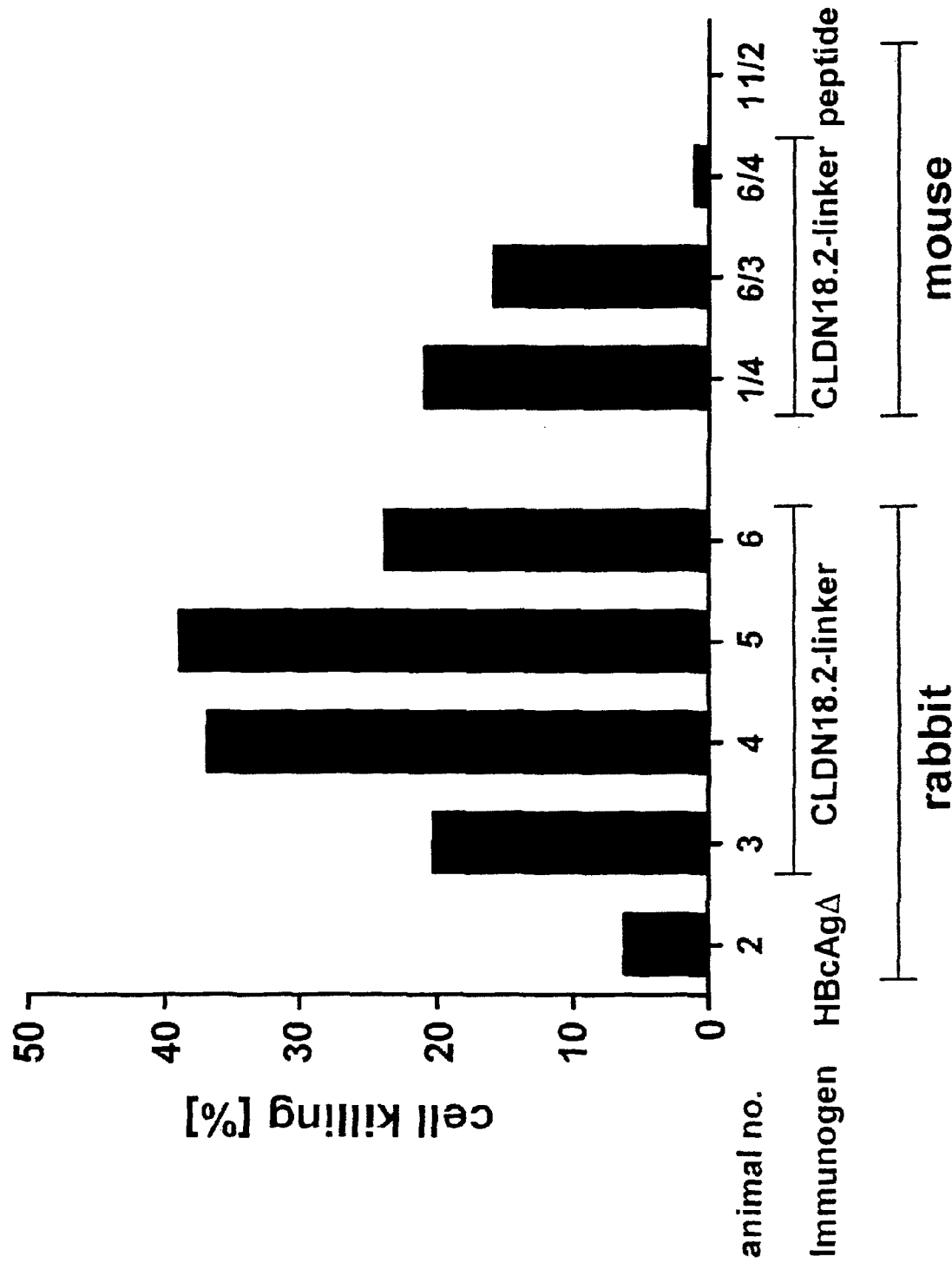

FIG. 5: Analysis of the Cytotoxic Effector Functions of the CLDN18.2 Directed Polyclonal Antisera after Active Immunization.

A) Luciferase based CDC assay. CHO cells stably expressing human CLDN18.2 (hsCLDN18.2) or the isoform claudin 18.1 (hsCLDN18.1) have been transfected with in vitro transcribed (IVT) RNA coding for luciferase 24 hours before the assay. Subsequently, the cells have been incubated for 30 minutes with the indicated polyclonal antisera before active or heat-inactivated human serum has been added for 30 minutes. After addition of a luciferase containing buffer, the percentage of killed cells has been calculated (after subtraction of background luminescence and in comparison to cells which have been incubated with active serum but without addition of antiserum). B) Luciferase based ADCC assay. One day before the assay, NUG-C4 cells endogenously expressing hsCLDN18.2 have been transfected with luciferase IVT-RNA. Subsequently, the cells have been incubated with the indicated polyclonal antisera for 30 minutes before isolated human Peripheral Blood Mononuclear Cells (PBMC) as effector cells have been added. After 5 hour incubation, a luciferin-containing buffer has been added and the percentage of killed cells has been calculated (after subtraction of the background luminescence and in comparison to cells which have been incubated with PBMCs but without addition of antiserum). The rabbits 3 to 6 as well as the mice 1/4, 6/3, and 6/4 have been immunized with HBcAg Del 79-80 linker CLDN18.2-EC1 short VLPs (CLDN18.2-Linker). Rabbit 3 and mouse 1/4 received the immunogen without addition of adjuvants, whereas rabbits 4 and 5 received Freund's adjuvant, rabbit 6 Montanide ISA 720, and mice 6/3 and 6/4 Abisco100. The antisera of rabbit 2 which has been immunized with C-terminally truncated HBcAg wild-type VLPs (HBcAgΔ), and of mouse 11/2 which has been administered a KLH-conjugated peptide of CLDN18.2 which sequence was identical to the epitope inserted into HBcAg, have been used as controls.

FIG. 6: Analysis of the Anti-Proliferative Effector Functions of the PLAC1 Directed Polyclonal Antisera after Active Immunization.

A) Inhibition of proliferation of PLAC1 expressing human breast cancer epithelium MCF-7 cells (ATCC No. HTB-22). 5000 cells per well have been plated in 10% FCS-containing medium and incubated for 72 hours with diluted (1:100 or 1:1000) polyclonal PLAC1-directed antisera. Subsequently, a BrdU-based proliferation assay using the Delfia cell proliferation kit has been carried out. The proliferation rate (in %) has been calculated with respect to a medium control (=100%). A polyclonal anti-CLDN18.2 antiserum which has been generated by active immunization (anti-CLDN18.2) as well as a monoclonal anti-myc antibody have been used as control sera. B) No inhibition of proliferation of PLAC1-negative MelHO cells. The procedure has been carried out as described under A). HBcAg Del 79-80 linker PLAC1 $3^{rd}$ Loop A (serum #9 with adjuvants, serum #10 without adjuvants) as well as HBcAg Del 79-80 PLAC1 $3^{rd}$ Loop B (serum #11 with adjuvants) have been used as immunogens for active anti-PLAC1 immunization.

FIG. 7: Sequences of the HBcAg Backbones.

The nucleic acid and amino acid sequences of the various HBcAg backbones are shown in one-letter-code. The numbering of the sequence is indicated left and right, respectively, of the sequence. ☐ indicates the amino-terminal and carboxy-terminal HBcAg domains, respectively; ▨ indicates inserted glycine linkers (italics, bold) and ▨ indicates the carboxy-terminally localized His-tag (bold).

FIG. 8: Sequences of the Chimeric HBcAg Expression Constructs which have been Used for the Generation of Epitope Carrying VLPs.

Nucleic acid and amino acid sequences of the various chimeric HBcAg expression constructs are shown in one-letter-code. The numbering of the sequence is indicated left and right, respectively, of the sequence. ☐ indicates the amino-terminal and carboxy-terminal HBcAg domains, respectively; ▨ indicates inserted glycine linkers (italics, bold) and ▨ indicates the carboxy-terminally localized His-tag (bold). The amino acid sequences of the inserted CLDN18.2 and PLAC1 epitopes, respectively, are depicted in bold and are underlined.

FIG. 9: Prophylactic Vaccination with CLDN18.2 Epitope Carrying Chimeric HBcAg VLPs (HBcAg Del 79-80 Linker CLDN18.2-EC1 Short-VLPs) Confers Partial Protection in an Immunocompetent Syngeneic Mouse Tumor Model Macroscopic analysis of lungs derived from mice vaccinated with HBcAg Del 79-80 linker CLDN18.2-EC1 short-VLPs (CLDN-Link) revealed a smaller number of metastatic nodules as compared to HBcAg-VLPs comprising a C-terminally truncated protein (amino acids 1-150) (HBcAgΔ) or PBS control groups (A) and significantly lower lung weights close to those of mice not challenged with tumor cells (B). The percentage of cancerous tissue area per whole lung section as calculated after visualizing CT26-CLDN18.2 pulmonary metastases by IHC-staining for CLDN18.2 was significantly (p<0.05) smaller as compared to mice vaccinated with HBcAgΔ-VLPs or PBS control groups (C, D).

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment the protein of the present invention comprises a linker sequence flanking the epitope sequence and in another preferred embodiment the protein of the present invention comprises a peptide tag, it is a contemplated preferred embodiment of the protein of the present invention that the protein comprises a linker sequence flanking the epitope sequence and a peptide tag.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

DEFINITIONS

In the following, definitions will be provided which apply to all aspects of the present invention.

Hepatitis B virus (HBV) is a member of the Hepadnavirus family. The virus particle consists of an outer lipid envelope and an icosahedral nucleocapsid core composed of the hepatitis B virus core antigen protein. The genome of HBV is made of circular DNA. There are four known genes encoded by the genome called C, X, P, and S. The core protein is coded for by gene C and its start codon is preceded by an upstream in-frame AUG start codon from which the pre-core protein is produced. The protein encoded by gene C is present in at least four different functionally relevant HBV polypeptides: p25 (preC protein), p22 (N-terminally cleaved form of the p25), p21 (HBcAg monomer as such), and p17 (HBeAg, N- and C-terminally cleaved form of p25). Of these polypeptides only the HBcAg monomer is able to self-assemble into a virus-like particle. Such virus-like particles may contain 180 or 240 copies of the HBcAg protein and may be around 30 nm or 34 nm in diameter. The HBcAg protein comprises an N-terminal region which is able to self-assemble into virus-like particles. The C-terminal limit for C-terminal truncations which are still able to self-assemble into HBcAg particles was mapped between amino acid residues 139 and 144. The C-terminal protamine-like arginine-rich domain corresponding to amino acids 150 to 183 is dispensable for self-assembly. Its function is the binding of nucleic acids. The so called major immunodominant region (MIR) is localized within a superficial loop around amino acid residues 74 to 89 of the HBcAg protein.

The term "hepatitis B virus core antigen protein" or "HBcAg protein" in the context of the present invention relates to the polypeptide p21 of any virus belonging to the Hepadnaviridae family, preferably to the hepatitis B virus polypeptide p21 of any hepatitis B virus serotype, such as the serotypes adr, adw, ayr, and ayw, or genotype, such as the genotypes A, B, C, D, E, F, G, and H. Preferably the hepatitis B virus polypeptide p21 is derived from the hepatitis B virus serotype ayw. Preferably, the HBcAg protein comprises, preferably essentially consists of, preferably consists of the amino acid sequence set forth in SEQ ID NO: 1, a variant or portion thereof. The nucleic acid sequence set forth in SEQ ID NO: 2 codes for the amino acid sequence set forth in SEQ ID NO: 1. In the context of the present invention, the term "hepatitis B virus core antigen protein" or "HBcAg protein" includes any variants and/or portions thereof, wherein preferably said variants and/or portions thereof are able to assemble into virus-like particles, preferably into an icosahedral virus-like particle, preferably consisting of 180 or 240 copies of HBcAg subunits. Although the C gene is the most conserved amongst the HBV genes, numerous amino acid substitutions have been identified for the HBcAg protein. Thus, the term "hepatitis B virus core antigen protein variant" includes, in particular, any of the naturally occurring variants of the HBcAg protein. Said term also includes any synthetically generated variants which are not naturally occurring and are able to assemble into virus-like particles.

The term "virus-like particle" or "VLP" refers to an empty virus capsid, which is formed by self-assembly of envelope and/or capsid proteins from many viruses, including HIV-1, rubella virus, human papilloma virus, Semliki Forest virus, RNA phages, and Hepadnaviridae such as hepatitis B virus. The virus-like particles resemble the virus from which they were derived, but lack any viral nucleic acid and therefore, are not infectious. The virus-like particles of the present invention comprise chimeric hepatitis B virus core antigen proteins. The virus-like particles of the invention are non-infectious because they assemble without incorporating genetic material. The term "chimeric hepatitis B virus core antigen protein" refers to a protein that comprises a hepatitis B virus core antigen protein or a portion thereof and an amino acid sequence derived from a protein other than a hepatitis B virus core antigen protein, such as an amino acid sequence comprising an epitope which is derived from a tumor-associated antigen. In a preferred embodiment of the present invention, the virus-like particle comprises a HBcAg protein derived from a hepatitis B virus as a carrier for the integration of heterologous epitopes. However, HBcAg genes from any other Orthohepadnavirus or Avihepadnavirus can also be used.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence. The term "part" refers to a continuous element. For example, a part of a structure such as an amino acid sequence or protein refers to a continuous element of said structure. A portion or a part of a structure preferably comprises one or more functional properties of said structure. For example, a portion or a part of an epitope is preferably immunologically equivalent to the epitope it is derived from.

The term "portion thereof" in the context of the HBcAg protein refers to a portion of the HBcAg protein which comprises at least 30, preferably 50, more preferably 80, more preferably 90, more preferably 100, even more preferably 110, even more preferably 120, even more preferably 130 or more amino acids of the HBcAg protein. The term "portion" also includes a discontinuous portion of the amino acid sequence of the HBcAg protein. For example, a HBcAg portion of 138 amino acids may consist of amino acids 1 to 75 and 82 to 144 of the HBcAg protein as set forth in SEQ ID NO: 1 or amino acids corresponding to said amino acids of SEQ ID NO: 1. It is preferred that the discontinuity lies within the region corresponding to the MIR, e.g., the region around amino acids 74 to 89 of the HBcAg protein. It is preferred that the portion of HBcAg is able to assemble into virus-like particles. In the case of a discontinuous portion of the HBcAg protein it is preferred that said discontinuous portion is able to assemble into virus-like particles, if the parts of the discontinuous portion are joined together in their natural order. This attachment may be direct or by a linker, for example, by an amino acid sequence comprising an epitope sequence.

The phrase "the protein is able to assemble into virus-like particles" or similar formulations mean that a plurality of the protein (and not just a single copy of the protein) is able to assemble into virus-like particles. In this context, the assembled virus-like particle does not necessarily have to assume the native HBcAg virus-like particle structure, i.e., having 180 or 240 subunits in an icosahedral shape, but any structure that is similar to any virus-like particle structure, for example, a virus-like particle composed of 30, 50, 70, 90, or 150 subunits that may, for example, exhibit an irregular shape, as long as the virus-like particle is stable to a reasonable extend. For example, the virus-like particle should be stable enough to be formulated into a pharmaceutical composition and to be administered to a patient. The skilled person can readily determine whether a protein is able to assemble into virus-like particles. For example, the protein may be expressed in a heterologous expression system. The assembly of the virus-like particles occurs within the cytoplasm of the expression host. The cells are harvested, for example, by tangential flow filtration, and lyzed, e.g., using a microfluidizer. The cell debris is removed and the soluble lysate is assayed for the presence of virus-like particles. For example, the virus-like particles may be concentrated and pre-purified by ultrafiltration, hydrophobic interaction, hydroxyapatite or sepharose blue chromatography. The virus-like particles may further be purified by anion exchange chromatography, size exclusion chromatography and/or ultrafiltration. The concentrated and purified virus-like particles may then be detected by negative staining transmission electron microscopy, native agarose gel electrophoresis, asymmetric flow-field-flow fractionation (AF4) combined with dynamic light scattering (DLS), and/or capture ELISA using a conformation specific monoclonal antibody.

Figure 1:
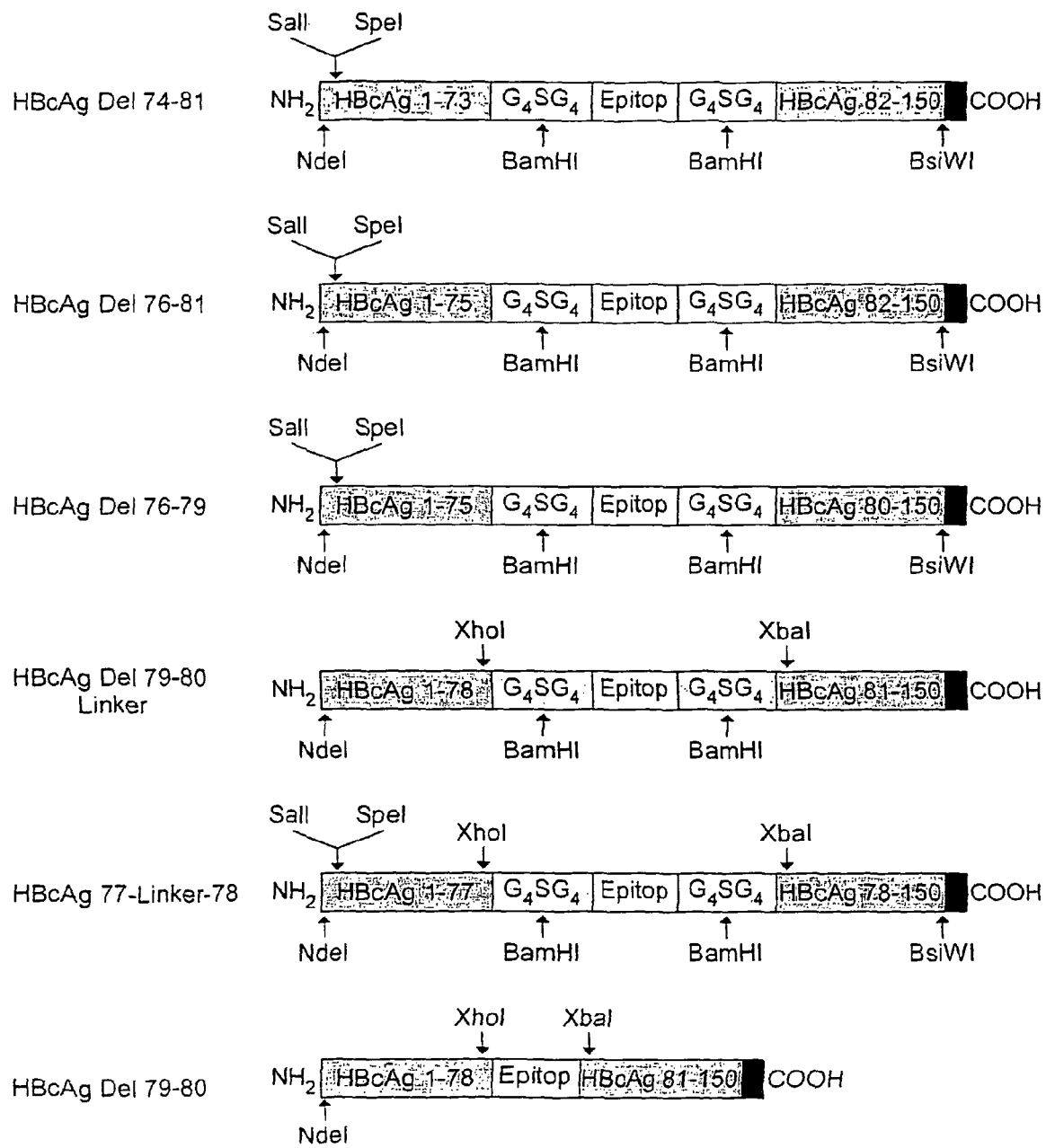
FIG. 1: Schematic Representation of the HBcAg Expression Cassettes (HBcAg Backbones).

An amino acid sequence (first amino acid sequence) "inserted into" another amino acid sequence (second amino acid sequence) or an amino acid sequence "inserted therein" means that the first amino acid sequence is integrated into the second amino acid sequence in between two amino acids of the primary structure of the second amino acid sequence. Preferably, the first and the second amino acid sequences are connected by peptide bonds. One example of an inserted amino acid sequence in the context of the present invention is the insertion of an epitope sequence, for example, derived from a tumor-associated antigen, between two amino acids within the MIR of the HBcAg protein and/or between two amino acids within the N-terminus of the HBcAg protein as shown in FIG. 1, e.g., between the SalI and SpeI restriction sites. In the context of the present invention, a first amino acid sequence inserted into a second amino acid sequence may also mean that the first amino acid sequence replaces one or more, such as 1, 2, 3, 4, 5, 6, 7, 8, 9, 10 or more, amino acids of the second amino acid sequence.

An amino acid sequence (first amino acid sequence) is meant to be "attached to" another amino acid sequence (second amino acid sequence) if the first amino acid sequence is attached to any amino acid of the second amino acid sequence, for example, by chemical cross-linking or a peptide bond. If an amino acid sequence is connected to the amino-terminal or the carboxy-terminal amino acid of the second amino acid sequence it is attached to the second amino acid sequence. A variety of cross linkers are commercially available from major suppliers such as Pierce, Molecular Probes, and Sigma. Homo-bifunctional reagents, specifically reacting with primary amine groups (i.e., ε-amino groups of lysine residues) may be used. They are soluble in aqueous solvents and can form covalent bond. Furthermore, homo-bifunctional imidoesters with varying lengths of spacer arms between their reactive end groups, such as dimethyl adipimidate (DMA), dimethyl suberimidate (DMS), and dimethyl pimelimidate (DPM) with spacer arm of, for example, 8.6 Å, 11 Å, or 9.2 Å may be used. Furthermore, also reversible homobifunctional cross linkers may be used such as N-hydroxysuccinimide (NHS) esters, such as dithiobis(succinimidylpropionate) (DSP) or dithiobis(sulfosuccinimidylpropionate) DTSSP. Alternatively, a heterobifunctional cross linker may be used, for example, a cross linker with one amine-reactive end and a sulfhydryl-reactive moiety at the other. For example, hetero-bifunctional cross linkers with an NHS ester at one end and an SH-reactive groups, such as meleimides or pyridyl disulfides, can be used. Hetero-bifunctional reagents containing a photoreactive group, such as Bis[2-(4-azidosalicylamido)ethyl)] disulfide BASED, may also be used.

An amino acid sequence (first amino acid sequence) is meant to "replace" (an) amino acid(s) or another amino acid sequence (second amino acid sequence) if the amino acid(s) or the second amino acid sequence is (are) removed completely and instead the first amino acid sequence is placed at the position where the amino acid(s) or the second amino acid sequence was (were) located.

Residues in two or more polypeptides are said to "correspond" to each other if the residues occupy an analogous position in the polypeptide structures. As is well known in the art, analogous positions in two or more polypeptides can be determined by aligning the polypeptide sequences based on amino acid sequence or structural similarities. Such alignment tools are well known to the person skilled in the art and can be, for example, obtained on the World Wide Web, e.g., ClustalW (www.ebi.ac.uk/clustalw) or Align (http://www.ebi.ac.uk/emboss/align/index.html) using standard settings, preferably for Align EMBOSS::needle, Matrix: Blosum62, Gap Open 10.0, Gap Extend 0.5. Those skilled in the art understand that it may be necessary to introduce gaps in either sequence to produce a satisfactory alignment. Residues in two or more polypeptide sequences are said to "correspond" if the residues are aligned in the best sequence alignment. The "best sequence alignment" between two polypeptides is defined as the alignment that produces the largest number of aligned identical residues. The "region of best sequence alignment" ends and, thus, determines the metes and bounds of the length of the comparison sequence for the purpose of the determination of the similarity score, if the sequence similarity, preferably identity, between two aligned sequences drops to less than 30%, preferably less than 20%, more preferably less than 10% over a length of 10, 20, or 30 amino acids.

For the purposes of the present invention, "variants" of a protein or peptide or of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids. For example, in the context of the present invention, a HBcAg protein comprising a carboxy-terminally fused peptide tag such as a His-tag is considered a HBcAg addition variant.

Amino acid deletion variants are characterized by the removal of one or more amino acids from the sequence, such as by removal of 1, 2, 3, 5, 10, 20, 30, 50, or more amino acids. The deletions may be in any position of the protein. In the context of the HBcAg protein used in the present invention, a preferred amino acid deletion variant of HBcAg is a deletion within the MIR region, e.g., within the amino acids around positions 74 to 89 of SEQ ID NO: 1 or corresponding amino acids. It is also preferred in the context of the present invention that the HBcAg protein is C-terminally truncated, i.e., has a C-terminal deletion/truncation. Preferably, said C-terminal truncation extends from the C-terminus to and including any amino acid down to the amino acid at position 140 in the amino acid sequence as set forth in SEQ ID NO: 1 or a corresponding amino acid sequence. A C-terminal truncation of a protein at amino acid position 140 means that the amino acids at position 140 to the C-terminus of the full-length protein are missing in the C-terminally truncated protein, i.e., that the C-terminally truncated protein ends with amino acid 139 (including amino acid 139).

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence, e.g., between the preferred HBcAg sequence set forth in SEQ ID NO: 1 and the HBcAg variant or between the preferred tumor-associated antigen sequences, for example, set forth in SEQ ID NOs: and the tumor-associated antigen variants, will be at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%. The degree of similarity or identity is given preferably for a region of at least about 20, at least about 40, at least about 60, at least about 80, at least about 100, at least about 120, at least about 140 or 160 amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5. It is to be understood that in preferred embodiments the HBcAg variant is a deletion variant and/or a truncation variant, for example, carrying a deletion within the MIR or a truncation at the carboxy-terminus. Furthermore, in particularly preferred embodiments the variants are naturally occurring variants. Preferred examples of the HBcAg protein variants, if SEQ ID NO: 1 is used as reference sequence, comprise mutations at one or more of positions.

The proteins and nucleic acid sequences of the present invention also comprise variants of the proteins of the present invention and of the nucleic acid sequences of the present invention. The above definition for protein variants also applies correspondingly to nucleic acid sequence variants.

The protein and nucleic acid sequence variants described herein may be readily be prepared by the skilled person, for example, by recombinant DNA manipulation. The manipulation of DNA sequences for preparing proteins and peptides having substitutions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The proteins and peptides described herein may be derivatives of proteins and peptides. According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. The term "derivative" also extends to all functional chemical equivalents of said proteins and peptides. Preferably, a modified peptide, i.e., a derivative peptide, exhibits increased stability and/or increased immunogenicity.

According to the invention, a variant, derivative, portion, part, or fragment of a peptide or protein or of a nucleic acid or amino acid sequence preferably has a functional property of the peptide or protein or the nucleic acid or amino acid sequence, respectively, from which it has been derived. Such functional properties comprise immunological properties such as the interaction with antibodies, the interaction with other peptides or proteins, and the assembly into virus-like particles.

The term "immunologically equivalent" means that the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the chimeric HBcAg protein of the invention, the term "immunologically equivalent" is preferably used with respect to the immunological effects or properties of the epitope derived from a tumor-associated antigen which is comprised by the chimeric HBcAg protein. A particular immunological property is the ability to bind to antibodies and, where appropriate, generate an immune response, preferably by stimulating the generation of antibodies. For example, an amino acid sequence is immunologically equivalent to a reference amino acid sequence if said amino acid sequence when exposed to the immune system of a subject induces an immune reaction, preferably antibodies, having a specificity of reacting with the reference amino acid sequence, such as the reference amino acid sequence forming part of a tumor-associated antigen.

In the context of the present invention, the terms "tumor-associated antigen" or "tumor antigen" relate to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor tissues. In this context, "a limited number" preferably means not more than 3, more preferably not more than 2. The expression of tumor-associated antigens is reactivated in tumor tissues irrespective of the origin of the tumor, i.e., the tissue or organ the tumor is originated/derived from. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a tumor cell and is preferably not or only rarely expressed in normal tissues. Preferably, the tumor-associated antigen or the aberrant expression of the tumor-associated antigen identifies tumor cells, preferably cancerous cells. In the context of the present invention, the tumor-associated antigen that is expressed by a tumor cell in a subject, e.g., a patient suffering from a tumorigenic disease, is preferably a self-protein in said subject. In preferred embodiments, no autoantibodies directed against the tumor-associated antigen can be found in a detectable level under normal conditions in a subject carrying said tumor-associated antigen or such autoantibodies can only be found in an amount below a threshold concentration that would be necessary to cause damage to the tissue or cells carrying said tumor-associated antigen. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in tumorigenic tissues. In the context of the present invention, the tumor-associated antigen is preferably not a product of a mutated tumor suppressor gene or a mutated oncogene or of any other mutated gene, unless this mutation is present in the germ line of the subject expressing said tumor-associated antigen. In the context of the present invention, the tumor-associated antigen is preferably not a tumor antigen produced by an oncogenic virus.

Examples for differentiation antigens which ideally fulfill the criteria for tumor-associated antigens as contemplated by the present invention as target structures in tumor immunotherapy, in particular, in tumor vaccination are the cell surface proteins of the claudin family, such as CLDN6 and CLDN18.2, and PLAC1. CLDN18.2 is selectively expressed in normal tissues in differentiated epithelial cells of the gastric mucosa, whereas CLDN6 and PLAC1 have been described as placenta-specific expression product. These differentiation antigens are expressed in tumors of various origins as described herein below, and are particularly suited as target structures for the development of active vaccination strategies in connection with antibody-mediated cancer immunotherapy due to their selective expression (no expression in a toxicity relevant normal tissue) and localization to the plasma membrane.

The terms "normal tissue" or "normal conditions" refer to healthy tissue or the conditions in a healthy subject, i.e., non-pathological conditions, wherein "healthy" preferably means non-tumorigenic or non-cancerous.

The term "specifically expressed" means that a protein is essentially only expressed in a specific tissue or organ. For example, a tumor-associated antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, the tumor-associated antigen may also be specifically expressed under normal conditions in more than one tissue type or organ, such as in 2 or 3 tissue types or organs, but preferably in not more than 3 different tissue or organ types. In this case, the tumor-associated antigen is then specifically expressed in these organs. For example, if a tumor-associated antigen is expressed under normal conditions preferably to an approximately equal extent in lung and stomach, said tumor-associated antigen is specifically expressed in lung and stomach.

The term "self-protein" in relation to a particular subject in the context of the present invention means a protein that is encoded by the genome of said subject and that is under normal conditions, i.e., non-pathological conditions, optionally expressed in certain normal tissue types or at certain developmental stages of said subject. Preferably, it does not include proteins with acquired mutations. A tumor-associated antigen that is a self-protein in a subject includes a tumor-associated antigen that is or was expressed in said subject under normal conditions in certain tissues or at a certain developmental stage and is abnormally or aberrantly expressed in tumorigenic tissue of said subject, preferably in the same form and/or with the same structure. An "autoantibody" is an antibody that reacts with the cells, tissues, or native proteins of the individual in which it is produced, i.e., which reacts with self-proteins of said individual.

The term "self tolerance" designates a mechanism, where the body does not mount an immune response to self proteins. Normally, self-tolerance is developed early by developmental events within the immune system that prevent, in particular, the organism's own T cells and B cells from reacting with the organism's own tissues.

The term "an extracellular portion of a tumor-associated antigen" in the context of the present invention refers to a part of a tumor-associated antigen facing the extracellular space of a cell preferably being accessible from the outside of said cell, e.g., by antibodies located outside the cell. Preferably, the term refers to an extracellular loop or a part thereof or any other extracellular part of a tumor-associated antigen which is preferably specific for said tumor-associated antigen. Preferably, said part comprises at least 5, at least 8, at least 10, at least 15, at least 20, at least 30, or at least 50 amino acids or more.

The term "tumor-associated antigen associated with the surface of a cell" means that the tumor-associated antigen is associated with and located at the plasma membrane of said cell, wherein at least a part of the tumor-associated antigen faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a tumor-associated antigen associated with the surface of a cell may be a transmembrane protein having an extracellular portion or may be a protein associated with the surface of a cell by interacting with another protein that is a transmembrane protein.

The term "epitope derived from a tumor-associated antigen", means, for example, an epitope that is a portion or a part of the tumor-associated antigen, preferably a portion or a part of the tumor-associated antigen which is specific for the tumor-associated antigen, or a variant or derivative thereof, preferably a variant or derivative thereof which is immunologically equivalent. Preferably, it is possible to identify the tumor-associated antigen from which the epitope is derived based on the epitope sequence. In the context of the term "a tumor derived from a specific tissue" the term "derived from" means "originated from".

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant, or malignant.

Preferably, a tumor disease according to the invention is a cancer disease, i.e., a malignant disease, and a tumor cell is a cancer cell. Preferably, a tumor disease is characterized by cells in which an antigen, i.e., a tumor-associated antigen, preferably a tumor-associated antigen as defined above, is expressed or aberrantly expressed. Preferably, a tumor disease or a tumor cell is characterized by surface expression of a tumor-associated antigen. In a preferred embodiment of the present invention, the tumor or cancer cell is identifiable by a cell surface associated tumor-associated antigen, such as by CLDN6, CLDN18.2, or PLAC1.

"Aberrant expression" or "abnormal expression" means according to the invention that expression is altered, preferably increased, compared to the state in a non-tumorigenic normal cell or a healthy individual, i.e., in an individual not having a disease associated with aberrant or abnormal expression of a certain protein, e.g., a tumor-associated antigen. An increase in expression refers to an increase by at least 10%, in particular at least 20%, at least 50% or at least 100%, or more. In one embodiment, expression is only found in a diseased tissue, while expression in a healthy tissue is repressed.

Preferably, a tumor disease according to the invention is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer, and lung cancer, and the metastases thereof. Examples thereof are lung carcinomas, mamma carcinomas, prostate carcinomas, colon carcinomas, renal cell carcinomas, cervical carcinomas, or metastases of the cancer types or tumors described above. The term "cancer" according to the invention also comprises cancer metastases.

Preferred tumor-associated antigens in the context of the present invention are proteins of the claudin family, preferably CLDN6 or CLDN18.2, or PLAC1.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop, termed EC1 or ECL1, consists on average of 53 amino acids, and the second extracellular loop, termed EC2 or ECL2, consists of around 24 amino acids. In the context of the present invention, the preferred claudins are CLDN6 (SEQ ID NOs: 3 and 4) and CLDN18.2 (SEQ ID NOs: 5 and 6). CLDN6 and CLDN18.2 have been identified as differentially expressed in tumor tissues, with the only normal tissues expressing CLDN18.2 being stomach and testis and the only normal tissue expressing CLDN6 being placenta.

For example, CLDN18.2 has been found to be expressed in pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis. The cells expressing CLDN18.2 are preferably cancer cells and are, in particular, selected from the group consisting of tumorigenic gastric, esophageal, pancreatic, lung, ovarian, colon, hepatic, head-neck, and gallbladder cancer cells.

CLDN6 has been found to be expressed, for example, in ovarian cancer, lung cancer, gastric cancer, breast cancer, hepatic cancer, pancreatic cancer, skin cancer, melanomas, head neck cancer, sarcomas, bile duct cancer, renal cell cancer, and urinary bladder cancer. CLDN6 is a particularly preferred target for the prevention and/or treatment of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma, kidney cancer, in particular renal cell carcinoma including clear cell renal cell carcinoma and papillary renal cell carcinoma, colon cancer, testicular embryonal carcinoma, and placental choriocarcinoma, and the metastatic forms thereof. In one embodiment, the cancer disease associated with CLDN6 expression is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma. In one embodiment, the tumor cell associated with CLDN6 expression is a cell of such a cancer.

PLAC1 (SEQ ID NOs: 7 and 8) is a placenta-specific gene which is frequently aberrantly activated and highly expressed in a variety of tumor types, in particular breast cancer. RNAi-mediated silencing of PLAC1 in MCF-7 and BT-549 breast cancer cells profoundly impairs motility, migration, and invasion and induces a G1/S cell cycle block with nearly complete abrogation of proliferation. Knock down of PLAC1 is associated with decreased expression of cyclin D1 and reduced phosphorylation of AKT kinase. Moreover, PLAC1 is localized on the surface of cancer cells and is accessible for antibodies which antagonize biological functions of this molecule.

PLAC1 has several properties that make it a highly attractive target for therapeutic antibodies and/or prophylactic and/or therapeutic vaccination. In the case of breast cancer for example, 82% of patients carry this target. Her2/neu, in contrast, the target of Herceptin, the only monoclonal antibody (mAb) available for treatment of this cancer type, is overexpressed in only 20-25% of breast cancer patients (Slamon, D. J., Godolphin, W., Jones, L. A., Holt, J. A., Wong, S. G., Keith, D. E., Levin, W. J., Stuart, S. G., Udove, J., Ullrich, A. et al. (1989) *Science* 244, 707-712). For lung cancer and for gastric cancer, in which PLAC1 is expressed in 42 and 58% of the cases, respectively, there is no approved mAb treatment so far owing to the lack of appropriate targets in these cancer types. PLAC1 is involved not only in proliferation but also cell motility, migration and invasion.

PLAC1 expression has been found in breast cancer, lung cancer, ovarian cancer, gastric cancer, prostate cancer, pancreatic cancer, renal cell cancer, hepatic cancer, sarcoma, thyroid cancer, and head and neck cancer. PLAC1 is a particularly valuable target for the prevention and/or treatment of breast cancer, lung cancer, gastric cancer, ovarian cancer, hepatocellular cancer, colon cancer, pancreatic cancer, esophageal cancer, head & neck cancer, kidney cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof. In one embodiment, the cancer disease associated with PLAC1 expression is breast cancer or lung cancer, preferably, metastatic cancer in the lung.

The terms "a subject carrying a tumor-associated antigen" or "a subject expressing a tumor associated antigen" are used interchangeably and mean that a tumor-associated antigen is present in a subject, for example, in normal tissues that express the tumor-associated antigen and/or in tumorigenic tissues that express or aberrantly express the tumor-associated antigen. The term "a cell carrying a tumor-associated antigen" preferably means that said cell carries said tumor-associated antigen on its surface, i.e., that the tumor-associated antigen is associated with the surface of said cell.

The term "epitope" refers to an antigenic determinant in a molecule, i.e., to the part in a molecule that is recognized by the immune system, for example, that is recognized by an antibody. For example, epitopes are the discrete, three-dimensional sites on an antigen, which are recognized by the immune system. In the context of the present invention, the epitope is preferably derived from a protein, in particular a self-protein. An epitope of a protein such as a tumor-associated antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 10, 11, 12, 13, 14, 15, 16, 17, 18, 19, 20, 21, 22, 23, 24, or 25 amino acids in length. The epitope in the context of the present invention is derived from a tumor-associated antigen, preferably a tumor-associated antigen which is a self-protein in a subject suffering from a disease associated with expression or aberrant expression of said tumor-associated antigen, e.g., a tumorigenic disease such as cancer. It is particularly preferred that the epitope in the context of the present invention is not a T-cell epitope. Preferably, the epitope in the context of the present invention is a B-cell epitope. The phrase "the epitope comprised by the nucleic acid of the present invention or the vector of the present invention" means "the nucleic acid coding for the epitope and being comprised by the nucleic acid of the present invention or the vector of the present invention".

The term "an amino acid sequence comprising an epitope" refers to an amino acid sequence that includes the amino acid sequence(s) of one or more epitopes and may optionally include other sequences such as linker sequences. If the amino acid sequence comprising an epitope comprises more than one epitopes, said epitopes may be identical to or different from each other. Preferably, the epitope is derived from a tumor-associated antigen as set forth above. The length of the amino acid sequence comprising an epitope is preferably such that when inserted or attached to a HBcAg protein, the chimeric HBcAg protein is still capable of assembling into virus-like particles. For example, the length of the amino acid sequence comprising an epitope may be up to 10, up to 20, up to 30, up to 50, up to 100, up to 150, up to 200, up to 250, or up to 300 amino acids.

A "linker sequence" is preferably an amino acid sequence connecting two other amino acid sequences. For example, a part of the HBcAg protein may be connected with a part of a tumor-associated antigen sequence, e.g., an epitope sequence, via a linker sequence. A preferred linker sequence is $G_4SG_4$ (SEQ ID NO: 24).

The terms "eliciting an immune response" and "inducing an immune response" are used interchangeably in the context of the present invention and preferably refer to induction of a humoral immune response. A humoral immune response preferably comprises the generation of antigen-specific antibodies, in particular, of epitope-specific antibodies. In the context of the present invention, the humoral immune response preferably comprises the generation of antibodies directed against a tumor-associated antigen, wherein preferably the tumor-associated antigen is a self-protein in the subject in which the humoral immune response is elicited. Thus, in preferred embodiments, the antibodies generated during the humoral immune response are autoantibodies, preferably directed against the tumor-associated antigen in its native conformation on the surface of a cell, e.g., a tumor cell, preferably a living tumor cell. In the context of the present invention, the antibodies generated during a humoral immune response are preferably capable of eliciting immune effector functions as described herein. Preferably, said immune effector functions are directed against cells carrying the tumor-associated antigen from which the epitope is derived on their surface. For example, the generated antibodies are capable of mediating ADCC and/or CDC against such cells and/or they directly induce apoptosis in or inhibit proliferation of the cells carrying the tumor-associated antigen on their surface. The terms "eliciting an immune response" and "inducing an immune response" may also refer to the induction of a cellular immune response and the induction of a cellular as well as a humoral immune response. The immune response, preferably the humoral immune response, may be protective/preventive/prophylactic and/or therapeutic. "Inducing" may mean that there was no immune response against a particular antigen before induction, but it may also mean that there was a certain level of immune response against a particular antigen before induction and after induction said immune response is enhanced. Thus, "inducing the immune response" in this context also includes "enhancing the immune response". Preferably, after inducing an immune response in an individual, said individual is protected from developing a disease such as a cancerous disease or the disease condition is ameliorated by inducing an immune response. For example, an immune response against a tumor-associated antigen may be elicited in a patient having cancer or in a subject being at risk of developing cancer. Eliciting an immune response in this case may mean that the disease condition of the patient is ameliorated, that the patient does not develop metastases, or that the subject being at risk of developing cancer does not develop cancer.

A "cellular immune response" or a "cellular response against an antigen" is meant to include a cellular response directed to cells characterized by presentation of an antigen with class I or class II MHC. The cellular response relates to cells called T-cells or T-lymphocytes which act as either 'helpers' or 'killers'. The helper T cells (also termed $CD4^+$ T cells) play a central role by regulating the immune response and the killer cells (also termed cytotoxic T-cells, cytolytic T-cells, $CD8^+$ T-cells or CTLs) kill diseased cells such as tumor cells, preventing the production of more diseased cells.

The term "antibody" refers to a glycoprotein comprising at least two heavy (H) chains and two light (L) chains interconnected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "immune effector functions" in the context of the present invention includes any functions mediated by components of the immune system that result in the inhibition of tumor growth and/or inhibition of tumor development, including inhibition of tumor dissemination and metastasis. Preferably, immune effector functions result in killing of tumor cells. Preferably, the immune effector functions in the context of the present invention are antibody-mediated effector functions. Such functions comprise complement dependent cytotoxicity (CDC), antibody-dependent cell-mediated cytotoxicity (ADCC), antibody-dependent cell-mediated phagocytosis (ADCP), induction of apoptosis in the cells carrying the tumor-associated antigen, for example, by binding of the antibody to a surface antigen, inhibition of CD40L- mediated signal transduction, for example, by binding of the antibody to the CD40 receptor or CD40 ligand (CD40L), and/or inhibition of proliferation of the cells carrying the tumor-associated antigen, preferably ADCC and/or CDC. Thus, antibodies that are capable of mediating one or more immune effector functions are preferably able to mediate killing of cells by inducing CDC-mediated lysis, ADCC-mediated lysis, apoptosis, homotypic adhesion, and/or phagocytosis, preferably by inducing CDC-mediated lysis and/or ADCC-mediated lysis. Antibodies may also exert an effect simply by binding to tumor-associated antigens on the surface of a tumor cell. For example, antibodies may block the function of the tumor-associated antigen or induce apoptosis just by binding to the tumor-associated antigen on the surface of a tumor cell. For example, antibodies binding to PLAC1 on the cell surface blocks proliferation of the cells. In a preferred embodiment, the tumor-associated antigen is PLAC1 and the effector functions exerted by the antibodies induced against PLAC1 comprise inhibition of proliferation.

ADCC describes the cell-killing ability of effector cells, in particular lymphocytes, which preferably requires the target cell being marked by an antibody. ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that also leads to antigen presentation and the induction of tumor-directed T-cell responses. Preferably, in vivo induction of ADCC will lead to tumor-directed T-cell responses and further host-derived antibody responses.

CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

The term "immune effector cells" in the context of the present invention relates to cells which exert effector functions during an immune reaction. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer cells, neutrophils, macrophages, and dendritic cells.

The terms "subject" and "individual" are used interchangeably and relate to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans. The term "subject" may also include a patient, i.e., an animal, preferably a human having a disease, preferably a disease associated with expression or aberrant expression of a tumor-associated antigen such as CLDN18.2, CLDN6, or PLAC1, preferably a tumorigenic disease such as a cancer. In preferred embodiments, the immune system of the subject is not compromised or is essentially not compromised. This means that essential properties of a properly functioning immune system of the subject are present in the subject. This includes, in particular, that the subject is able of producing an immune reaction towards an administered antigen which is comparable to an immune reaction which would be expected from an individual with a normally functioning immune system, e.g., with respect to the type of the immune reaction such as induction of a humoral and/or cellular immune response, the strength and/or duration of the induced immune reaction, or the specificity of the induced immune reaction. Alternatively or additionally, this may include that self-tolerance mechanisms are maintained and present in said subject. For example, these self-tolerance mechanisms could, e.g., result in a suppression of an immune reaction against a tumor-associated antigen which is a self-protein if administered as such.

According to the invention, the term "nucleic acid" comprises deoxyribonucleic acid (DNA), ribonucleic acid (RNA), combinations thereof, and modified forms thereof. The term comprises genomic DNA, cDNA, mRNA, recombinantly produced and chemically synthesized molecules. According to the invention, a nucleic acid may be present as a single-stranded or double-stranded and linear or covalently circularly closed molecule.

In the context of the present invention, the terms "immunogenic composition" and "vaccine composition" are used interchangeably and relate to an antigenic preparation which comprises the protein according to the present invention, preferably in the form of a virus-like particle. The immunogenic composition may be administered to a subject in order to stimulate the humoral and/or cellular immune system of said subject against one or more antigens, preferably against one or more tumor-associated antigens, which are preferably self-proteins in said subject. An immunogenic composition in the context of the present invention preferably exerts its immunogenic potential without the addition of adjuvants and is preferably administered to a subject in any suitable route in order to elicit a protective and/or therapeutic immune reaction against the antigen, e.g., the tumor-associated antigen from which the epitope is derived which is comprised by the protein of the present invention. In a preferred embodiment, the immunogenic composition according to the present invention is capable of inducing antibody generation against the epitope derived from a tumor-associated antigen within the subject administered with said immunogenic composition, wherein the tumor-associated antigen is preferably a self-protein within said subject. In other words, in a particularly preferred embodiment, the immunogenic composition of the present invention is capable of eliciting a humoral immune response which comprises the generation of autoantibodies against a tumor-associated antigen which is a self-protein in the subject to which the immunogenic composition has been administered.

The term "breaking self-tolerance" refers to any procedure that causes the immune system of a subject to generate an immune response against a self-protein. Usually, self-proteins are protected from a subject's own immune system due to self-tolerance. The immune system recognizes self-proteins as "self" and does not attack such structures. This means for tumor-associated antigens, which are often self-proteins, that cells carrying said tumor-associated antigens are not recognized as foreign or diseased and thus are not attacked by the immune system due to an existing self-tolerance towards said antigens. Thus, in the context of tumor therapy, it is desired to break self-tolerance towards tumor-associated antigens.

The term "immunotherapy" relates to a treatment involving activation of a specific immune reaction. In the context of the present invention, terms such as "protect", "prevent", "prophylactic", "preventive", or "protective" relate to the prevention or treatment or both of the occurrence and/or the propagation of a tumor in an individual. The term "immunotherapy" in the context of the present invention preferably refers to active tumor immunization or tumor vaccination. A prophylactic administration of an immunotherapy, for example, a prophylactic administration of the immunogenic composition of the invention, preferably protects the recipient from the development of tumor growth. A therapeutic administration of an immunotherapy, for example, a therapeutic administration of the immunogenic composition of the invention, may lead to the inhibition of the progress/growth of the tumor. This comprises the deceleration of the progress/growth of the tumor, in particular a disruption of the progression of the tumor, which preferably leads to elimination of the tumor. A therapeutic administration of an immunotherapy may protect the individual, for example, from the dissemination or metastasis of existing tumors.

The term "immunization" or "vaccination" describes the process of administering antigen to a subject with the purpose of inducing an immune response for therapeutic or prophylactic reasons.

The term "adjuvant" relates to compounds which when administered in combination with an antigen or antigen peptide to an individual prolongs or enhances or accelerates the immune response. The immunogenic composition of the present invention preferably exerts its immunogenic effect without addition of adjuvants. Still, the immunogenic composition of the present invention may contain any known adjuvant. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B-cells, macrophages, dendritic cells, T-cells and unspecific activation of immune cells. Adjuvants comprise a heterogeneous group of compounds such as oil emulsions (e.g., Freund's adjuvants), mineral compounds (such as alum), bacterial products (such as *Bordetella pertussis* toxin), liposomes, and immune-stimulating complexes. Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides (Krieg et al., 1995, Nature 374: 546-549), Flt3 ligands (DE 10 2008 061 522), and various water-in-oil emulsions which are prepared from biologically degradable oils such as squalene and/or tocopherol.

Terms such as "increasing" or "enhancing" preferably relate to an increase or enhancement by about at least 10%, preferably at least 20%, preferably at least 30%, more preferably at least 40%, more preferably at least 50%, even more preferably at least 80%, and most preferably at least 100%. These terms may also relate to circumstances, wherein at time zero there is no detectable signal for a certain compound or condition and at a particular time point later than time zero there is a detectable signal for a certain compound or condition.

The immunogenic composition according to the present invention is generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid, or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical formulation which are not active ingredients such as, e.g., carriers, binders, lubricants, thickeners, surface active agents, preservatives, emulsifiers, buffers, flavoring agents, or colorants.

The immunogenic compositions according to the present invention may comprise a pharmaceutically acceptable carrier. The term "pharmaceutically acceptable carrier" in the context of the present invention relates to one or more compatible solid or liquid fillers or diluents, which are suitable for an administration to a human. The term "carrier" relates to a natural or synthetic organic or inorganic component which is combined with an active component in order to facilitate the application of the active component. Preferably, carrier components are sterile liquids such as water or oils, including those which are derived from mineral oil, animals, or plants, such as peanut oil, soy bean oil, sesame oil, sunflower oil, etc. Salt solutions and aqueous dextrose and glycerin solutions may also be used as aqueous carrier compounds.

According to the present invention, the immunogenic composition is administered in a therapeutically effective amount.

A "therapeutically effective amount" relates to an amount which—alone or in combination with further dosages—results in a desired reaction or a desired effect. In the case of the therapy of a particular disease or a particular condition, the desired reaction relates to the inhibition of the progress of the disease. This comprises the deceleration of the progress of the disease, in particular a disruption of the progression of the disease. The desired reaction for a therapy of a disease or a condition may also be the retardation of the occurrence or the inhibition of the occurrence of the disease or the condition. An effective amount of the composition according to the present invention is dependent on the condition or disease, the severity of the disease, the individual parameters of the patient, including age, physiological condition, height, and weight, the duration of the treatment, the type of an optionally accompanying therapy, the specific administration route, and similar factors. In case the reaction of a patient is insufficient with an initial dosage, multiple immunizations or higher dosages (or higher effective dosages which may be achieved by a more localized administration route) may be applied. In general, for a treatment or for an induction or increase of an immune reaction in a human preferably dosages of the protein of the present invention, preferably of the virus-like particle of the present invention, in the range of 0.01 to 200 µg/kg body weight, and preferably in the range of 0.1 to 100 µg/kg are formulated and administered. In a preferred embodiment, 50 µs to 2 mg, preferably 600 µg of the virus-like particle of the invention is administered to a human patient having a body weight of about 80 kg. Preferably, this amount is administered three times, preferably according to a standard immunization protocol.

In one embodiment, the immunogenic compositions according to the present invention are administered no more than five times, no more than four times, no more than three times, or no more than two times over a period of 40 days, 30 days, 20 days, 15 days, or 10 days starting with the first administration of the immunogenic compositions according to the present invention. In one embodiment, the immunogenic compositions according to the present invention are administered three times, or two times over a period of 30 days, 20 days, 15 days, or 10 days starting with the first administration of the immunogenic compositions according to the present invention. Preferably, this administration of the immunogenic compositions according to the present invention is followed by one or more, preferably singular booster administrations using immunogenic compositions according to the present invention which preferably are given not earlier than 15 days, 20 days, 40 days, 50 days, or 60 days after the last administration of the immunogenic compositions according to the present invention or the last booster administration.

The term "expression" is used herein in its broadest meaning and comprises the production of RNA or of RNA and protein. With respect to RNA, the term "expression" or "translation" relates in particular to the production of peptides or proteins. Expression may be transient or may be stable.

According to the present invention, the term "peptide" comprises oligo- and polypeptides and refers to substances comprising two or more, preferably three or more, preferably four or more, preferably six or more, preferably eight or more, preferably ten or more, preferably 14 or more, preferably 16 or more, preferably 21 or more and up to preferably 8, 10, 20, 30, 40, or 50, in particular 100 amino acids joint covalently by peptide bonds. The term "protein" refers to large peptides, preferably to peptides with more than 100 amino acid residues, but in general the terms "peptides" and "proteins" are synonymous and are used interchangeably herein.

DETAILED DESCRIPTION

The present inventors have surprisingly found that it is possible to induce a humoral immune response in a subject, i.e., to induce a subject's immune system to generate antibodies, in particular autoantibodies, against tumor-associated antigens, wherein the generated antibodies are capable of recognizing the tumor-associated antigen in its native form on the surface of a cell and of exerting immune effector functions against cells carrying said tumor-associated antigen. In particular, the present invention makes use of virus-like particles composed of a hepatitis B virus core antigen protein as carrier for epitopes derived from tumor-associated antigens.

For all aspects of the present invention relating to induction of immune responses and/or prophylactic and/or therapeutic treatments of tumorigenic diseases, it is to be understood that the immune response is induced against the tumor-associated antigen from which the epitope is derived that is inserted into or attached to specific locations of the HBcAg protein and that the prophylactic and/or therapeutic treatment of the tumorigenic disease is with respect to a tumorigenic disease associated with surface expression of the tumor-associated antigen from which the epitope is derived. For example, if the epitope is derived from CLDN6, the induced immune response and the prophylactic and/or therapeutic treatment is directed against CLDN6 expressing cells, preferably CLDN6 expressing tumor cells, and against tumorigenic diseases associated with CLDN6 expression. The same applies for CLDN18.2 and PLAC1 and any other tumor-associated antigen. The specific preferred tumor types for the specific tumor-associated antigens are given herein and apply to all aspects of the present invention.

In one aspect, the present invention provides a protein comprising all or a portion of the amino acid sequence of a hepatitis B virus core antigen protein and inserted therein or attached thereto an amino acid sequence comprising an epitope, wherein the epitope is derived from an extracellular portion of a tumor-associated antigen associated with the surface of a tumor cell. Preferably, the tumor-associated antigen is expressed in a limited number of specific tissues and/or organs under normal conditions, preferably in not more than 3, more preferably in not more than 2, most preferably in one specific tissue or organ and is expressed or aberrantly expressed in tumor tissues.

Preferably, the amino acid sequence comprising the epitope is inserted into or attached to the amino acid sequence of the hepatitis B virus core antigen protein or the portion thereof such that the epitope assumes at least partially its native conformation. Native conformation, in this context, means that the epitope exhibits the same structure as it assumes within its natural environment, i.e., within the tumor-associated antigen it is derived from, under native conditions, i.e., under conditions the tumor-associated antigen is usually found in. The term "partially" in this context may mean that the structure of the epitope within the chimeric HBcAg protein is not necessarily 100% identical to the structure of the epitope within the tumor-associated antigen, but that at least a significant similarity can be identified. Thus, preferably, antibodies generated against the epitope within the protein of the present invention are able to recognize and to bind to the tumor-associated antigen in its native conformation preferably on the surface of a cell, preferably a tumor cell, preferably a living tumor cell, preferably a living tumor cell in its natural environment. Preferably, the epitope assumes such conformation that an immune response against cells carrying the tumor-associated antigen is elicited in a subject expressing the tumor-associated antigen when the protein of the invention is administered to said subject, preferably in the form of a virus-like particle. Preferably said immune response is elicited even when the tumor-associated antigen is a self-protein in said subject. In a preferred embodiment, the protein of the present invention is capable of eliciting an immune response, preferably a humoral immune response, against the tumor-associated antigen the epitope is derived from in a subject against a self-tolerance towards the tumor-associated antigen existing in said subject. Preferably, the protein of the present invention is capable of eliciting said immune response, preferably in the form of a virus-like particle, even when administered without adjuvant.

In a particularly preferred embodiment of the protein of the present invention, said protein is capable of eliciting a humoral immune response directed against the tumor-associated antigen in association with the surface of a cell when administered in the form of a virus-like particle without adjuvant to a subject, wherein the tumor-associated antigen is a self-protein in said subject. Preferably, the humoral immune response comprises the generation of antibodies, preferably autoantibodies, which exhibit one or more immune effector functions, preferably against cells carrying the tumor-associated antigen in its native conformation. Preferably, the one or more immune effector functions are selected from the group consisting of complement dependent cytotoxicity (CDC), antibody-dependent cell-mediated cytotoxicity (ADCC), antibody-dependent cell-mediated phagocytosis (ADCP), induction of apoptosis, inhibition of proliferation, and inhibition of CD40L-mediated signal transduction, preferably the effector functions are ADCC and/or CDC.

The skilled person can readily determine whether a protein fulfills the above criteria. For example, the skilled person may generate a protein as described above comprising an epitope derived from the extracellular portion of a tumor-associated antigen, such as CLDN6, CLDN18.2, or PLAC1, using, for example, a mouse- or rabbit-specific amino acid sequence. The skilled person may then immunize rabbits with a protein comprising the rabbit-specific epitope or mice with the protein comprising the mouse-specific epitope, wherein the protein is preferably in the form of a virus-like particle and is preferably administered without adjuvants. The skilled person is well aware of immunization schemes and any of these schemes may be employed. After immunization is completed, serum may be harvested from the animals and the serum may be tested for antibody-mediated effector functions on cells, preferably tumor cells, endogenously or exogenously expressing the tumor-associated antigen having the amino acid sequence of the respective species the epitope was derived from and the immunization has been performed in. For example, killing of cells carrying the respective tumor-associated antigen on their surface or inhibition of proliferation of such cells can be determined. Such methods are exemplarily described in the Examples section of the present invention.

In a particular preferred embodiment, the tumor-associated antigen is a protein of the claudin family or PLAC1. Preferably, the protein of the claudin family is selected from the group consisting of CLDN18.2 and CLDN6.

The epitope is preferably between 5 amino acids and the entire length of a continuous part of the extracellular portion of the tumor-associated antigen and is preferably specific for said tumor-associated antigen. For example, the epitope may be between 5 and 100, preferably between 5 and 50, more preferably between 8 and 30, most preferably between 10 and 25 amino acids in length, for example, the epitope may be preferably 10, 11, 12, 13, 14, 15, 16, 17, 18, 19, 20, 21, 22, 23, 24, or 25 amino acids in length.

Particularly preferred epitope sequences in the context of the present invention are for CLDN6 PMWKVTAFIGNSI (SEQ ID NO: 9), MWKVTAFIGNSIVVA (SEQ ID NO: 10), FIGNSIVVAQVVWE (SEQ ID NO: 11), VVAQVVWEGLWMS (SEQ ID NO: 12), VAQVVWEGLWMSCVVQSTGQMQC (SEQ ID NO: 13), KVTAFIGNSIVVAQVV (SEQ ID NO: 14), KVTAFIGNSIVVAQ (SEQ ID NO: 15), RDFYNPLVAEAQK (SEQ ID NO: 16), DFYNPLVAEAQ (SEQ ID NO: 17), TAHAIIRDFYNPL (SEQ ID NO: 18), DFYNPLVAEAQK (SEQ ID NO: 19), and IRDFYNPLVAEAQKRE (SEQ ID NO: 20), for CLDN18.2 TQDLYNNPVT (SEQ ID NO: 21), DLYNNPVTAVFNYQGL (SEQ ID NO: 45), NNPVTAVFNYQ (SEQ ID NO: 46), VTAVFNYQGL (SEQ ID NO: 47), SCVRESSGF (SEQ ID NO: 48), VRESSGFTE (SEQ ID NO: 49), VRESSGFTE (SEQ ID NO: 50), RGYFTLLGL (SEQ ID NO: 51), ECRGYFTLLGL (SEQ ID NO: 52), AVFNYQGLW RSCVRES (SEQ ID NO: 53), DQWSTQDLYNNPVTAVFNYQ (SEQ ID NO: 54), MDQWSTQDLYNNPVTAVFNYQGL (SEQ ID NO: 55), WRSCVRESSGFTECRGYFTLLGLPAMLQAVR (SEQ ID NO: 56), RIGSMEDSAKANMTLTS (SEQ ID NO: 57), TNFWMSTANMYTGMGGMVQTVQTRYTF (SEQ ID NO: 58), and for PLAC1 VFSEEEHTQVP (SEQ ID NO: 22), VFSEEEHTQV (SEQ ID NO: 23), APQKSPWLTKP (SEQ ID NO: 59), QKSPWLTKP (SEQ ID NO: 60), APQKSPWLT (SEQ ID NO: 61), MRVASKSR (SEQ ID NO: 62), APQKSP (SEQ ID NO: 63), TAQKDEK (SEQ ID NO: 64), SKGTPSK (SEQ ID NO: 65), APQKSPWLTK (SEQ ID NO: 66), QKSPWLTK (SEQ ID NO: 67), SMRVASKSRATAQKDEK (SEQ ID NO: 68), PPNHVQPHAYQFTYRVTE (SEQ ID NO: 69), SMRVASKSKRATAQKDE (SEQ ID NO: 70), SMRVASKSKRATA QKD (SEQ ID NO: 71), SMRVASKSKRATAQK (SEQ ID NO: 72), RVASKSKRATA (SEQ ID NO: 73), YEVFSLSQSSQRPN (SEQ ID NO: 74), EVFSLSQSSQR (SEQ ID NO: 75), IDWFMVTVHPFMLNNDV (SEQ ID NO: 76), IDWFMVTVHPFMLNND (SEQ ID NO: 77), IDWFMVTVHPFMLNN (SEQ ID NO: 78), and variants thereof.

In a preferred embodiment of the protein of the present invention, the epitope comprises, preferably essentially consists of, preferably consists of (i) an amino acid sequence which is selected from the group consisting of the amino acid sequences set forth in SEQ ID NOs: 9 to 23 and 45 to 78 of the sequence listing, (ii) an amino acid sequence that is at least at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence under (i) preferably over the entire length of the epitope sequence, and is immunologically equivalent to the amino acid sequence under (i), or (iii) an amino acid sequence under (i) or (ii) which is truncated and is immunologically equivalent to the amino acid sequence under (i). Said truncation may be at the amino-terminus or at the carboxy-terminus and is preferably not more than 40%, preferably not more than 30%, preferably not more than 20%, more preferably not more than 10% of the entire length of the epitope sequence.

Variants and/or derivatives of these epitopes are also contemplated in the present invention as long as said variants and/or derivatives are immunologically equivalent to the specifically disclosed epitopes. The skilled person will understand that single amino acid substitutions, additions, insertions, and/or deletions within the epitope may not alter the immunological properties of said epitopes significantly.

In a preferred embodiment of the protein of the present invention, the hepatitis B virus core antigen protein comprises, preferably essentially consists of, preferably consists of an amino acid sequence selected from the group consisting of
(i) the amino acid sequence set forth in SEQ ID NO: 1 or a portion thereof of at least 50 amino acids, preferably of at least 60 amino acids, preferably of at least 70 amino acids, preferably of at least 80 amino acids, preferably of at least 90 amino acids, preferably of at least 100 amino acids, preferably of at least 110 amino acids, preferably of at least 120 amino acids, preferably of at least 130 amino acids, preferably of at least 140 amino acids, or
(ii) an amino acid sequence that is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99% identical, preferably at least 80% identical, to the amino acid sequence or the portion thereof under (i) preferably over the entire length of the amino acid sequence or the portion thereof under (i). Preferably, the hepatitis B virus core antigen protein used in the present invention is functionally equivalent to the naturally occurring hepatitis B virus core antigen protein with respect to assembly into virus-like particles, preferably into the conventional shape of hepatitis B virus core antigen virus-like particles, i.e., being composed of 180 or 240 subunits and having an icosahedral structure.

In a particularly preferred embodiment, the HBcAg protein or the portion thereof has a truncation at the carboxy-terminus at an amino acid position up to and including the position 140 of SEQ ID NO: 1 or a corresponding amino acid position. For example, the carboxy-terminal truncation may be at and includes position 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, or 183 of SEQ ID NO: 1 or a corresponding amino acid. A carboxy-terminal truncation at and including position 140 of SEQ ID NO: 1 means that the amino acids from position 140 to the carboxy-terminus are missing in this particular HBcAg variant or portion, i.e., that this HBcAg protein variant or portion may consist of amino acids 1 to 139 of SEQ ID NO: 1. "A corresponding amino acid position" in this context means that if the protein of the present invention comprises a HBcAg protein other than the HBcAg protein set forth in SEQ ID NO: 1, for example, a naturally occurring variant that has an insertion, addition, and/or deletion, the amino acid at position 140 of SEQ ID NO: 1 may not correspond to the amino acid at position 140 of said naturally occurring HBcAg variant but to a position with a lower or higher number. The corresponding amino acids can be determined as described above, for example, by sequence alignment.

In a particular preferred embodiment of the protein of the present invention, the hepatitis B virus core antigen protein has a truncation at the carboxy-terminus such that it is not able to bind to nucleic acids but retains the ability to assemble into virus-like particles. The major RNA recognizing activity was attributed to a region within the HBcAg protein corresponding to amino acids 150 to 157 of SEQ ID NO: 1. The major DNA-recognizing activity was attributed to a region within the HBcAg protein corresponding to amino acids 157 to 177 of SEQ ID NO: 1. Thus, for abolishing the nucleic acid binding ability of the HBcAg protein, these sequences responsible for nucleic acid binding are preferably deleted.

A particularly preferred truncation variant of the HBcAg protein used in the present invention is a truncation at and including the amino acid position 151 of SEQ ID NO: 1 or a corresponding amino acid position, i.e., a HBcAg protein variant which carboxy-terminal amino acid corresponds to the amino acid at amino acid position 150 of SEQ ID NO: 1. In a preferred embodiment, said truncation variant of the HBcAg protein further comprises a carboxy-terminal Histag, preferably linked to the HBcAg truncation variant via a glycine linker such as a GGS linker. Preferably, said truncation variant of the HBcAg protein comprises, essentially consists of, or consists of the amino acid sequence set forth in SEQ ID NO: 79. Preferably, said truncation variant of the HBcAg protein is encoded by a nucleic acid set forth in SEQ ID NO: 80.

In preferred embodiments of the protein of the present invention, all or part of the amino acid sequence corresponding to the MIR of the hepatitis B virus core antigen protein is deleted. For example, all or part of the amino acids 74 to 89 of SEQ ID NO: 1 may be deleted.

In a preferred embodiment of the protein of the present invention, the amino acid sequence comprising an epitope
(i) is attached to the amino-terminal amino acid of the hepatitis B virus core antigen protein, is inserted into the 30 amino-terminal amino acid residues, preferably the 20 amino-terminal amino acid residues, preferably the 10 amino-terminal amino acid residues, preferably the 5 amino-terminal amino acid residues of the hepatitis B virus core antigen protein, or replaces one or more, for example, 1, 2, 3, 4, 5, 6, 7, 8, 9, or 10 amino acids, of the 30 amino-terminal amino acid residues, preferably of the 20 amino-terminal amino acid residues, preferably of the 10 amino-terminal amino acid residues of the hepatitis B virus core antigen protein, and/or
(ii) is attached to the carboxy-terminal amino acid of the hepatitis B virus core antigen protein or is inserted into the 30 carboxy-terminal amino acid residues, preferably the carboxy-terminal amino acid residues, preferably the 10 carboxy-terminal amino acid residues of the hepatitis B virus core antigen protein, or replaces one or more, for example, 1, 2, 3, 4, 5, 6, 7, 8, 9, or 10 amino acids, of the 30 carboxy-terminal amino acid residues, preferably of the 20 carboxy-terminal amino acid residues, preferably of the 10 carboxy-terminal amino acid residues of the hepatitis B virus core antigen protein, and/or
(iii) is inserted into the amino acid sequence corresponding to the MIR of the hepatitis B virus core antigen protein or replaces one or more amino acids, for example, 1, 2, 3, 4, 5, 6, 7, 8, 9, 10, 11, 12, 13, 14, 15, or 16 amino acids, within the amino acid sequence corresponding to the MIR of the hepatitis B virus core antigen protein, and/or
(iv) is attached to one or more amino acids located within the amino acid sequence corresponding to the MIR of the hepatitis B virus core antigen protein, for example, to one or more of the amino acids 74, 75, 76, 77, 78, 79, 80, 81, 82, 83, 84, 85, 86, 87, 88, or 89 of SEQ ID NO: 1 or a corresponding amino acid.

If the amino acid sequence comprising an epitope is attached to the amino-terminal amino acid of the hepatitis B virus core antigen protein or inserted between amino-terminal residues it is preferred that the amino acid sequence comprising an epitope has a maximal length of 50 amino acid residues, preferably 40 amino acid residues, preferably 30 amino acid residues. It is also preferred that no more than 9, preferably no more than 5, preferably no more than 4, preferably no more than 3 amino acids are deleted from the amino-terminus of the hepatitis B virus core antigen protein.

It is particularly preferred that the amino acid sequence comprising an epitope is inserted into the MIR or replaces one or more amino acids of the MIR. Preferably, the amino acid sequence comprising an epitope
(i) is inserted into the hepatitis B virus core antigen protein between the amino acids at positions 77 and 78 of the amino acid sequence set forth in SEQ ID NO: 1 of the sequence listing or at a corresponding position, or
(ii) replaces the amino acids at positions 74-81, 76-81, 76-79, or 79-80 of the amino acid sequence set forth in SEQ ID NO: 1 of the sequence listing or at corresponding positions.

It is particularly preferred that the amino acid sequence comprising the epitope is inserted into or attached to the hepatitis B virus core antigen protein such that the chimeric hepatitis B virus core antigen protein, i.e., the hepatitis B virus core antigen protein comprising an epitope derived from a tumor-associated antigen as described above, is capable of assembling into virus-like particles, preferably into conventional hepatitis B virus core antigen protein virus-like particles. This feature of the protein can be easily determined by the skilled person, for example, by using transmission electron microscopy or asymmetric flow-field-flow fractionation combined with dynamic light scattering, for example, as described in the Examples section of the present invention.

It is also preferred that the structure, in particular the length, of the amino acid sequence comprising the epitope is chosen such that the chimeric hepatitis B virus core antigen protein, i.e., the hepatitis B virus core antigen protein comprising an epitope derived from a tumor-associated antigen as described above, is capable of assembling into virus-like particles. Thus, the amino acid sequence comprising an epitope is preferably not more than 300, preferably not more than 250, preferably not more than 200, preferably not more than 150, and more preferably not more than 100 amino acids in length. It is preferred that the amino acid sequence comprising an epitope is up to 100 amino acid residues in length, for example, 10, 15, 20, 25, 30, 35, 40, 45, 50, 55, 60, 65, 70, 75, 80, 85, 90, 95, or 100 amino acids. It is particularly preferred that the length of the amino acid sequence comprising an epitope is between 20 and 60 amino acids, preferably between 25 and 55 amino acids, for example, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids.

In some embodiments of the protein of the present invention, the protein may in addition to the first amino acid sequence comprising an epitope comprise one or more further amino acid sequences comprising an epitope inserted into or attached to the hepatitis B virus core antigen protein, wherein one or more of the epitopes of the one or more further amino acid sequences comprising an epitope are identical to or different to each other and one or more of the epitopes of the one or more further amino acid sequences comprising an epitope are identical to or different from the epitope of the first amino acid sequence comprising an epitope. These one or more further amino acid sequences comprising an epitope may be inserted into or attached to the hepatitis B virus core antigen protein as described above for the first amino acid sequence comprising an epitope. The disclosure on the length of the first amino acid sequence comprising an epitope as well as on the epitope etc. also applies to the one or more further amino acid sequences comprising an epitope. It is particularly preferred, that a chimeric hepatitis B virus core antigen protein comprising more than one amino acid sequences comprising an epitope is capable of assembling into virus-like particles.

In some embodiments of the protein of the present invention, the first amino acid sequence comprising an epitope and/or one or more of the further amino acid sequences comprising an epitope comprise(s) more than one epitope, wherein the epitopes are identical or different. For example, one epitope within an amino acid sequence comprising more than one epitope may be derived from one tumor-associated antigen and the other epitope may be derived from another tumor-associated antigen. This is particularly advantageous if a certain type of tumor can be recognized by a combination of tumor-associated antigens. The epitopes within one amino acid sequence comprising more than one epitope may also be derived from the same tumor-associated antigen. In this case, the epitopes may be, for example, derived from different extracellular loops or portions of the tumor-associated antigen or from the same extracellular loop or portion.

The protein of the present invention may comprise one or more linker sequences between the individual elements making up the proteins, e.g., the HBcAg protein derived parts and the amino acid sequence(s) comprising an epitope. Preferably, the amino acid sequence comprising an epitope further comprises a linker sequence up-stream and/or down-stream of the epitope sequence. For example, if the amino acid sequence comprising an epitope is inserted into or replaces all or part of the MIR of the hepatitis B virus core antigen protein, in particular if it replaces all of the MIR or a major part thereof, it is particularly preferred that the epitope is flanked by linker sequences on each side of the epitope.

The linker preferably consists of maximally 50 amino acids, preferably of maximally 40 amino acids, more preferably of maximally 30 amino acids, even more preferably of maximally 20 amino acids, and most preferably of maximally 10 amino acids. It is particularly preferred that the linker consists of between 2 to 25 amino acids, preferably between 2 to 20 amino acids, e.g., 2, 3, 4, 5, 6, 7, 8, 9, 10, 11, 12, 13, 14, 15, 16, 17, 18, 19, or amino acids, most preferably 9 amino acids. The linker preferably comprises, preferably essentially consists of, preferably consists of small amino acids such as glycine, alanine, or serine. Preferably, the linker is chosen such that the linked amino acid sequences, for example, the epitope sequence, is able to assume at least partially its native structure under native conditions. A preferred linker essentially consists of glycine and serine residues, e.g., having a length of between 5 and 15 amino acids, for example, preferred linkers are $Gly_mSer_nGly_p$, wherein m, n, and p are integers independently selected from 1 to 10, wherein m+n+p is between 5 and 15. A particularly preferred linker is $G_4SG_4$ (SEQ ID NO: 24). In embodiments wherein the epitope sequence is flanked by linker sequences, the linker sequences may be considered to be comprised by the HBcAg portion of the protein of the present invention, by the amino acid sequence comprising an epitope portion of the protein of the present invention, or one of the two linker sequences may be considered comprised by the HBcAg portion of the protein of the present invention and the other linker sequence by the amino acid sequence comprising an epitope portion of the protein of the present invention.

In some embodiments, the protein of the present invention may comprise one or more epitope-, peptide-, or protein-tags, for example, for facilitating purification of the protein of the present invention. Such epitope-, peptide-, or protein-tags include, but are not limited to, hemagglutinin- (HA-), FLAG-, myc-tag, poly-His-tag, glutathione-S-transferase- (GST-), maltose-binding-protein- (MBP-), NusA-, and thioredoxin-tag, or fluorescent protein-tags such as (enhanced) green fluorescent protein ((E)GFP), (enhanced) yellow fluorescent protein ((E)YFP), red fluorescent protein (RFP) derived from *Discosoma* species (DsRed) or monomeric (mRFP), cyan fluorescence protein (CFP), and the like. In a preferred embodiment, the epitope-, peptide-, or protein-tags can be cleaved off the protein of the present invention, for example, using a protease such as thrombin, Factor Xa, PreScission, TEV protease, and the like. The recognition sites for such proteases are well known to the person skilled in the art. Preferably, a small epitope- or peptide-tag is used such as a His-tag, HA-tag, or FLAG-tag, and preferably the tag can be removed. In a preferred embodiment, the protein of the present invention comprises a His-tag, preferably a $His_6$-tag, preferably at the carboxy-terminus. Preferably, the epitope-, peptide-, or protein-tag is connected to one or more of the other elements of the protein of the present invention via a linker, wherein the linker may be as described above. A preferred linker in this context is the amino acid sequence GGS.

In preferred embodiments of the chimeric HBcAg proteins of the present invention, the HBcAg backbone sequence is selected from the group consisting of the amino acid sequences set forth in SEQ ID NOs: 25 to 30, i.e., HBcAg backbones A, B, C, D, E, and F (FIG. 7). Preferred nucleic acid sequences encoding for the HBcAg backbones are the nucleic acid sequences set forth in SEQ ID NOs: 31 to 36, wherein SEQ ID NO: 31 codes for SEQ ID NO: 25, SEQ ID NO: 32 codes for SEQ ID NO: 26, SEQ ID NO: 33 codes for SEQ ID NO: 27, SEQ ID NO: 34 codes for SEQ ID NO: 28, SEQ ID NO: 35 codes for SEQ ID NO: 29, and SEQ ID NO: 36 codes for SEQ ID NO: 30. The term "HBcAg backbone" relates to the portion of the protein of the invention that is not the amino acid sequence comprising an epitope. It is particularly preferred that these backbones are combined with amino acid sequences comprising one or more of the epitope sequences set forth in SEQ ID NOs: 9 to 23 and 45 to 78 of the sequence listing. For example, HBcAg backbone A (SEQ ID NO: 25) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78, HBcAg backbone B (SEQ ID NO: 26) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78, HBcAg backbone C (SEQ ID NO: 27) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78, HBcAg backbone D (SEQ ID NO: 28) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78, HBcAg backbone E (SEQ ID NO: 29) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78, or HBcAg backbone F (SEQ ID NO: 30) may be combined with an amino acid sequence comprising SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, or SEQ ID NO: 78. Preferably, the amino acid sequence comprising an epitope is inserted into the HBcAg backbone between the linker sequence GGGGSGGGG (SEQ ID NO: 24) and the HBcAg portion, i.e., immediately upstream or downstream of this linker sequence. Preferably, the amino acid sequence comprising an epitope also comprises a linker sequence, wherein if the amino acid sequence comprising an epitope is inserted upstream of the linker sequence of the HBcAg backbone the linker sequence of the amino acid sequence comprising an epitope is located upstream of the epitope sequence, and if the amino acid sequence comprising an epitope is inserted downstream of the linker sequence of the HBcAg backbone the linker sequence of the amino acid sequence comprising an epitope is located downstream of the epitope sequence. Thus, in preferred embodiments, the epitope is flanked by linker sequences within the chimeric HBcAg proteins of the invention. It is to be understood that, for example, the His-tag located at the C-terminus of the HBcAg backbones may be replaced by any other epitope-, peptide-, or protein-tag as described above, and that the linker sequences may also vary as described above.

In a particularly preferred embodiment of the protein of the present invention, the epitope is the CLDN18.2$_{32-41}$ peptide having the sequence TQDLYNNPVT (SEQ ID NO: 21) which is flanked on both sides by a linker, preferably having the sequence Gly$_m$Ser$_n$Gly$_p$, wherein m, n, and p are integers independently selected from 1 to 10, wherein m+n+p is between 5 and 15, more preferably having the sequence G$_4$SG$_4$ (SEQ ID NO: 24). The epitope flanked on both sides by a linker (amino acid sequence comprising an epitope) is inserted into an HBcAg backbone sequence, wherein the portion of the HBcAg backbone sequence flanking the N-terminal side of the amino acid sequence comprising an epitope preferably comprises the amino acid sequence from positions 2 to 73, 2 to 75 or 2 to 78 of SEQ ID NO: 1, preferably the amino acid sequence from positions 1 to 73, 1 to 75 or 1 to 78 of SEQ ID NO: 1 and the portion of the HBcAg backbone sequence flanking the C-terminal side of the amino acid sequence comprising an epitope preferably comprises the amino acid sequence from positions 80 to 150, 81 to 150 or 82 to 150 of SEQ ID NO: 1. Preferably, the portion of the HBcAg backbone sequence flanking the N-terminal side of the amino acid sequence comprising an epitope comprises the amino acid sequence from positions 2 to 78 of SEQ ID NO: 1, preferably the amino acid sequence from positions 1 to 78 of SEQ ID NO: 1 and the portion of the HBcAg backbone sequence flanking the C-terminal side of the amino acid sequence comprising an epitope comprises the amino acid sequence from positions 81 to 150 of SEQ ID NO: 1. In one embodiment, the portion of the HBcAg backbone sequence flanking the N-terminal side of the amino acid sequence comprising an epitope may comprise additional sequences on its N-terminus and/or the portion of the HBcAg backbone sequence flanking the C-terminal side of the amino acid sequence comprising an epitope may comprise additional sequences on its C-terminus.

Particularly preferred examples of the protein of the present invention are proteins which comprise, preferably essentially consist of, preferably consist of an amino acid sequence selected from the group consisting of
 (i) the amino acid sequences set forth in SEQ ID NOs: 37 to 40 or
 (ii) an amino acid sequence that is at least 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, 99%, preferably at least 80%, identical to the amino acid sequence under (i) preferably over 60%, more preferably over at least 70%, more preferably over at least 80%, more preferably over at least 90%, most preferably over at least 95% of the entire length of the amino acid sequence under (i), and is functionally, preferably immunologically equivalent to the amino acid sequence under (i). For example, the amino acid sequence under (ii) is preferably able to assemble into virus-like particles and is preferably able to elicit an immune response, preferably a humoral immune response, in a subject against the tumor-associated antigen from which the epitope is derived, when administered to said subject preferably in the form of virus-like particles and without adjuvant. As specified above, the antibodies generated are preferably able to recognize and bind to the tumor-associated antigen in its native conformation preferably on the surface of a cell, preferably a tumor cell. Preferably said immune reaction is also elicited when the tumor-associated antigen is a self-protein in the subject.

Preferred nucleic acid sequences coding for the preferred examples of the protein of the present invention are the nucleic acids set forth in SEQ ID NO: 41 to 44, wherein SEQ ID NO: 41 codes for SEQ ID NO: 37, SEQ ID NO: 42 codes for SEQ ID NO: 38, SEQ ID NO: 43 codes for SEQ ID NO: 39, and SEQ ID NO: 44 codes for SEQ ID NO: 40.

In another aspect, the present invention provides a polynucleotide comprising, preferably essentially consisting of, preferably consisting of a nucleic acid encoding the protein of the invention. Particularly preferred examples of nucleic acids encoding the protein of the present invention are set forth in SEQ ID NOs: 41 to 44. Also variants of the nucleic acid sequences encoding the protein of the invention are contemplated by the present invention as described above, as long as the particular protein variant encoded by the nucleic acid variant is functionally, preferably immunologically equivalent to the respective protein. In preferred embodiments, the polynucleotides according to the present invention are optimized regarding the codon usage. For example, if the protein of the present invention is to be expressed in a prokaryotic host, such as E. coli, the polynucleotide encoding the protein of the present invention is preferably optimized for prokaryotic codon usage.

In a further aspect, the present invention provides a vector, preferably a recombinant vector, comprising the nucleic acid of the invention. "Recombinant" means that said vector does not naturally occur, for example, that said vector has been produced by genetic engineering. A vector in the context of the present invention may be any vector known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. The person skilled in the art is well aware of techniques used for the incorporation of polynucleotide sequences of interest into vectors (also see Sambrook et al., 1989, supra). Vectors, for example, plasmids may include an origin of replication (ori), a multiple cloning site, and regulatory sequences such as promoter (constitutive or inducible), transcription initiation site, ribosomal binding site, transcription termination site, polyadenylation signal, and selection marker such as antibiotic resistance or auxotrophic marker based on complementation of a mutation or deletion. In one embodiment, the polynucleotide sequence of interest is operably linked to the regulatory sequences.

In a further aspect, the present invention provides a host cell comprising the polynucleotide of the invention or the vector of the invention. The host cells may be prokaryotic cells such as archea or bacterial cells or eukaryotic cells such as yeast, plant, insect, or mammalian cells. In a preferred embodiment, the host cell is a bacterial cell such as an *E. coli* cell. The person skilled in the art is well aware of methods for introducing said polynucleotide or said vector into said host cell. For example, bacterial cells can be readily transformed using, for example, chemical transformation, e.g., the calcium chloride method, or electroporation. Yeast cells may be transformed, for example, using the lithium acetate transformation method or electroporation. Other eukaryotic cells can be transfected, for example, using commercially available liposome-based transfection kits such as Lipofectamine™ (Invitrogen), commercially available lipid-based transfection kits such as Fugene (Roche Diagnostics), polyethylene glycol-based transfection, calcium phosphate precipitation, gene gun (biolistic), electroporation, or viral infection. In a preferred embodiment of the invention, the host cell expresses the polynucleotide of the invention. The expressed protein may be soluble and/or expressed in inclusion bodies. The protein of the invention may be purified using protein purification methods well known to the person skilled in the art, optionally taking advantage of the above-mentioned epitope-, peptide-, or protein-tags. In one embodiment, the protein of the present invention is purified under denaturing conditions. The protein of the invention may then be assembled in vitro into virus-like particles.

In another aspect, the present invention provides a virus-like particle comprising multiple copies, for example, 10, 20, 30, 40, 50, 60, 70, 80, 90, 100, or more copies of the protein of the present invention. In a preferred embodiment, the virus-like particle of the invention is capable of eliciting an immune response, preferably a humoral immune response directed against the tumor-associated antigen in association with the surface of a cell when administered without adjuvant to a subject, wherein the tumor-associated antigen is a self-protein in said subject. It is clear to the skilled person that the tumor-associated antigen against which the humoral immune response is directed is the tumor-associated antigen from which the epitope is derived which is comprised by the protein of the present invention being comprised in the virus-like particle of the present invention.

The virus-like particle of the invention may be a conventional HBcAg virus-like particle, for example, consisting of 180 or 240 HBcAg protein subunits having preferably an icosahedral structure or it may assume any other virus-like particle structure, e.g., a spherical, globular, or rod shaped structure. Preferably, the virus-like particle consists of 180 or 240 subunits and has preferably an icosahedral structure.

In one embodiment, the virus-like particle of the invention is composed of hepatitis B virus core antigen proteins and multiple copies of the protein of the invention, wherein at least 50%, preferably at least 60%, preferably at least 70%, preferably at least 80%, more preferably at least 90%, even more preferably at least 95% of the protein subunits are the protein of the invention. For example, the virus-like particle may consist of 180 protein subunits, wherein 90, 100, 110, 120, 130, 140, 150, 160, 170, or 180 subunits may be the protein of the invention. For example, the virus-like particle may consist of 240 protein subunits, wherein 120, 130, 140, 150, 160, 170, 180, 190, 200, 210, 220, 230, or 240 subunits may be the protein of the present invention. The hepatitis B virus core antigen protein in this context is preferably a naturally occurring hepatitis B virus core antigen protein or a portion thereof, preferably a carboxy-terminally truncated portion thereof as specified above for the protein of the present invention. The hepatitis B virus core antigen may also be a genetically manipulated variant of a naturally occurring hepatitis B virus core antigen protein or a portion thereof, preferably as long as the genetic manipulation does not change functional properties, in particular does not interfere with the ability of the hepatitis B virus core antigen protein to assemble into virus-like particles.

In a particularly preferred embodiment, 100% of the protein subunits making up the virus-like particle of the invention are the protein of the present invention. Thus, in a particularly preferred embodiment, the virus-like particle of the present invention is composed of multiple copies of the protein of the present invention. The single proteins making up the virus-like particle may comprise the same or different epitopes derived from a single or different tumor-associated antigens. They may also comprise the same or a different HBcAg portion, or the same or a different HBcAg backbone.

In another aspect, the present invention provides an immunogenic composition comprising the protein of the present invention, the nucleic acid of the present invention, the vector of the present invention, the host cell of the present invention, or the virus-like particle of the present invention and a pharmaceutically acceptable diluent, carrier, and/or excipient. Preferably, the immunogenic composition is for eliciting an immune response, preferably a humoral immune response against the tumor-associated antigen in association with the surface of a cell in a subject, wherein the tumor-associated antigen is preferably a self-protein in said subject. It is particularly preferred that the immunogenic composition of the present invention is free of adjuvants. Preferably, the immunogenic effect of the immunogenic composition of the present invention, for example, the generation of autoantibodies against the tumor-associated antigen from which the epitope is derived, can be also observed when administered to a subject without the addition of adjuvants. However, the addition of adjuvants as described above may increase and/or prolong the immunogenic effect.

In other aspects, the present invention provides the protein of the present invention, the nucleic acid of the present invention, the vector of the present invention, the host cell of the present invention, the virus-like particle of the present invention, or the immunogenic composition of the present invention for prophylactic and/or therapeutic treatment of tumors. In general, the tumors in the context of the present invention are preferably tumors associated with expression or abnormal expression of a tumor-associated antigen, wherein the tumor-associated antigen is as defined above. For example, the tumor-associated antigen is a differentiation antigen, a cancer/testis antigen, an antigen specific for trophoblastic tissues, or a germ line specific antigen. Preferably, the protein of the present invention, the nucleic acid of the present invention, the vector of the present invention, the host cell of the present invention, the virus-like particle of the present invention, or the immunogenic composition of the present invention is for prophylactic and/or therapeutic treatment of a disease associated with expression or abnormal expression of a tumor-associated antigen, wherein the epitope comprised by the protein of the present invention, the nucleic acid of the present invention, the vector of the present invention, the host cell of the present invention, the virus-like particle of the present invention, or the immunogenic composition of the present invention is derived from said tumor-associated antigen.

For example, if the protein of the present invention, the nucleic acid of the present invention, the vector of the present invention, the host cell of the present invention, the virus-like particle of the present invention, or the immunogenic composition of the present invention comprises an epitope derived from CLDN6, the protein of the present invention, the nucleic acid of the present invention, the vector of the present invention, the host cell of the present invention, the virus-like particle of the present invention, or the immunogenic composition of the present invention is for prophylactic and/or therapeutic treatment of a disease associated with expression or abnormal expression of CLDN6, for example, a tumorigenic disease as described above. Preferably, the tumorigenic disease is a cancer disease, preferably selected from the group consisting of ovarian cancer, in particular ovarian adenocarcinoma and ovarian teratocarcinoma, lung cancer, including small cell lung cancer (SCLC) and non-small cell lung cancer (NSCLC), in particular squamous cell lung carcinoma and adenocarcinoma, gastric cancer, breast cancer, hepatic cancer, pancreatic cancer, skin cancer, in particular basal cell carcinoma and squamous cell carcinoma, malignant melanoma, head and neck cancer, in particular malignant pleomorphic adenoma, sarcoma, in particular synovial sarcoma and carcinosarcoma, bile duct cancer, cancer of the urinary bladder, in particular transitional cell carcinoma, kidney cancer, in particular renal cell carcinoma including clear cell renal cell carcinoma and papillary renal cell carcinoma, colon cancer, testicular embryonal carcinoma, and placental choriocarcinoma, and the metastatic forms thereof. It is particularly preferred that the cancer disease is selected from the group consisting of ovarian cancer, lung cancer, metastatic ovarian cancer and metastatic lung cancer. Preferably, the ovarian cancer is a carcinoma or an adenocarcinoma. Preferably, the lung cancer is a carcinoma or an adenocarcinoma, and preferably is bronchiolar cancer such as a bronchiolar carcinoma or bronchiolar adenocarcinoma.

Furthermore, for example, if the protein of the present invention, the nucleic acid of the present invention, the vector of the present invention, the host cell of the present invention, the virus-like particle of the present invention, or the immunogenic composition of the present invention comprises an epitope derived from CLDN18.2, the protein of the present invention, the nucleic acid of the present invention, the vector of the present invention, the host cell of the present invention, the virus-like particle of the present invention, or the immunogenic composition of the present invention is for prophylactic and/or therapeutic treatment of a disease associated with expression or abnormal expression of CLDN18.2, for example, a tumorigenic disease as described above. Preferably, the tumorigenic disease is a cancer, preferably a cancer selected from the group consisting of gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

Furthermore, for example, if the protein of the present invention, the nucleic acid of the present invention, the vector of the present invention, the host cell of the present invention, the virus-like particle of the present invention, or the immunogenic composition of the present invention comprises an epitope derived from PLAC1, the protein of the present invention, the nucleic acid of the present invention, the vector of the present invention, the host cell of the present invention, the virus-like particle of the present invention, or the immunogenic composition of the present invention is for prophylactic and/or therapeutic treatment of a disease associated with expression or abnormal expression of PLAC1, for example, a tumorigenic disease. Preferably, the tumorigenic disease is a cancer, preferably a cancer selected from the group consisting of breast cancer, lung cancer, gastric cancer, ovarian cancer, hepatocellular cancer, colon cancer, pancreatic cancer, esophageal cancer, head & neck cancer, kidney cancer, in particular renal cell carcinoma, prostate cancer, liver cancer, melanoma, sarcoma, myeloma, neuroblastoma, placental choriocarcinoma, cervical cancer, and thyroid cancer, and the metastatic forms thereof.

In another aspect, the present invention provides a method for eliciting an immune response, preferably a humoral immune response, against a tumor-associated antigen in a subject, wherein the tumor-associated antigen is preferably a self-protein in said subject, said method comprising administering to said subject the protein of the present invention, the nucleic acid of the present invention, the vector of the present invention, the host cell of the present invention, the virus-like particle of the present invention, or the immunogenic composition of the present invention. Preferably, said subject is afflicted with a tumor or is at risk of developing a tumor, said tumor being preferably characterized by association of the tumor-associated antigen with the surface of a tumor cell. Preferably, said tumor is associated with the tumor-associated antigen of which the epitope is derived which is comprised by the protein of the present invention, the nucleic acid of the present invention, the vector of the present invention, the host cell of the present invention, the virus-like particle of the present invention, or the immunogenic composition of the present invention. In a preferred embodiment, the method comprises administering the virus-like particle or the immunogenic composition of the present invention. Preferably, eliciting a humoral immune response comprises the generation of antibodies, preferably autoantibodies, which specifically recognize/bind to the tumor-associated antigen from which the epitope is derived in association with the surface of a cell, preferably on the surface of a living cell, for example, a tumor cell which carries/expresses the tumor-associated antigen. Preferably, the generated antibodies recognize the tumor-associated antigen in its native conformation on the surface of a cell. It is particularly preferred that the generated antibodies are capable of eliciting effector functions against cells carrying the tumor-associated antigen from which the epitope is derived on their surface. For example, the generated antibodies may be capable of mediating ADCC and/or CDC against such cells and/or they may directly induce apoptosis in or inhibit proliferation of the cells carrying the tumor-associated antigen on their surface. Preferably, in this aspect of the present invention, the immune response, preferably the humoral immune response, results in reduction, preferably inhibition of tumor growth, and most preferably in regression of the tumor in the subject.

In a further aspect, the present invention provides a method for breaking self-tolerance towards a tumor-associated antigen in a subject, said method comprising administering to said subject the protein of the present invention, the nucleic acid of the present invention, the vector of the present invention, the host cell of the present invention, the virus-like particle of the present invention, or the immunogenic composition of the present invention. Preferably, breaking the self-tolerance is with respect to the tumor-associated antigen from which the epitope is derived which is comprised by the protein of the present invention, the nucleic acid of the present invention, the vector of the present invention, the host cell of the present invention, the virus-like particle of the present invention, or the immunogenic composition of the present invention.

In another aspect, the present invention provides a method for treating and/or preventing a tumor in a subject, said method comprising administering to said subject the protein of the present invention, the nucleic acid of the present invention, the vector of the present invention, the host cell of the present invention, the virus-like particle of the present invention, or the immunogenic composition of the present invention. Preferably, said tumor is associated with expression or abnormal expression the tumor-associated antigen from which the epitope is derived that is comprised in the protein of the present invention, the nucleic acid of the present invention, the vector of the present invention, the host cell of the present invention, the virus-like particle of the present invention, or the immunogenic composition of the present invention. The particular preferred tumor types treated and/or prevented are as described herein, in particular, as described for the exemplary tumor-associated antigens CLDN6, CLDN18.2, and PLAC1.

In preferred embodiments of the methods and uses of the present invention the protein of the present invention, the nucleic acid of the present invention, the vector of the present invention, the host cell of the present invention, the virus-like particle of the present invention, or the immunogenic composition of the present invention is administered without adjuvant.

The present invention also provides the use of the protein of the present invention, the nucleic acid of the present invention, the vector of the present invention, the host cell of the present invention, the virus-like particle of the present invention, or the immunogenic composition of the present invention for the preparation of a medicament for prophylactic and/or therapeutic treatment of a tumor, for eliciting a humoral immune response against a tumor-associated antigen in a subject, wherein the tumor-associated antigen is a self-protein in said subject, or for breaking self-tolerance towards a tumor-associated antigen in a subject. In this context, the above described embodiments also apply to this aspect of the present invention.

For all the above methods and uses, the protein of the present invention, the nucleic acid of the present invention, the vector of the present invention, the host cell of the present invention, the virus-like particle of the present invention, or the immunogenic composition of the present invention is preferably administered to a subject in need thereof in a therapeutically effective amount. It is preferred that the compounds and compositions described herein are administered orally, buccally, sublingually, intranasally, via pulmonary routes such as by inhalation, via rectal routes, or parenterally, for example, intracavernosally, intravenously, intra-arterially, intraperitoneally, intrathecally, intraventricularly, intra-urethrally intrasternally, intracranially, intramuscularly, intradermally, intranodally, or subcutaneously. Administration may be by infusion or needleless injection techniques. Preferably, the compounds or compositions described herein are administered parenterally. A composition suitable for parenteral administration is best used in the form of a sterile aqueous solution which may contain other substances, for example, enough salts or glucose to make the solution isotonic with blood. The aqueous solutions should be suitably buffered (preferably to a pH of from 3 to 9), if necessary.

All methods and uses of the present invention preferably aim at the prophylactic and/or therapeutic treatment of a tumorigenic disease as described herein above. In some embodiments, said methods and uses of the present invention may be combined with conventional tumor therapy, such as surgery, radiation therapy, chemotherapy, and/or passive immunization with monoclonal antibodies. For example, the compounds, compositions, methods, or uses of the present invention may be applied after surgical removal of the primary tumor in order to target tumor cells that have not been excised and/or to prevent formation of metastasis. The compounds and compositions described herein may also be part of a composition used for chemotherapy, for example, they may be comprised by a conventional chemotherapeutic composition.

The present inventors have achieved to provide means for active immunization of a subject against tumorigenic diseases which are associated with the expression or abnormal expression of tumor-associated antigens, which are self-proteins in said subject, and thus, provide means and methods for preventing and/or treating such tumorigenic diseases.

The present invention is described in detail by the figures and examples below, which are used only for illustration purposes and are not meant to be limiting. Owing to the description and the examples, further embodiments which are likewise included in the invention are accessible to the skilled worker.

EXAMPLES

Generation of the HBcAg-VLP Based Vaccines

For recombinant generation of chimeric HBcAg fusion proteins various bacterial expression vectors (HBcAg backbones) have been generated, which differ regarding the epitope insertion sites within the HBcAg sequence. In any of the generated HBcAg backbones epitopes may be inserted in specific regions of the HBcAg MIR. With the exception of the HBcAg backbones HBcAg Del 79-80 linker and HBcAg Del 79-80 epitopes may additionally be attached to the amino-terminus or inserted into the amino-terminal part of the HBcAg protein, for example, between the SalI and SpeI restriction sites (FIG. 1). The wild type sequence of the N-terminal part of the HBc gene subtype awy is MDIDPYK. The insertion of the restriction sites SalI and SpeI leads to the sequence M VDAATS DIDPYK, wherein the alanines are needed for the separation of the restriction sites. The insertion of an epitope (xxx) between the restriction sites SalI and SpeI would result in the sequence M VE xxx SS DIDPYK. The DNA sequences of the fusion proteins have been sequence-optimized for the expression in $E.\ coli$. Appropriate recognition sequences for restriction enzymes have been integrated in the expression cassettes for the fusion protein, which allow replacing or integrating the various regions of the cassette or the epitope to be inserted without major effort (cf. FIGS. 1 and 7).

CLDN6, CLDN18.2, and PLAC1 epitopes, respectively, either have been directly inserted into the HBcAg MIR (HBcAg backbone HBcAg Del 79-80), or have been flanked amino- and carboxy-terminally by a glycine/serine ($G_4SG_4$) linker for increasing epitope flexibility during protein folding. Furthermore, a sequence coding for a histidine tag (His-tag) has been integrated at the 3'-end of the expression cassette allowing a subsequent purification of the fusion protein under GMP conditions using affinity chromatography (cf. FIG. 1). The utilized HBcAg sequences are 3'-truncated variants which code for a C-terminally truncated HBcAg protein (aa 1-150). This variant is capable of assembling into VLPs and is not able to bind nucleic acids in contrast to the wild-type HBcAg (aa 1-183) preventing a potential contamination of the vaccine with bacterial nucleic acids.

After expression of the chimeric HBcAg fusion constructs in $E.\ coli$ the fusion proteins have been purified in their dimeric form under denaturing conditions using immobilized metal ion affinity chromatography. Subsequently the in vitro assembly of the fusion proteins into VLPs has been performed using dialysis against high salt buffer and a final sucrose density gradient ultracentrifugation step for further purification and concentration of assembled VLPs. The successful reassembly and quality of the VLPs has been verified using native protein agarose gel electrophoresis and negative contrast transmission electron microscopy (cf. FIG. 2). It has been verified that specific epitopes of the tumor antigens CLDN6, CLDN18.2, and PLAC1 may be inserted into HBcAg without interfering with the assembly competence of HBcAg into VLPs. The fusion proteins which have been purified using denaturing methods have been in vitro assembled into highly pure VLPs which did not differ in their electron microscopic appearance from wild-type HBcAg VLPs. The results of further immunization experiments are subsequently exemplarily shown for the following chimeric HBcAg VLPs (cf. FIG. 8):

HBcAg Del 79-80 linker CLDN18.2-EC1 short (SEQ ID NOs: 37 and 41): Fusion protein consisting of an amino- and carboxy-terminal HBcAg domain (expression vector HBcAg Del 79-80), an inserted and glycine linker flanked CLDN18.2 epitope (TQDLYNNPVT; SEQ ID NO: 21) of the extracellular domain 1 (EC1) and a C-terminal His-tag.

HBcAg Del 79-80 CLDN18.2-EC1 short (SEQ ID NOs: 38 and 42): Fusion protein consisting of an amino-terminal and carboxy-terminal HBcAg domain (expression vector HBcAg Del 79-80), an inserted CLDN18.2 epitope (TQDLYNNPVT; SEQ ID NO: 21) of the extracellular domain 1 (EC1), and a C-terminal His-tag.

HBcAg Del 79-80 linker PLAC1 $3^{rd}$ Loop A (SEQ ID NOs: 39 and 43): Fusion protein consisting of an amino-terminal and carboxy-terminal HBcAg domain (expression vector HBcAg Del 79-80), an inserted and glycine linker flanked PLAC1 epitope (VFSEEEHTQVP; SEQ ID NO: 22) of the predicted third PLAC1 protein loop and a C-terminal His-tag.

HBcAg Del 79-80 PLAC1 $3^{rd}$ Loop B (SEQ ID NOs: 40 and 44): Fusion protein consisting of an amino-terminal and carboxy-terminal HBcAg domain (expression vector HBcAg Del 79-80), an inserted PLAC1 epitope (VFSEEEHTQV; SEQ ID NO: 23) of the predicted third PLAC1 protein loop and a C-terminal His-tag.

Verification of the Chimeric HBcAg-VLP Based Vaccines

For verification of the general various species spanning immunogenicity and antigenicity of the purified chimeric HBcAg VLPs they have been applied to NZW rabbits and Balb/c mice (only CLDN18.2 epitope carrying VLPs), respectively. The immunization studies have been carried out with and without addition of adjuvants.

The sequence of the CLDN18.2 epitope (SEQ ID NO: 21) is identical to the respective region of the endogenously expressed protein in rabbit and mouse. The induction of an antibody response against CLDN18.2 thus would indicate the breaking of self-tolerance in the respective organism. Indirect immunofluorescence assays (IF) as well as flow cytometric analyses (FACS) have been used as read-out for characterization and validation of the induced humoral immune responses.

CHO cells transiently transfected with CLDN18.2 and PLAC1, respectively, have been used for indirect IFs. The cells have been fixed on slides, permeabilized in some cases (only for CLDN18.2), and incubated subsequently with the respective polyclonal antisera. The immunological detection of bound antibodies has been carried out using fluorescence labeled secondary antibodies. Non-transfected CHO cells or transfected CHO cells only incubated with secondary antibodies have been used as negative controls. Furthermore, the CLDN18.2 directed polyclonal antisera have been tested regarding their specificity using CHO cells which have been transfected with CLDN18.1, a splice variant of CLDN18 which differs from CLDN18.2 in the amino-terminal amino acids 1-69 (cf. FIG. 3).

It is shown that the generated polyclonal antisera were able to recognize the respective targeted surface antigens in their native conformation and that these antibodies can bind to said surface antigens (exemplarily shown in FIG. 3 for CLDN18.2 and PLAC1). It was irrelevant whether the immunogens have been applied with or without adjuvants. Furthermore, it is demonstrated for the CLDN18.2 epitope carrying HBcAg VLPs that they are capable of breaking self-tolerance in two different species. Furthermore, the antisera which have been generated by immunization with the CLDN18.2 epitope exhibited an isoform specific immune reactivity against CLDN18.2 transfected cells.

FACS analyses have been performed as a further approach for verifying the immunoreactivity of the generated polyclonal antisera (exemplarily shown for CLDN18.2; cf. FIG. 4). Contrary to the indirect IF, however, the cells neither have been fixed nor permeabilized in these experiments. The detection of the antigens is thus carried out in the native conformation on live cells. Furthermore, cells endogenously expressing the targeted tumor-associated antigen have been used, whereby it has been verified whether the generated antisera are able to detect physiological densities of tumor-associated antigen epitopes (cf. FIG. 4).

It is shown that the generated CLDN18.2 directed polyclonal antisera were able to detect endogenously expressed antigens and to specifically bind the protein in its native conformation on live cells. It has been verified that the existing B cell tolerance against the self protein can be broken by active vaccination, wherein the addition of adjuvants to the immunogen was irrelevant.

Besides the recognition of the native conformation of the targeted cell surface antigen, the induction of antibodies with therapeutically effective effector functions is of utmost importance for a successful active immunization strategy. Antibody effector functions are on the one hand cytotoxic effects, e.g., complement dependent cytotoxicity (CDC) or antibody dependent cellular cytotoxicity (ADCC) as well as antibody-mediated anti-proliferative effects. Luciferase based CDC and ADCC assays, respectively, have been used for the analysis of cytotoxic effector functions of the CLDN18.2 directed polyclonal antisera. It is shown that the antisera generated in two different species exhibited CDC as well as ADCC effector functions which were specifically directed against the CLDN18.2 isoform. Polyclonal antisera which have been induced by immunization with HBcAg wild-type VLPs (without inserted antigen epitopes) or Keyhole Limpet Hemocyanin (KLH)-conjugated CLDN18.2 peptides (which have been identical to the epitopes inserted in the chimeric HBcAg VLPs) in combination with adjuvants did not exhibit any cytotoxic effector functions (cf. FIG. 5).

Previous studies have been shown that the expression of PLAC1 is supporting proliferation. Thus, the PLAC1 directed polyclonal antisera which have been generated by active immunization have been analyzed regarding proliferation inhibiting effector functions. To this end, endogenously PLAC1 expressing cells (MCF-7) as well as PLAC1 negative cells (MelHO) have been incubated with polyclonal PLAC1 directed antisera for 72 hours and subsequently a 5-bromo-2'-deoxyuridine (BrdU) based proliferation assay has been performed. A monoclonal antibody directed against the oncogene myc and a polyclonal antiserum against CLDN18.2 which has been generated by active vaccination with chimeric HBcAg VLPs, have been used as controls. It is shown that only the PLAC1-directed polyclonal antisera mediated dosage-dependent PLAC1-specific anti-proliferative effects. Thus, besides cytotoxic effector functions also anti-proliferative antibody effector functions may be generated by active immunization using chimeric HBcAg VLPs (cf. FIG. 6).
Immunization with HBcAg CLDN18.2-EC1 Short-VLPs The potency of chimeric VLPs to induce antibody responses against the inserted CLDN18.2 epitope was analyzed by immunization of mice and rabbits. Importantly, the selected epitope and the tissue distribution of the orthologous proteins with strict restriction to short lived gastric cells are conserved in all three species.

An almost maximal anti-target humoral immune response as measured by flow cytometry was observed after only two immunizations, irrespective of the immunization route or applied adjuvants. Analysis of the target-specific antibody response revealed that anti-target antibody reactivity decreased over time and was back to background levels approximately two months after the third vaccination (vaccination at d0, d10 and d28). However, when a booster was given at d102, the auto-antibody reactivity to the target increased rapidly, suggesting existence of immune memory for auto-antibody production. Moreover, this data indicates that induction of target-specific auto-antibodies by booster immunizations are feasible and that the anti-HBcAg directed immunity had not taken over.

In a further experiment, partly related to the question of antibody response drift, it could be demonstrated that a pre-existing immune response against the HBcAg-carrier molecule does not abrogate the ability of HBcAg Del 79-80 linker CLDN18.2-EC1 short-VLPs to induce target-specific auto-antibody responses. Thus, potentially existing carrier induced epitopic suppression (CIES) can be overcome, indicating that the immunogenicity of the CLDN18.2 epitope displayed at high density on the surface of the HBcAg carrier (240 CLDN18.2 epitopes per VLP molecule) is in this context comparable to the backbone itself.

BALB/c mice were immunized with HBcAg Del 79-80 CLDN18.2-EC1 short-, HBcAg Del 79-80 linker CLDN18.2-EC1 short-VLPs or with KLH-conjugated linear CLDN18.2$_{32-41}$ peptide as control and antibody reactivity against the linear CLDN18.2$_{32-41}$ peptide or the HBcAg backbone was determined by measuring ELISA endpoint titer. Different immunization protocols were applied, varying the adjuvant, administration route and immunogen amount each to groups of 3-5 mice.

It was observed that sera from mice immunized with HBcAg Del 79-80 linker CLDN18.2-EC1 short-VLPs displayed a higher specific reactivity against the linear BSA-conjugated CLDN18.2$_{32-41}$ peptide as compared to mice in other groups. Interestingly, mice immunized s.c. with HBcAg Del 79-80 linker CLDN18.2-EC1 short-VLPs without the addition of adjuvant revealed the highest mean endpoint titer against the peptide. All VLPs induced antibodies against the HBcAg backbone with similar endpoint titers. Heat denaturation of chimeric VLPs abrogated their capability to induce peptide-binding antibodies without compromising development of antibodies against the backbone.

Of the mice vaccinated with HBcAg Del 79-80 linker CLDN18.2-EC1 short-VLPs ~90% were shown to recognize the linear CLDN18.2 epitope in ELISA. One third of these were able to bind to the native CLDN18.2 molecule on transfectants as analyzed by FACS. In rabbits all sera of animals vaccinated with HBcAg Del 79-80 linker CLDN18.2-EC1 short-VLPs were able to recognize the linear epitope as well as the native protein. When using CLDN18.1 transfectants as control, no cross reactivity with this variant was observed.

Compared to HBcAg Del 79-80 CLDN18.2-EC1 short-VLPs, HBcAg Del 79-80 linker CLDN18.2-EC1 short-VLPs were clearly superior in eliciting auto-antibodies, which recognize the native protein in physiological densities on the surface of endogenously expressing tumor cells.

Prophylactic Vaccination with HBcAg Del 79-80 Linker CLDN18.2-EC1 Short-VLPs Confers Partial Protection in an Immunocompetent Syngeneic Mouse Tumor Model To evaluate prophylactic in vivo efficacy of HBcAg Del 79-80 linker CLDN18.2-EC1 short-VLPs, a syngeneic tumor model in immunocompetent BALB/c mice in which pulmonary metastasis formation was induced by i.v. application of CT26 colonic cancer cells stably transduced with murine CLDN18.2 was used.

BALB/c mice were vaccinated three times (day 1, day 14, day 28) with 50 µg C-terminally truncated (amino acids 1-150) HBcAg (HBcAgΔ)-VLPs, HBcAg Del 79-80 linker CLDN18.2-EC1 short-VLPs, or PBS as control, all formulated in AbISCO-100 (Isconova). Two weeks after the last immunization 1×10$^5$ syngeneic CT26 colon cancer cells stably expressing murine CLDN18.2 were administered into the tail vein. Thirteen days later mice were sacrificed and lungs weighed and subjected to microscopic analysis to assess load of pulmonary metastases. Statistical analysis of lung weights was performed by ANOVA followed by Tukey test. For histopathological assessment, three µm thick sections of formalin fixed and paraffin embedded lungs were deparaffinized and rehydrated, followed by heat induced epitope retrieval in citrate buffer at pH 6. After quenching of endogenous peroxidases by $H_2O_2$, unspecific antibody binding sites were blocked with 10% goat serum, followed by overnight incubation with polyclonal rabbit anti-CLDN18 (Mid) (Invitrogen) at 4° C. For detection of binding, a HRP-conjugated secondary antibody (BrightVision Poly-HRP-Anti-rabbit, Immunologic) and the Vector NovaRED™ kit (Vector Laboratories) were used. After hematoxylin counterstaining, dehydration and mounting, sections were documented using a MIRAX SCAN (Zeiss). Ratios of tumor and normal tissue areas were determined using ImageJ Software v.1.44. Statistical differences between groups were assessed by ANOVA followed by Dunn's test.

Macroscopic analysis of lungs derived from mice vaccinated with HBcAg Del 79-80 linker CLDN18.2-EC1 short-VLPs revealed a smaller number of metastatic nodules as compared to HBcAgΔ-VLPs or PBS control groups (FIG. 9A) and significantly lower lung weights close to those of mice not challenged with tumor cells (FIG. 9B). Moreover, the percentage of cancerous tissue area per whole lung section as calculated after visualizing CT26-CLDN18.2 pulmonary metastases by IHC-staining for CLDN18.2 was significantly ($p<0.05$) smaller as compared to mice vaccinated with HBcAgΔ-VLPs or PBS control groups (FIG. 9C, 9D).

In conclusion, these data show that prophylactic vaccination with HBcAg Del 79-80 linker CLDN18.2-EC1 short-VLPs mediates protection against highly malignant/tumorigenic CT26-CLDN18.2 cells.

In summary, the developed chimeric HBcAg VLPs fulfill all requirements for the use in an active immunotherapeutically effective tumor vaccination. It has been shown that by administration of the chimeric HBcAg VLPs, antibodies can be generated in a subject against tumor-associated antigens which are self-proteins in said subject, and that the induced antisera mediate therapeutically effective effector functions.

SEQUENCE LISTING

<160> NUMBER OF SEQ ID NOS: 80

<210> SEQ ID NO 1
<211> LENGTH: 183
<212> TYPE: PRT
<213> ORGANISM: Hepatitis B virus

<400> SEQUENCE: 1

```
Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Lys Ser Arg Glu Ser Gln Cys
            180
```

<210> SEQ ID NO 2
<211> LENGTH: 552
<212> TYPE: DNA
<213> ORGANISM: Hepatitis B virus

<400> SEQUENCE: 2

```
atggacatcg acccttataa agaatttgga gctactgtgg agttactctc gttttgcct      60 tctgacttct ttccttcagt acgagatctt ctagataccg cctcagctct gtatcgggaa    120
gccttagagt ctcctgagca ttgttcacct caccatactg cactcaggca agcaattctt    180
tgctgggggg aactaatgac tctagctacc tgggtgggtg ttaatttgga agatccagcg    240
tctagagacc tagtagtcag ttatgtcaac actaatatgg cctaaagtt caggcaactc     300 ttgtggtttc acatttcttg tctcactttt ggaagagaaa cagttataga gtatttggtg    360
tctttcggag tgtggattcg cactcctcca gcttatagac caccaaatgc ccctatccta    420
tcaacacttc cggagactac tgttgttaga cgacgaggca ggtccctag aagaagaact     480 cccctcacctc gcagacgaag gtctcaatcg ccgcgtcgca aagatctaa atctcgggaa    540 tctcaatgtt ag                                                        552
```

<210> SEQ ID NO 3
<211> LENGTH: 220
<212> TYPE: PRT
<213> ORGANISM: Homo sapiens

<400> SEQUENCE: 3

```
Met Ala Ser Ala Gly Met Gln Ile Leu Gly Val Val Leu Thr Leu Leu
1               5                   10                  15
Gly Trp Val Asn Gly Leu Val Ser Cys Ala Leu Pro Met Trp Lys Val
            20                  25                  30
Thr Ala Phe Ile Gly Asn Ser Ile Val Val Ala Gln Val Val Trp Glu
        35                  40                  45
Gly Leu Trp Met Ser Cys Val Val Gln Ser Thr Gly Gln Met Gln Cys
    50                  55                  60
Lys Val Tyr Asp Ser Leu Leu Ala Leu Pro Gln Asp Leu Gln Ala Ala
65                  70                  75                  80
Arg Ala Leu Cys Val Ile Ala Leu Leu Val Ala Leu Phe Gly Leu Leu
                85                  90                  95
Val Tyr Leu Ala Gly Ala Lys Cys Thr Thr Cys Val Glu Glu Lys Asp
            100                 105                 110
Ser Lys Ala Arg Leu Val Leu Thr Ser Gly Ile Val Phe Val Ile Ser
        115                 120                 125
Gly Val Leu Thr Leu Ile Pro Val Cys Trp Thr Ala His Ala Ile Ile
    130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Gly Ser Gln Gly
            180                 185                 190
Pro Ser His Tyr Met Ala Arg Tyr Ser Thr Ser Ala Pro Ala Ile Ser
        195                 200                 205
Arg Gly Pro Ser Glu Tyr Pro Thr Lys Asn Tyr Val
210                 215                 220
```

<210> SEQ ID NO 4
<211> LENGTH: 663
<212> TYPE: DNA
<213> ORGANISM: Homo sapiens

<400> SEQUENCE: 4

```
atggcctctg ccggaatgca gatcctggga gtcgtcctga cactgctggg ctgggtgaat    60
ggcctggtct cctgtgccct gcccatgtgg aaggtgaccg ctttcatcgg caacagcatc   120
gtggtggccc aggtggtgtg ggagggcctg tggatgtcct gcgtggtgca gagcaccggc   180
cagatgcagt gcaaggtgta cgactcactg ctggcgctgc cacaggacct gcaggctgca   240
cgtgccctct gtgtcatcgc cctccttgtg gccctgttcg gcttgctggt ctaccttgct   300
ggggccaagt gtaccacctg tgtggaggag aaggattcca aggcccgcct ggtgctcacc   360
tctgggattg tctttgtcat ctcaggggtc ctgacgctaa tccccgtgtg ctggacggcg   420
catgccatca tccgggactt ctataacccc ctggtggctg aggcccaaaa gcgggagctg   480
ggggcctccc tctacttggg ctgggcggcc tcaggccttt tgttgctggg tggggggttg   540
ctgtgctgca cttgccccts ggggggggtcc cagggcccca gccattacat ggcccgctac   600
tcaacatctg ccctgccat ctctcggggg ccctctgagt accctaccaa gaattacgtc   660
tga                                                                  663
```

<210> SEQ ID NO 5

```
<211> LENGTH: 261
<212> TYPE: PRT
<213> ORGANISM: Homo sapiens

<400> SEQUENCE: 5

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260

<210> SEQ ID NO 6
<211> LENGTH: 786
<212> TYPE: DNA
<213> ORGANISM: Homo sapiens

<400> SEQUENCE: 6
atggccgtga ctgcctgtca gggcttgggg ttcgtggttt cactgattgg gattgcgggc      60
atcattgctg ccacctgcat ggaccagtgg agcacccaag acttgtacaa caaccccgta     120
acagctgttt tcaactacca ggggctgtgg cgctcctgtg tccgagagag ctctggcttc     180
accgagtgcc ggggctactt caccctgctg ggcctgccag ccatgctgca ggcagtgcga     240
gccctgatga tcgtaggcat cgtcctgggt gccattggcc tcctggtatc catctttgcc     300
ctgaaatgca tccgcattgg cagcatggag gactctgcca aagccaacat gacactgacc     360
tccgggatca tgttcattgt ctcaggtctt tgtgcaattg ctggagtgtc tgtgtttgcc     420
```

-continued

```
aacatgctgg tgactaactt ctggatgtcc acagctaaca tgtacaccgg catgggtggg    480
atggtgcaga ctgttcagac caggtacaca tttggtgcgg ctctgttcgt gggctgggtc    540
gctggaggcc tcacactaat tggggtgtg atgatgtgca tcgcctgccg gggcctggca    600
ccagaagaaa ccaactacaa agccgtttct tatcatgcct caggccacag tgttgcctac    660
aagcctggag gcttcaaggc cagcactggc tttgggtcca acaccaaaaa caagaagata    720
tacgatggag gtgcccgcac agaggacgag gtacaatctt atccttccaa gcacgactat    780
gtgtaa                                                                786
```

<210> SEQ ID NO 7
<211> LENGTH: 212
<212> TYPE: PRT
<213> ORGANISM: Homo sapiens

<400> SEQUENCE: 7

```
Met Lys Val Phe Lys Phe Ile Gly Leu Met Ile Leu Leu Thr Ser Ala
1               5                   10                  15

Phe Ser Ala Gly Ser Gly Gln Ser Pro Met Thr Val Leu Cys Ser Ile
            20                  25                  30

Asp Trp Phe Met Val Thr Val His Pro Phe Met Leu Asn Asn Asp Val
        35                  40                  45

Cys Val His Phe His Glu Leu His Leu Gly Leu Gly Cys Pro Pro Asn
    50                  55                  60

His Val Gln Pro His Ala Tyr Gln Phe Thr Tyr Arg Val Thr Glu Cys
65                  70                  75                  80

Gly Ile Arg Ala Lys Ala Val Ser Gln Asp Met Val Ile Tyr Ser Thr
                85                  90                  95

Glu Ile His Tyr Ser Ser Lys Gly Thr Pro Ser Lys Phe Val Ile Pro
            100                 105                 110

Val Ser Cys Ala Ala Pro Gln Lys Ser Pro Trp Leu Thr Lys Pro Cys
        115                 120                 125

Ser Met Arg Val Ala Ser Lys Ser Arg Ala Thr Ala Gln Lys Asp Glu
    130                 135                 140

Lys Cys Tyr Glu Val Phe Ser Leu Ser Gln Ser Ser Gln Arg Pro Asn
145                 150                 155                 160

Cys Asp Cys Pro Pro Cys Val Phe Ser Glu Glu Glu His Thr Gln Val
                165                 170                 175

Pro Cys His Gln Ala Gly Ala Gln Glu Ala Gln Pro Leu Gln Pro Ser
            180                 185                 190

His Phe Leu Asp Ile Ser Glu Asp Trp Ser Leu His Thr Asp Asp Met
        195                 200                 205

Ile Gly Ser Met
    210
```

<210> SEQ ID NO 8
<211> LENGTH: 639
<212> TYPE: DNA
<213> ORGANISM: Homo sapiens

<400> SEQUENCE: 8

```
atgaaagttt ttaagttcat aggactgatg atcctcctca cctctgcgtt ttcagccggt    60
tcaggacaaa gtccaatgac tgtgctgtgc tccatagact ggttcatggt cacagtgcac    120
cccttcatgc taaacaacga tgtgtgtgta cactttcatg aactacactt gggcctgggt    180 tgcccccaa accatgttca gccacacgcc taccagttca cctaccgtgt tactgaatgt    240
```

-continued

```
ggcatcaggg ccaaagctgt ctctcaggac atggttatct acagcactga gatacactac    300
tcttctaagg gcacgccatc taagtttgtg atcccagtgt catgtgctgc ccccaaaag     360 tccccatggc tcaccaagcc ctgctccatg agagtagcca gcaagagcag gccacagcc     420 cagaaggatg agaaatgcta cgaggtgttc agcttgtcac agtccagtca aaggcccaac    480
tgcgattgtc caccttgtgt cttcagtgaa gaagagcata cccaggtccc ttgtcaccaa    540 gcagggctc aggaggctca acctctgcag ccatctcact ttcttgatat ttctgaggat     600
tggtctcttc acacagatga tatgattggg tccatgtga                           639
```

<210> SEQ ID NO 9
<211> LENGTH: 13
<212> TYPE: PRT
<213> ORGANISM: Artificial
<220> FEATURE:
<223> OTHER INFORMATION: CLDN6 epitope
<400> SEQUENCE: 9

```
Pro Met Trp Lys Val Thr Ala Phe Ile Gly Asn Ser Ile
1               5                   10
```

<210> SEQ ID NO 10
<211> LENGTH: 15
<212> TYPE: PRT
<213> ORGANISM: Artificial
<220> FEATURE:
<223> OTHER INFORMATION: CLDN6 epitope
<400> SEQUENCE: 10

```
Met Trp Lys Val Thr Ala Phe Ile Gly Asn Ser Ile Val Val Ala
1               5                   10                  15
```

<210> SEQ ID NO 11
<211> LENGTH: 14
<212> TYPE: PRT
<213> ORGANISM: Artificial
<220> FEATURE:
<223> OTHER INFORMATION: CLDN6 epitope
<400> SEQUENCE: 11

```
Phe Ile Gly Asn Ser Ile Val Val Ala Gln Val Val Trp Glu
1               5                   10
```

<210> SEQ ID NO 12
<211> LENGTH: 13
<212> TYPE: PRT
<213> ORGANISM: Artificial
<220> FEATURE:
<223> OTHER INFORMATION: CLDN6 epitope
<400> SEQUENCE: 12

```
Val Val Ala Gln Val Val Trp Glu Gly Leu Trp Met Ser
1               5                   10
```

<210> SEQ ID NO 13
<211> LENGTH: 23
<212> TYPE: PRT
<213> ORGANISM: Artificial
<220> FEATURE:
<223> OTHER INFORMATION: CLDN6 epitope
<400> SEQUENCE: 13

```
Val Ala Gln Val Val Trp Glu Gly Leu Trp Met Ser Cys Val Val Gln
1               5                   10                  15
```

Ser Thr Gly Gln Met Gln Cys
            20

<210> SEQ ID NO 14
<211> LENGTH: 16
<212> TYPE: PRT
<213> ORGANISM: Artificial
<220> FEATURE:
<223> OTHER INFORMATION: CLDN6 epitope

<400> SEQUENCE: 14

Lys Val Thr Ala Phe Ile Gly Asn Ser Ile Val Val Ala Gln Val Val
1               5                   10                  15

<210> SEQ ID NO 15
<211> LENGTH: 14
<212> TYPE: PRT
<213> ORGANISM: Artificial
<220> FEATURE:
<223> OTHER INFORMATION: CLDN6 epitope

<400> SEQUENCE: 15

Lys Val Thr Ala Phe Ile Gly Asn Ser Ile Val Val Ala Gln
1               5                   10

<210> SEQ ID NO 16
<211> LENGTH: 13
<212> TYPE: PRT
<213> ORGANISM: Artificial
<220> FEATURE:
<223> OTHER INFORMATION: CLDN6 epitope

<400> SEQUENCE: 16

Arg Asp Phe Tyr Asn Pro Leu Val Ala Glu Ala Gln Lys
1               5                   10

<210> SEQ ID NO 17
<211> LENGTH: 11
<212> TYPE: PRT
<213> ORGANISM: Artificial
<220> FEATURE:
<223> OTHER INFORMATION: CLDN6 epitope

<400> SEQUENCE: 17

Asp Phe Tyr Asn Pro Leu Val Ala Glu Ala Gln
1               5                   10

<210> SEQ ID NO 18
<211> LENGTH: 13
<212> TYPE: PRT
<213> ORGANISM: Artificial
<220> FEATURE:
<223> OTHER INFORMATION: CLDN6 epitope

<400> SEQUENCE: 18

Thr Ala His Ala Ile Ile Arg Asp Phe Tyr Asn Pro Leu
1               5                   10

<210> SEQ ID NO 19
<211> LENGTH: 12
<212> TYPE: PRT
<213> ORGANISM: Artificial
<220> FEATURE:
<223> OTHER INFORMATION: CLDN6 epitope

<400> SEQUENCE: 19

```
Asp Phe Tyr Asn Pro Leu Val Ala Glu Ala Gln Lys
1               5                   10

<210> SEQ ID NO 20
<211> LENGTH: 16
<212> TYPE: PRT
<213> ORGANISM: Artificial
<220> FEATURE:
<223> OTHER INFORMATION: CLDN6 epitope

<400> SEQUENCE: 20

Ile Arg Asp Phe Tyr Asn Pro Leu Val Ala Glu Ala Gln Lys Arg Glu
1               5                   10                  15

<210> SEQ ID NO 21
<211> LENGTH: 10
<212> TYPE: PRT
<213> ORGANISM: Artificial
<220> FEATURE:
<223> OTHER INFORMATION: CLDN18.2 epitope

<400> SEQUENCE: 21

Thr Gln Asp Leu Tyr Asn Asn Pro Val Thr
1               5                   10

<210> SEQ ID NO 22
<211> LENGTH: 11
<212> TYPE: PRT
<213> ORGANISM: Artificial
<220> FEATURE:
<223> OTHER INFORMATION: PLAC1 epitope

<400> SEQUENCE: 22

Val Phe Ser Glu Glu Glu His Thr Gln Val Pro
1               5                   10

<210> SEQ ID NO 23
<211> LENGTH: 10
<212> TYPE: PRT
<213> ORGANISM: Artificial
<220> FEATURE:
<223> OTHER INFORMATION: PLAC1 epitope

<400> SEQUENCE: 23

Val Phe Ser Glu Glu Glu His Thr Gln Val
1               5                   10

<210> SEQ ID NO 24
<211> LENGTH: 9
<212> TYPE: PRT
<213> ORGANISM: Artificial
<220> FEATURE:
<223> OTHER INFORMATION: linker sequence

<400> SEQUENCE: 24

Gly Gly Gly Gly Ser Gly Gly Gly Gly
1               5

<210> SEQ ID NO 25
<211> LENGTH: 166
<212> TYPE: PRT
<213> ORGANISM: Artificial
<220> FEATURE:
<223> OTHER INFORMATION: HBcAg Backbone "HBcAg Del 74-81" (Fig. 7A)

<400> SEQUENCE: 25

Met Val Asp Ala Ala Thr Ser Asp Ile Asp Pro Tyr Lys Glu Phe Gly
```

```
            1               5                  10                  15
Ala Thr Val Glu Leu Leu Ser Phe Leu Pro Ser Asp Phe Pro Ser
                20                  25                  30

Val Arg Asp Leu Leu Asp Thr Ala Ser Ala Leu Tyr Arg Glu Ala Leu
                35                  40                  45

Glu Ser Pro Glu His Cys Ser Pro His His Thr Ala Leu Arg Gln Ala
                50                  55                  60

Ile Leu Cys Trp Gly Glu Leu Met Thr Leu Ala Thr Trp Val Gly Gly
65                  70                  75                  80

Gly Gly Gly Ser Gly Gly Gly Arg Asp Leu Val Val Ser Tyr Val
                85                  90                  95

Asn Thr Asn Met Gly Leu Lys Phe Arg Gln Leu Leu Trp Phe His Ile
                100                 105                 110

Ser Cys Leu Thr Phe Gly Arg Glu Thr Val Ile Glu Tyr Leu Val Ser
                115                 120                 125

Phe Gly Val Trp Ile Arg Thr Pro Pro Ala Tyr Arg Pro Pro Asn Ala
                130                 135                 140

Pro Ile Leu Ser Thr Leu Pro Glu Thr Thr Val Val Arg Gly Gly Ser
145                 150                 155                 160

His His His His His His
                165

<210> SEQ ID NO 26
<211> LENGTH: 168
<212> TYPE: PRT
<213> ORGANISM: Artificial
<220> FEATURE:
<223> OTHER INFORMATION: HBcAg Backbone "HBcAg Del 76-81" (Fig. 7B)

<400> SEQUENCE: 26

Met Val Asp Ala Ala Thr Ser Asp Ile Asp Pro Tyr Lys Glu Phe Gly
1               5                  10                  15

Ala Thr Val Glu Leu Leu Ser Phe Leu Pro Ser Asp Phe Pro Ser
                20                  25                  30

Val Arg Asp Leu Leu Asp Thr Ala Ser Ala Leu Tyr Arg Glu Ala Leu
                35                  40                  45

Glu Ser Pro Glu His Cys Ser Pro His His Thr Ala Leu Arg Gln Ala
                50                  55                  60

Ile Leu Cys Trp Gly Glu Leu Met Thr Leu Ala Thr Trp Val Gly Val
65                  70                  75                  80

Asn Gly Gly Gly Ser Gly Gly Gly Gly Arg Asp Leu Val Val Ser
                85                  90                  95

Tyr Val Asn Thr Asn Met Gly Leu Lys Phe Arg Gln Leu Leu Trp Phe
                100                 105                 110

His Ile Ser Cys Leu Thr Phe Gly Arg Glu Thr Val Ile Glu Tyr Leu
                115                 120                 125

Val Ser Phe Gly Val Trp Ile Arg Thr Pro Pro Ala Tyr Arg Pro Pro
                130                 135                 140

Asn Ala Pro Ile Leu Ser Thr Leu Pro Glu Thr Thr Val Val Arg Gly
145                 150                 155                 160

Gly Ser His His His His His His
                165

<210> SEQ ID NO 27
<211> LENGTH: 170
<212> TYPE: PRT
```

```
<213> ORGANISM: Artificial
<220> FEATURE:
<223> OTHER INFORMATION: HBcAg Backbone "HBcAg Del 76-79" (Fig. 7C)

<400> SEQUENCE: 27

Met Val Asp Ala Ala Thr Ser Asp Ile Asp Pro Tyr Lys Glu Phe Gly
1               5                   10                  15

Ala Thr Val Glu Leu Leu Ser Phe Leu Pro Ser Asp Phe Phe Pro Ser
            20                  25                  30

Val Arg Asp Leu Leu Asp Thr Ala Ser Ala Leu Tyr Arg Glu Ala Leu
        35                  40                  45

Glu Ser Pro Glu His Cys Ser Pro His His Thr Ala Leu Arg Gln Ala
    50                  55                  60

Ile Leu Cys Trp Gly Glu Leu Met Thr Leu Ala Thr Trp Val Gly Val
65                  70                  75                  80

Asn Gly Gly Gly Gly Ser Gly Gly Gly Ala Ser Arg Asp Leu Val
                85                  90                  95

Val Ser Tyr Val Asn Thr Asn Met Gly Leu Lys Phe Arg Gln Leu Leu
            100                 105                 110

Trp Phe His Ile Ser Cys Leu Thr Phe Gly Arg Glu Thr Val Ile Glu
        115                 120                 125

Tyr Leu Val Ser Phe Gly Val Trp Ile Arg Thr Pro Pro Ala Tyr Arg
    130                 135                 140

Pro Pro Asn Ala Pro Ile Leu Ser Thr Leu Pro Glu Thr Thr Val Val
145                 150                 155                 160

Arg Gly Gly Ser His His His His His His
                165                 170

<210> SEQ ID NO 28
<211> LENGTH: 166
<212> TYPE: PRT
<213> ORGANISM: Artificial
<220> FEATURE:
<223> OTHER INFORMATION: HBcAg Backbone "HBcAg Del 79-80 linker"
      (Fig. 7D)

<400> SEQUENCE: 28

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Gly Gly
65                  70                  75                  80

Gly Gly Ser Gly Gly Gly Ser Arg Asp Leu Val Val Ser Tyr Val
                85                  90                  95

Asn Thr Asn Met Gly Leu Lys Phe Arg Gln Leu Leu Trp Phe His Ile
            100                 105                 110

Ser Cys Leu Thr Phe Gly Arg Glu Thr Val Ile Glu Tyr Leu Val Ser
        115                 120                 125

Phe Gly Val Trp Ile Arg Thr Pro Pro Ala Tyr Arg Pro Pro Asn Ala
    130                 135                 140

Pro Ile Leu Ser Thr Leu Pro Glu Thr Thr Val Val Arg Gly Gly Ser
145                 150                 155                 160
```

His His His His His His
            165

<210> SEQ ID NO 29
<211> LENGTH: 174
<212> TYPE: PRT
<213> ORGANISM: Artificial
<220> FEATURE:
<223> OTHER INFORMATION: HBcAg Backbone "HBcAg 77-Linker-78" (Fig. 7E)

<400> SEQUENCE: 29

Met Val Asp Ala Ala Thr Ser Asp Ile Asp Pro Tyr Lys Glu Phe Gly
1               5                   10                  15

Ala Thr Val Glu Leu Leu Ser Phe Leu Pro Ser Asp Phe Phe Pro Ser
            20                  25                  30

Val Arg Asp Leu Leu Asp Thr Ala Ser Ala Leu Tyr Arg Glu Ala Leu
        35                  40                  45

Glu Ser Pro Glu His Cys Ser Pro His His Thr Ala Leu Arg Gln Ala
    50                  55                  60

Ile Leu Cys Trp Gly Glu Leu Met Thr Leu Ala Thr Trp Val Gly Val
65                  70                  75                  80

Asn Leu Glu Gly Gly Gly Ser Gly Gly Gly Asp Pro Ala Ser
                85                  90                  95

Arg Asp Leu Val Val Ser Tyr Val Asn Thr Asn Met Gly Leu Lys Phe
                100                 105                 110

Arg Gln Leu Leu Trp Phe His Ile Ser Cys Leu Thr Phe Gly Arg Glu
            115                 120                 125

Thr Val Ile Glu Tyr Leu Val Ser Phe Gly Val Trp Ile Arg Thr Pro
    130                 135                 140

Pro Ala Tyr Arg Pro Pro Asn Ala Pro Ile Leu Ser Thr Leu Pro Glu
145                 150                 155                 160

Thr Thr Val Val Arg Gly Gly Ser His His His His His His
                165                 170

<210> SEQ ID NO 30
<211> LENGTH: 157
<212> TYPE: PRT
<213> ORGANISM: Artificial
<220> FEATURE:
<223> OTHER INFORMATION: HBcAg Backbone "HBcAg Del 79-80" (Fig. 7F)

<400> SEQUENCE: 30

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Ser Arg
65                  70                  75                  80

Asp Leu Val Val Ser Tyr Val Asn Thr Asn Met Gly Leu Lys Phe Arg
                85                  90                  95

Gln Leu Leu Trp Phe His Ile Ser Cys Leu Thr Phe Gly Arg Glu Thr
            100                 105                 110

Val Ile Glu Tyr Leu Val Ser Phe Gly Val Trp Ile Arg Thr Pro Pro

```
            115                 120                 125
Ala Tyr Arg Pro Pro Asn Ala Pro Ile Leu Ser Thr Leu Pro Glu Thr
        130                 135                 140

Thr Val Val Arg Gly Gly Ser His His His His His His
145                 150                 155

<210> SEQ ID NO 31
<211> LENGTH: 498
<212> TYPE: DNA
<213> ORGANISM: Artificial
<220> FEATURE:
<223> OTHER INFORMATION: HBcAg Backbone "HBcAg Del 74-81" (Fig. 7A)

<400> SEQUENCE: 31
atggtcgacg cggcgactag tgatattgat ccgtataaag aatttggcgc gaccgtggaa      60
ctgctgtctt ttctgccgag cgattttttt ccgagcgtgc gtgatctgct ggataccgcg     120
agcgcgctgt atcgtgaagc gctggaaagc ccggaacatt gcagcccgca tcataccgcg     180
ctgcgtcagg cgattctgtg ctggggcgaa ctgatgaccc tggccacctg ggttggcggc     240
ggtggaggat ccgtggcgg tggcagagat ctggtggtga gctatgtgaa caccaacatg     300
ggcctgaaat tcgccagct gctgtggttt catatcagct gcctgacctt tggccgtgaa     360
accgtgattg aatatctggt gagctttggc gtgtggattc gtacccgcc ggcatatcgt     420 ccgccgaacg cgccgattct gagcaccctg ccggaaacca ccgtcgtacg tggcggcagc     480
catcatcatc atcaccat                                                   498

<210> SEQ ID NO 32
<211> LENGTH: 504
<212> TYPE: DNA
<213> ORGANISM: Artificial
<220> FEATURE:
<223> OTHER INFORMATION: HBcAg Backbone "HBcAg Del 76-81" (Fig. 7B)

<400> SEQUENCE: 32
atggtcgacg cggcgactag tgatattgat ccgtataaag aatttggcgc gaccgtggaa      60
ctgctgtctt ttctgccgag cgattttttt ccgagcgtgc gtgatctgct ggataccgcg     120
agcgcgctgt atcgtgaagc gctggaaagc ccggaacatt gcagcccgca tcataccgcg     180
ctgcgtcagg cgattctgtg ctggggcgaa ctgatgaccc tggccacctg ggttggcgtg     240
aacggcggtg aggatccgg tggcggtggc agagatctgg tggtgagcta tgtgaacacc     300
aacatgggcc tgaaatttcg ccagctgctg tggtttcata tcagctgcct gacctttggc     360
cgtgaaaccg tgattgaata tctggtgagc tttggcgtgt ggattcgtac cccgccggca     420
tatcgtccgc cgaacgcgcc gattctgagc accctgccgg aaaccaccgt cgtacgtggc     480
ggcagccatc atcatcatca ccat                                            504

<210> SEQ ID NO 33
<211> LENGTH: 510
<212> TYPE: DNA
<213> ORGANISM: Artificial
<220> FEATURE:
<223> OTHER INFORMATION: HBcAg Backbone "HBcAg Del 76-79" (Fig. 7C)

<400> SEQUENCE: 33
atggtcgacg cggcgactag tgatattgat ccgtataaag aatttggcgc gaccgtggaa      60
ctgctgtctt ttctgccgag cgattttttt ccgagcgtgc gtgatctgct ggataccgcg     120
agcgcgctgt atcgtgaagc gctggaaagc ccggaacatt gcagcccgca tcataccgcg     180
```

```
ctgcgtcagg cgattctgtg ctggggcgaa ctgatgaccc tggccacctg ggtgggcgtg      240
aacggcggtg gaggatccgg tggcggtggc gcgtctagag atctggtggt gagctatgtg      300
aacaccaaca tgggcctgaa atttcgccag ctgctgtggt tcatatcag ctgcctgacc       360 tttggccgtg aaaccgtgat tgaatatctg gtgagctttg gcgtgtggat tcgtaccccg      420
ccggcatatc gtccgccgaa cgcgccgatt ctgagcaccc tgccggaaac caccgtcgta     480
cgtggcggca gccatcatca tcatcaccat                                       510
```

<210> SEQ ID NO 34
<211> LENGTH: 498
<212> TYPE: DNA
<213> ORGANISM: Artificial
<220> FEATURE:
<223> OTHER INFORMATION: HBcAg Backbone "HBcAg Del 79-80 linker"
      (Fig. 7D)

<400> SEQUENCE: 34

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggatggtggc     240
ggcggatccg gtggcggtgg ttctagagac tggtggtga gctatgtgaa caccaacatg      300
ggcctgaaat tcgccaact gctgtggttt catattagct gcctgacctt ggccgtgaa      360 accgtgattg aatatctggt gagctttggc gtttggattc gtaccccgcc agcgtatcgt    420
ccgccgaacg cgccgattct gagcaccctg ccggaaacca ccgttgttcg cggcggtagc    480
catcatcatc atcaccat                                                    498
```

<210> SEQ ID NO 35
<211> LENGTH: 522
<212> TYPE: DNA
<213> ORGANISM: Artificial
<220> FEATURE:
<223> OTHER INFORMATION: HBcAg Backbone "HBcAg 77-Linker-78" (Fig. 7E)

<400> SEQUENCE: 35

```
atggtcgacg cggcgactag tgatattgat ccgtataaag aatttggcgc gaccgtggaa      60
ctgctgtctt ttctgccgag cgatttttt ccgagcgtgc gtgatctgct ggataccgcg     120
agcgcgctgt atcgtgaagc gctggaaagc ccggaacatt gcagcccgca tcataccgcg     180
ctgcgtcagg cgattctgtg ctggggcgaa ctgatgaccc tggccacctg ggtgggcgtg     240
aacctcgagg gcggtggagg atccggtggc ggtggcgatc cggcgtctag agatctggtg     300
gtgagctatg tgaacaccaa catgggcctg aaatttcgcc agctgctgtg gtttcatatc     360
agctgcctga cctttggccg tgaaaccgtg attgaatatc tggtgagctt ggcgtgtgg     420 attcgtaccc cgccggcata tcgtccgccg aacgcgccga ttctgagcac cctgccggaa     480
accaccgtcg tacgtggcgg cagccatcat catcatcacc at                         522
```

<210> SEQ ID NO 36
<211> LENGTH: 471
<212> TYPE: DNA
<213> ORGANISM: Artificial
<220> FEATURE:
<223> OTHER INFORMATION: HBcAg Backbone "HBcAg Del 79-80" (Fig. 7F)

<400> SEQUENCE: 36

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggactctaga     240
gacctggtgg tgagctatgt gaacaccaac atgggcctga atttcgcca actgctgtgg      300
tttcatatta gctgcctgac ctttggccgt gaaaccgtga ttgaatatct ggtgagcttt     360
ggcgtttgga ttcgtacccc gccagcgtat cgtccgccga acgcgccgat tctgagcacc     420
ctgccggaaa ccaccgttgt tcgcggcggt agccatcatc atcatcacca t              471
```

```
<210> SEQ ID NO 37
<211> LENGTH: 185
<212> TYPE: PRT
<213> ORGANISM: Artificial
<220> FEATURE:
<223> OTHER INFORMATION: chimeric HBcAg construct "HBcAg Del 79-80
      linker CLDN18.2-EC1 short" (Fig. 8A)

<400> SEQUENCE: 37

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Gly Gly
65                  70                  75                  80

Gly Gly Ser Gly Gly Gly Gly

```
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Thr Gln
65                  70                  75                  80

Asp Leu Tyr Asn Asn Pro Val Thr Ser Arg Asp Leu Val Val Ser Tyr
                85                  90                  95
Val Asn Thr Asn Met Gly Leu Lys Phe Arg Gln Leu Leu Trp Phe His
            100                 105                 110
Ile Ser Cys Leu Thr Phe Gly Arg Glu Thr Val Ile Glu Tyr Leu Val
        115                 120                 125
Ser Phe Gly Val Trp Ile Arg Thr Pro Pro Ala Tyr Arg Pro Pro Asn
    130                 135                 140

Ala Pro Ile Leu Ser Thr Leu Pro Glu Thr Thr Val Val Arg Gly Gly
145                 150                 155                 160

Ser His His His His His His
                165

<210> SEQ ID NO 39
<211> LENGTH: 186
<212> TYPE: PRT
<213> ORGANISM: Artificial
<220> FEATURE:
<223> OTHER INFORMATION: chimeric HBcAg construct "HBcAg Del 79-80
      linker PLAC1 3rd Loop A" (Fig. 8C)

<400> SEQUENCE: 39

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30
Thr Ala Ser Ala Leu Tyr Arg Glu Ala Leu Glu Ser Pro Glu His Cys
        35                  40                  45
Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Gly Gly
65                  70                  75                  80

Gly Gly Ser Gly Gly Gly Gly Val Phe Ser Glu Glu Glu His Thr Gln
                85                  90                  95

Val Pro Gly Gly Gly Gly Ser Gly Gly Gly Gly Ser Arg Asp Leu Val
            100                 105                 110

Val Ser Tyr Val Asn Thr Asn Met Gly Leu Lys Phe Arg Gln Leu Leu
        115                 120                 125

Trp Phe His Ile Ser Cys Leu Thr Phe Gly Arg Glu Thr Val Ile Glu
    130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175

Arg Gly Gly Ser His His His His His His
            180                 185

<210> SEQ ID NO 40
<211> LENGTH: 167
```

Figure 8D:
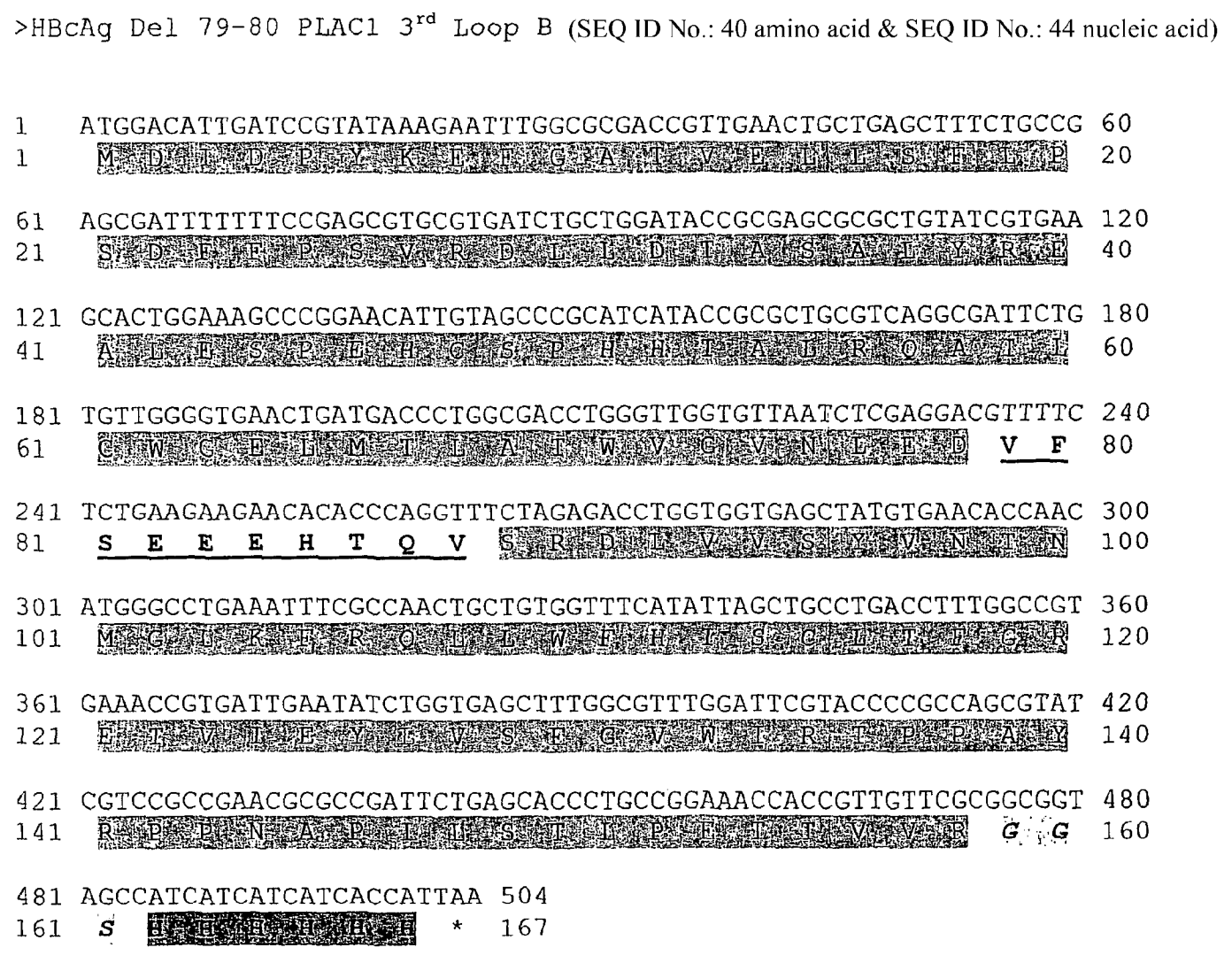

<212> TYPE: PRT
<213> ORGANISM: Artificial
<220> FEATURE:
<223> OTHER INFORMATION: chimeric HBcAg construct "HBcAg Del 79-80 PLAC1 3rd Loop B" (Fig. 8D)

<400> SEQUENCE: 40

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Val Phe
65                  70                  75                  80

Ser Glu Glu Glu His Thr Gln Val Ser Arg Asp Leu Val Val Ser Tyr
                85                  90                  95

Val Asn Thr Asn Met Gly Leu Lys Phe Arg Gln Leu Leu Trp Phe His
            100                 105                 110

Ile Ser Cys Leu Thr Phe Gly Arg Glu Thr Val Ile Glu Tyr Leu Val
        115                 120                 125

Ser Phe Gly Val Trp Ile Arg Thr Pro Pro Ala Tyr Arg Pro Pro Asn
    130                 135                 140

Ala Pro Ile Leu Ser Thr Leu Pro Glu Thr Thr Val Val Arg Gly Gly
145                 150                 155                 160

Ser His His His His His His
                165

<210> SEQ ID NO 41
<211> LENGTH: 555
<212> TYPE: DNA
<213> ORGANISM: Artificial
<220> FEATURE:
<223> OTHER INFORMATION: chimeric HBcAg construct "HBcAg Del 79-80 linker CLDN18.2-EC1 short" (Fig. 8A)

<400> SEQUENCE: 41
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggatggtggc     240
ggcggatccg gcggaggcgg aacccaggat ctgtataaca atccggtgac cggcggaggc     300
ggatccggtg gcggtggttc tagagacctg gtggtgagct atgtgaacac caacatgggc     360
ctgaaatttc gccaactgct gtggtttcat attagctgcc tgaccttt gg ccgtgaaacc    420 gtgattgaat atctggtgag ctttggcgtt tggattcgta ccccgccagc gtatcgtccg     480
ccgaacgcgc cgattctgag caccctgccg gaaaccaccg ttgttcgcgg cggtagccat     540
catcatcatc accat                                                      555

<210> SEQ ID NO 42
<211> LENGTH: 501
<212> TYPE: DNA
<213> ORGANISM: Artificial
<220> FEATURE:
<223> OTHER INFORMATION: chimeric HBcAg construct "HBcAg Del 79-80

CLDN18.2-EC1 short" (Fig. 8B)

<400> SEQUENCE: 42

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggacacccag     240
gatctgtata caacccggt gacctctaga gacctggtgg tgagctatgt gaacaccaac      300
atgggcctga aatttcgcca actgctgtgg tttcatatta gctgcctgac ctttggccgt     360
gaaaccgtga ttgaatatct ggtgagcttt ggcgtttgga ttcgtacccc gccagcgtat     420
cgtccgccga acgcgccgat tctgagcacc ctgccggaaa ccaccgttgt tcgcggcggt     480
agccatcatc atcatcacca t                                               501
```

<210> SEQ ID NO 43
<211> LENGTH: 558
<212> TYPE: DNA
<213> ORGANISM: Artificial
<220> FEATURE:
<223> OTHER INFORMATION: chimeric HBcAg construct "HBcAg Del 79-80 linker PLAC1 3rd Loop A" (Fig. 8C)

<400> SEQUENCE: 43

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggatggtggc     240
ggcggatccg gcggaggcgg agttttctct gaagaagaac acacccaggt tccgggcgga     300
ggcggatccg gtggcggtgg ttctagagac ctggtggtga gctatgtgaa caccaacatg     360
ggcctgaaat tcgccaact gctgtggttt catattagct gcctgacctt tggccgtgaa      420
accgtgattg aatatctggt gagctttggc gtttggattc gtaccccgcc agcgtatcgt     480
ccgccgaacg cgccgattct gagcaccctg ccggaaacca ccgttgttcg cggcggtagc     540
catcatcatc atcaccat                                                  558
```

<210> SEQ ID NO 44
<211> LENGTH: 501
<212> TYPE: DNA
<213> ORGANISM: Artificial
<220> FEATURE:
<223> OTHER INFORMATION: chimeric HBcAg construct "HBcAg Del 79-80 PLAC1 3rd Loop B" (Fig. 8D)

<400> SEQUENCE: 44

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggacgttttc     240
tctgaagaag aacacaccca ggtttctaga gacctggtgg tgagctatgt gaacaccaac     300
atgggcctga aatttcgcca actgctgtgg tttcatatta gctgcctgac ctttggccgt     360
gaaaccgtga ttgaatatct ggtgagcttt ggcgtttgga ttcgtacccc gccagcgtat     420
cgtccgccga acgcgccgat tctgagcacc ctgccggaaa ccaccgttgt tcgcggcggt     480
```
agccatcatc atcatcacca t					501

<210> SEQ ID NO 45
<211> LENGTH: 16
<212> TYPE: PRT
<213> ORGANISM: Artificial
<220> FEATURE:
<223> OTHER INFORMATION: CLDN18.2 epitope

<400> SEQUENCE: 45

Asp Leu Tyr Asn Asn Pro Val Thr Ala Val Phe Asn Tyr Gln Gly Leu
1               5                   10                  15

<210> SEQ ID NO 46
<211> LENGTH: 11
<212> TYPE: PRT
<213> ORGANISM: Artificial
<220> FEATURE:
<223> OTHER INFORMATION: CLDN18.2 epitope

<400> SEQUENCE: 46

Asn Asn Pro Val Thr Ala Val Phe Asn Tyr Gln
1               5                   10

<210> SEQ ID NO 47
<211> LENGTH: 10
<212> TYPE: PRT
<213> ORGANISM: Artificial
<220> FEATURE:
<223> OTHER INFORMATION: CLDN18.2 epitope

<400> SEQUENCE: 47

Val Thr Ala Val Phe Asn Tyr Gln Gly Leu
1               5                   10

<210> SEQ ID NO 48
<211> LENGTH: 9
<212> TYPE: PRT
<213> ORGANISM: Artificial
<220> FEATURE:
<223> OTHER INFORMATION: CLDN18.2 epitope

<400> SEQUENCE: 48

Ser Cys Val Arg Glu Ser Ser Gly Phe
1               5

<210> SEQ ID NO 49
<211> LENGTH: 8
<212> TYPE: PRT
<213> ORGANISM: Artificial
<220> FEATURE:
<223> OTHER INFORMATION: CLDN18.2 epitope

<400> SEQUENCE: 49

Val Arg Glu Ser Ser Gly Phe Thr
1               5

<210> SEQ ID NO 50
<211> LENGTH: 9
<212> TYPE: PRT
<213> ORGANISM: Artificial
<220> FEATURE:
<223> OTHER INFORMATION: CLDN18.2 epitope

<400> SEQUENCE: 50

Val Arg Glu Ser Ser Gly Phe Thr Glu

```
<210> SEQ ID NO 51
<211> LENGTH: 9
<212> TYPE: PRT
<213> ORGANISM: Artificial
<220> FEATURE:
<223> OTHER INFORMATION: CLDN18.2 epitope

<400> SEQUENCE: 51

Arg Gly Tyr Phe Thr Leu Leu Gly Leu
1               5

<210> SEQ ID NO 52
<211> LENGTH: 11
<212> TYPE: PRT
<213> ORGANISM: Artificial
<220> FEATURE:
<223> OTHER INFORMATION: CLDN18.2 epitope

<400> SEQUENCE: 52

Glu Cys Arg Gly Tyr Phe Thr Leu Leu Gly Leu
1               5                   10

<210> SEQ ID NO 53
<211> LENGTH: 16
<212> TYPE: PRT
<213> ORGANISM: Artificial
<220> FEATURE:
<223> OTHER INFORMATION: CLDN18.2 epitope

<400> SEQUENCE: 53

Ala Val Phe Asn Tyr Gln Gly Leu Trp Arg Ser Cys Val Arg Glu Ser
1               5                   10                  15

<210> SEQ ID NO 54
<211> LENGTH: 20
<212> TYPE: PRT
<213> ORGANISM: Artificial
<220> FEATURE:
<223> OTHER INFORMATION: CLDN18.2 epitope

<400> SEQUENCE: 54

Asp Gln Trp Ser Thr Gln Asp Leu Tyr Asn Asn Pro Val Thr Ala Val
1               5                   10                  15

Phe Asn Tyr Gln
            20

<210> SEQ ID NO 55
<211> LENGTH: 23
<212> TYPE: PRT
<213> ORGANISM: Artificial
<220> FEATURE:
<223> OTHER INFORMATION: CLDN18.2 epitope

<400> SEQUENCE: 55

Met Asp Gln Trp Ser Thr Gln Asp Leu Tyr Asn Asn Pro Val Thr Ala
1               5                   10                  15

Val Phe Asn Tyr Gln Gly Leu
            20

<210> SEQ ID NO 56
<211> LENGTH: 31
<212> TYPE: PRT
<213> ORGANISM: Artificial
<220> FEATURE:
```

<223> OTHER INFORMATION: CLDN18.2 epitope

<400> SEQUENCE: 56

Trp Arg Ser Cys Val Arg Glu Ser Ser Gly Phe Thr Glu Cys Arg Gly
1               5                   10                  15

Tyr Phe Thr Leu Leu Gly Leu Pro Ala Met Leu Gln Ala Val Arg
            20                  25                  30

<210> SEQ ID NO 57
<211> LENGTH: 17
<212> TYPE: PRT
<213> ORGANISM: Artificial
<220> FEATURE:
<223> OTHER INFORMATION: CLDN18.2 epitope

<400> SEQUENCE: 57

Arg Ile Gly Ser Met Glu Asp Ser Ala Lys Ala Asn Met Thr Leu Thr
1               5                   10                  15

Ser

<210> SEQ ID NO 58
<211> LENGTH: 27
<212> TYPE: PRT
<213> ORGANISM: Artificial
<220> FEATURE:
<223> OTHER INFORMATION: CLDN18.2 epitope

<400> SEQUENCE: 58

Thr Asn Phe Trp Met Ser Thr Ala Asn Met Tyr Thr Gly Met Gly Gly
1               5                   10                  15

Met Val Gln Thr Val Gln Thr Arg Tyr Thr Phe
            20                  25

<210> SEQ ID NO 59
<211> LENGTH: 11
<212> TYPE: PRT
<213> ORGANISM: Artificial
<220> FEATURE:
<223> OTHER INFORMATION: PLAC1 epitope

<400> SEQUENCE: 59

Ala Pro Gln Lys Ser Pro Trp Leu Thr Lys Pro
1               5                   10

<210> SEQ ID NO 60
<211> LENGTH: 9
<212> TYPE: PRT
<213> ORGANISM: Artificial
<220> FEATURE:
<223> OTHER INFORMATION: PLAC1 epitope

<400> SEQUENCE: 60

Gln Lys Ser Pro Trp Leu Thr Lys Pro
1               5

<210> SEQ ID NO 61
<211> LENGTH: 9
<212> TYPE: PRT
<213> ORGANISM: Artificial
<220> FEATURE:
<223> OTHER INFORMATION: PLAC1 epitope

<400> SEQUENCE: 61

Ala Pro Gln Lys Ser Pro Trp Leu Thr
1               5

```
<210> SEQ ID NO 62
<211> LENGTH: 8
<212> TYPE: PRT
<213> ORGANISM: Artificial
<220> FEATURE:
<223> OTHER INFORMATION: PLAC1 epitope

<400> SEQUENCE: 62

Met Arg Val Ala Ser Lys Ser Arg
1               5

<210> SEQ ID NO 63
<211> LENGTH: 6
<212> TYPE: PRT
<213> ORGANISM: Artificial
<220> FEATURE:
<223> OTHER INFORMATION: PLAC1 epitope

<400> SEQUENCE: 63

Ala Pro Gln Lys Ser Pro
1               5

<210> SEQ ID NO 64
<211> LENGTH: 7
<212> TYPE: PRT
<213> ORGANISM: Artificial
<220> FEATURE:
<223> OTHER INFORMATION: PLAC1 epitope

<400> SEQUENCE: 64

Thr Ala Gln Lys Asp Glu Lys
1               5

<210> SEQ ID NO 65
<211> LENGTH: 7
<212> TYPE: PRT
<213> ORGANISM: Artificial
<220> FEATURE:
<223> OTHER INFORMATION: PLAC1 epitope

<400> SEQUENCE: 65

Ser Lys Gly Thr Pro Ser Lys
1               5

<210> SEQ ID NO 66
<211> LENGTH: 10
<212> TYPE: PRT
<213> ORGANISM: Artificial
<220> FEATURE:
<223> OTHER INFORMATION: PLAC1 epitope

<400> SEQUENCE: 66

Ala Pro Gln Lys Ser Pro Trp Leu Thr Lys
1               5                   10

<210> SEQ ID NO 67
<211> LENGTH: 8
<212> TYPE: PRT
<213> ORGANISM: Artificial
<220> FEATURE:
<223> OTHER INFORMATION: PLAC1 epitope

<400> SEQUENCE: 67

Gln Lys Ser Pro Trp Leu Thr Lys
1               5
```

```
<210> SEQ ID NO 68
<211> LENGTH: 17
<212> TYPE: PRT
<213> ORGANISM: Artificial
<220> FEATURE:
<223> OTHER INFORMATION: PLAC1 epitope

<400> SEQUENCE: 68

Ser Met Arg Val Ala Ser Lys Ser Arg Ala Thr Ala Gln Lys Asp Glu
1               5                   10                  15

Lys

<210> SEQ ID NO 69
<211> LENGTH: 18
<212> TYPE: PRT
<213> ORGANISM: Artificial
<220> FEATURE:
<223> OTHER INFORMATION: PLAC1 epitope

<400> SEQUENCE: 69

Pro Pro Asn His Val Gln Pro His Ala Tyr Gln Phe Thr Tyr Arg Val
1               5                   10                  15

Thr Glu

<210> SEQ ID NO 70
<211> LENGTH: 17
<212> TYPE: PRT
<213> ORGANISM: Artificial
<220> FEATURE:
<223> OTHER INFORMATION: PLAC1 epitope

<400> SEQUENCE: 70

Ser Met Arg Val Ala Ser Lys Ser Lys Arg Ala Thr Ala Gln Lys Asp
1               5                   10                  15

Glu

<210> SEQ ID NO 71
<211> LENGTH: 16
<212> TYPE: PRT
<213> ORGANISM: Artificial
<220> FEATURE:
<223> OTHER INFORMATION: PLAC1 epitope

<400> SEQUENCE: 71

Ser Met Arg Val Ala Ser Lys Ser Lys Arg Ala Thr Ala Gln Lys Asp
1               5                   10                  15

<210> SEQ ID NO 72
<211> LENGTH: 15
<212> TYPE: PRT
<213> ORGANISM: Artificial
<220> FEATURE:
<223> OTHER INFORMATION: PLAC1 epitope

<400> SEQUENCE: 72

Ser Met Arg Val Ala Ser Lys Ser Lys Arg Ala Thr Ala Gln Lys
1               5                   10                  15

<210> SEQ ID NO 73
<211> LENGTH: 11
<212> TYPE: PRT
<213> ORGANISM: Artificial
<220> FEATURE:
<223> OTHER INFORMATION: PLAC1 epitope
```

```
<400> SEQUENCE: 73

Arg Val Ala Ser Lys Ser Lys Arg Ala Thr Ala
1               5                   10

<210> SEQ ID NO 74
<211> LENGTH: 14
<212> TYPE: PRT
<213> ORGANISM: Artificial
<220> FEATURE:
<223> OTHER INFORMATION: PLAC1 epitope

<400> SEQUENCE: 74

Tyr Glu Val Phe Ser Leu Ser Gln Ser Ser Gln Arg Pro Asn
1               5                   10

<210> SEQ ID NO 75
<211> LENGTH: 11
<212> TYPE: PRT
<213> ORGANISM: Artificial
<220> FEATURE:
<223> OTHER INFORMATION: PLAC1 epitope

<400> SEQUENCE: 75

Glu Val Phe Ser Leu Ser Gln Ser Ser Gln Arg
1               5                   10

<210> SEQ ID NO 76
<211> LENGTH: 17
<212> TYPE: PRT
<213> ORGANISM: Artificial
<220> FEATURE:
<223> OTHER INFORMATION: PLAC1 epitope

<400> SEQUENCE: 76

Ile Asp Trp Phe Met Val Thr Val His Pro Phe Met Leu Asn Asn Asp
1               5                   10                  15

Val

<210> SEQ ID NO 77
<211> LENGTH: 16
<212> TYPE: PRT
<213> ORGANISM: Artificial
<220> FEATURE:
<223> OTHER INFORMATION: PLAC1 epitope

<400> SEQUENCE: 77

Ile Asp Trp Phe Met Val Thr Val His Pro Phe Met Leu Asn Asn Asp
1               5                   10                  15

<210> SEQ ID NO 78
<211> LENGTH: 15
<212> TYPE: PRT
<213> ORGANISM: Artificial
<220> FEATURE:
<223> OTHER INFORMATION: PLAC1 epitope

<400> SEQUENCE: 78

Ile Asp Trp Phe Met Val Thr Val His Pro Phe Met Leu Asn Asn
1               5                   10                  15

<210> SEQ ID NO 79
<211> LENGTH: 159
<212> TYPE: PRT
<213> ORGANISM: Artificial
<220> FEATURE:
<223> OTHER INFORMATION: HBcAg (delta); C-terminal deletion, including a
```

C-terminal glycine linker and His-tag

<400> SEQUENCE: 79

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Gly Gly Ser His His His His His His
145                 150                 155

<210> SEQ ID NO 80
<211> LENGTH: 477
<212> TYPE: DNA
<213> ORGANISM: Artificial
<220> FEATURE:
<223> OTHER INFORMATION: codon-optimized nucleic acid sequence encoding
      HBcAg(delta), C-terminal truncation including a C-terminal glycine
      linker and His-tag

<400> SEQUENCE: 80

```
atggacattg atccgtataa agaatttggc gcgaccgttg aactgctgag ctttctgccg      60
agcgattttt ttccgagcgt gcgtgatctg ctggataccg cgagcgcgct gtatcgtgaa     120
gcactggaaa gcccggaaca ttgtagcccg catcataccg cgctgcgtca ggcgattctg     180
tgttggggtg aactgatgac cctggcgacc tgggttggtg ttaatctcga ggacccggct     240
tctagagacc tggtggtgag ctatgtgaac accaacatgg gcctgaaatt tcgccaactg     300
ctgtggtttc atattagctg cctgaccttt ggcgtgaaa ccgtgattga atatctggtg      360
agctttggcg tttggattcg tacccccgcca gcgtatcgtc cgccgaacgc gccgattctg    420
agcaccctgc cggaaaccac cgttgttcgc ggcggtagcc atcatcatca tcaccat       477
```

The invention claimed is:

1. A protein comprising all or a portion of the amino acid sequence of a hepatitis B virus core antigen protein and inserted therein or attached thereto an amino acid sequence comprising an epitope, wherein the epitope is derived from an extracellular portion of a tumor-associated antigen associated with the surface of a tumor cell which comprises an amino acid sequence selected from the group consisting of;
   (i) the amino acid sequences set forth in SEQ ID NOs: 37 to 40; and
   (ii) an amino acid sequence that is at least 80% identical to and is immunologically equivalent to the amino acid sequence under (i).

2. An immunogenic composition comprising the protein of claim 1.

3. A method of therapeutic treatment of tumors in a subject, comprising administering to the subject the protein of claim 1.

4. A method for eliciting a humoral immune response against a tumor-associated antigen in a subject, comprising the step of administering to said subject the protein of claim 1, wherein the tumor-associated antigen is a self-protein in said subject and wherein said subject is afflicted with a tumor or is at risk of developing a tumor, said tumor being characterized by association of the tumor-associated antigen with the surface of a tumor cell, wherein administering is optionally without adjuvant.

5. A method for breaking self-tolerance towards a tumor-associated antigen in a subject or for treating a tumor in a subject, said method comprising administering to said subject the protein of claim 1 wherein administering is optionally without adjuvant.

\* \* \* \* \*